United States Patent
Angros

(10) Patent No.: US 9,766,165 B2
(45) Date of Patent: *Sep. 19, 2017

(54) IN SITU HEAT INDUCED ANTIGEN RECOVERY AND STAINING APPARATUS AND METHOD

(71) Applicant: Lee H. Angros, Bethany, OK (US)

(72) Inventor: Lee H. Angros, Bethany, OK (US)

(*) Notice: Subject to any disclaimer, the term of this patent is extended or adjusted under 35 U.S.C. 154(b) by 28 days.

This patent is subject to a terminal disclaimer.

(21) Appl. No.: 15/050,132

(22) Filed: Feb. 22, 2016

(65) Prior Publication Data

US 2016/0169777 A1 Jun. 16, 2016

Related U.S. Application Data

(63) Continuation of application No. 13/943,510, filed on Jul. 16, 2013, now Pat. No. 9,267,868, which is a continuation of application No. 12/550,296, filed on Aug. 28, 2009, now Pat. No. 8,486,335.

(60) Provisional application No. 61/190,503, filed on Aug. 29, 2008.

(51) Int. Cl.
| | |
|---|---|
| *G01N 31/00* | (2006.01) |
| *G01N 33/53* | (2006.01) |
| *G01N 1/31* | (2006.01) |
| *B01L 3/02* | (2006.01) |
| *G01N 1/44* | (2006.01) |
| *G01N 35/00* | (2006.01) |
| *B01L 7/00* | (2006.01) |

(52) U.S. Cl.
CPC ............ *G01N 1/312* (2013.01); *B01L 3/0293* (2013.01); *G01N 1/44* (2013.01); *G01N 35/00029* (2013.01); *B01J 2219/0036* (2013.01); *B01J 2219/00477* (2013.01); *B01J 2219/00495* (2013.01); *B01J 2219/00533* (2013.01); *B01J 2219/00659* (2013.01); *B01L 7/54* (2013.01); *B01L 2200/04* (2013.01); *B01L 2200/16* (2013.01); *B01L 2300/0822* (2013.01); *B01L 2300/14* (2013.01); *B01L 2400/0478* (2013.01); *G01N 2035/00039* (2013.01); *G01N 2035/00138* (2013.01); *G01N 2035/00168* (2013.01); *G01N 2035/00346* (2013.01); *Y10T 436/11* (2015.01); *Y10T 436/110833* (2015.01); *Y10T 436/111666* (2015.01); *Y10T 436/112499* (2015.01); *Y10T 436/114165* (2015.01)

(58) Field of Classification Search
CPC ...... G01N 1/44; B01L 7/54; B01J 2219/0036; B01J 2219/00477; B01J 2219/00495
USPC .......................................................... 422/50
See application file for complete search history.

(56) References Cited

U.S. PATENT DOCUMENTS

| | | |
|---|---|---|
| 3,645,690 A | 2/1972 | Rochte et al. |
| 4,296,070 A | 10/1981 | Montalto et al. |
| 4,510,119 A | 4/1985 | Hevey |
| 4,847,208 A | 7/1989 | Bogen |
| 4,855,109 A | 8/1989 | Muraishi et al. |
| 4,857,272 A | 8/1989 | Sugaya |
| 5,073,504 A | 12/1991 | Bogen |
| 5,154,889 A | 10/1992 | Muraishi |
| 5,225,325 A | 7/1993 | Miller et al. |
| 5,232,664 A | 8/1993 | Krawzak et al. |
| 5,244,787 A | 9/1993 | Key et al. |
| 5,250,262 A | 10/1993 | Heidt et al. |
| 5,273,905 A | 12/1993 | Muller et al. |
| 5,316,452 A | 5/1994 | Bogen et al. |
| 5,355,439 A | 10/1994 | Bernstein et al. |
| 5,356,595 A | 10/1994 | Kanamori et al. |
| 5,425,918 A | 6/1995 | Healey et al. |
| 5,439,649 A | 8/1995 | Tseung et al. |
| 5,525,514 A | 6/1996 | Jacobs et al. |
| 5,551,487 A | 9/1996 | Gordon et al. |
| 5,578,452 A | 11/1996 | Shi et al. |
| 5,595,707 A | 1/1997 | Copeland et al. |
| 5,601,650 A | 2/1997 | Goldbecker et al. |
| 5,645,114 A | 7/1997 | Bogen et al. |
| 5,650,327 A | 7/1997 | Copeland et al. |
| 5,654,199 A | 8/1997 | Copeland et al. |
| 5,654,200 A | 8/1997 | Copeland et al. |
| 5,675,715 A | 10/1997 | Bernstein et al. |
| 5,696,887 A | 12/1997 | Bernstein et al. |
| 5,737,499 A | 4/1998 | Bernstein et al. |
| 5,758,033 A | 5/1998 | Bernstein et al. |

(Continued)

FOREIGN PATENT DOCUMENTS

| | | |
|---|---|---|
| DE | 20 2004 02163 | 10/2004 |
| EP | 402994 | 12/1990 |
| EP | 0947135 | 4/2005 |
| EP | 06771115.0 | 6/2012 |
| JP | 2001-4506 | 1/2001 |
| JP | 2003-57156 | 2/2003 |
| WO | 99/34190 | 7/1999 |
| WO | 99/44030 | 9/1999 |
| WO | 99/44032 | 9/1999 |
| WO | 00/14507 | 3/2000 |

(Continued)

OTHER PUBLICATIONS

U.S. Appl. No. 60/076,198, filed Feb. 27, 1998, Ford et al.

(Continued)

*Primary Examiner* — Lisa Cook
(74) *Attorney, Agent, or Firm* — Dunlap Codding, P.C.

(57) ABSTRACT

An automated microscope slide staining system and staining apparatus and method that features a plurality of individually operable miniaturized pressurizable reaction compartments or a pressurizable common chamber for individually and independently processing a plurality of microscope slides. The apparatus preferably features independently movable slide support elements each having an individually operable heating element.

42 Claims, 42 Drawing Sheets

(56) References Cited

U.S. PATENT DOCUMENTS

| | | |
|---|---|---|
| 5,804,141 A | 9/1998 | Chianese |
| 5,819,842 A | 10/1998 | Potter et al. |
| 5,839,091 A | 11/1998 | Rhett et al. |
| 5,882,601 A | 3/1999 | Kath et al. |
| 5,922,604 A | 7/1999 | Stapleton et al. |
| 5,947,167 A | 9/1999 | Bogen et al. |
| 5,948,359 A | 9/1999 | Kalra et al. |
| 5,958,341 A | 9/1999 | Chu |
| 5,985,669 A | 11/1999 | Palander |
| 6,093,574 A | 7/2000 | Druyor-Sanchez et al. |
| 6,096,271 A | 8/2000 | Bogen et al. |
| 6,180,061 B1 | 1/2001 | Bogen et al. |
| 6,183,693 B1 | 2/2001 | Bogen et al. |
| 6,207,408 B1 | 3/2001 | Essenfeld et al. |
| 6,218,191 B1 | 4/2001 | Palander |
| 6,245,297 B1 | 6/2001 | Kowallis |
| 6,269,846 B1 | 8/2001 | Overbeck et al. |
| 6,296,809 B1 | 10/2001 | Richards et al. |
| 6,352,861 B1 | 3/2002 | Copeland et al. |
| 6,358,473 B1 | 3/2002 | Coello et al. |
| 6,403,036 B1 | 6/2002 | Rodgers et al. |
| 6,403,931 B1 | 6/2002 | Showalter et al. |
| 6,451,551 B1 | 9/2002 | Zhan et al. |
| 6,472,217 B1 | 10/2002 | Richards et al. |
| 6,489,171 B1 | 12/2002 | Aghassi et al. |
| 6,495,106 B1 | 12/2002 | Kalra et al. |
| 6,534,008 B1 | 3/2003 | Angros |
| 6,541,261 B1 | 4/2003 | Bogen et al. |
| 6,544,798 B1 | 4/2003 | Christensen et al. |
| 6,582,962 B1 | 6/2003 | Richards et al. |
| 6,594,537 B1 | 7/2003 | Bernstein et al. |
| 6,632,598 B1 | 10/2003 | Zhang et al. |
| 6,638,770 B1 | 10/2003 | Montagu |
| 6,649,368 B1 | 11/2003 | Aghassi et al. |
| 6,673,620 B1 | 1/2004 | Loeffler et al. |
| 6,678,577 B1 | 1/2004 | Stylli et al. |
| 6,719,449 B1 | 4/2004 | Laugharn, Jr. et al. |
| D495,425 S | 8/2004 | Goris et al. |
| 6,773,676 B2 | 8/2004 | Schembri |
| 6,783,733 B2 | 8/2004 | Bogen et al. |
| 6,827,901 B2 | 12/2004 | Copeland et al. |
| 6,855,292 B2 | 2/2005 | Angros |
| 6,855,559 B1 | 2/2005 | Christensen et al. |
| 6,930,292 B1 | 8/2005 | Winther et al. |
| 6,943,029 B2 | 9/2005 | Copeland et al. |
| 6,943,035 B1 | 9/2005 | Davies et al. |
| 6,948,843 B2 | 9/2005 | Laugharn, Jr. et al. |
| 7,025,933 B2 | 4/2006 | Ganz et al. |
| 7,250,301 B2 | 7/2007 | Angros |
| 7,270,785 B1 | 9/2007 | Lemme et al. |
| 7,318,913 B2 | 1/2008 | Loeffler et al. |
| 7,378,055 B2 | 5/2008 | Lemme et al. |
| 7,378,058 B2 | 5/2008 | Lemme et al. |
| 7,400,983 B2 | 7/2008 | Feingold et al. |
| 7,476,362 B2 | 1/2009 | Angros |
| 7,584,019 B2 | 9/2009 | Feingold et al. |
| 7,622,077 B2 | 11/2009 | Angros |
| 7,632,461 B2 | 12/2009 | Angros |
| 7,648,678 B2 | 1/2010 | Favuzzi et al. |
| 7,850,912 B2 | 12/2010 | Favuzzi et al. |
| 7,867,443 B2 | 1/2011 | Key et al. |
| 7,875,242 B2 | 1/2011 | Shah |
| 7,875,245 B2 | 1/2011 | Favuzzi et al. |
| 7,897,106 B2 | 3/2011 | Angros et al. |
| 8,007,720 B2 | 8/2011 | Angros |
| 8,007,721 B2 | 8/2011 | Angros |
| 8,052,927 B2 | 11/2011 | Angros |
| 8,071,023 B2 | 12/2011 | Angros |
| 8,092,742 B2 | 1/2012 | Angros |
| 8,361,388 B2 * | 1/2013 | Angros ............... B01L 7/00 422/64 |
| 8,377,377 B2 * | 2/2013 | Angros ............... B01L 3/0293 422/64 |
| 8,486,335 B2 * | 7/2013 | Angros ............... B01L 3/0293 422/63 |
| 9,267,868 B2 * | 2/2016 | Angros ............... B01L 3/0293 |
| 2003/0022391 A1 | 1/2003 | Richards et al. |
| 2003/0124729 A1 | 7/2003 | Christensen et al. |
| 2003/0203493 A1 | 10/2003 | Lemme et al. |
| 2003/0211630 A1 | 11/2003 | Richards et al. |
| 2004/0002163 A1 | 1/2004 | Reinhardt et al. |
| 2004/0029184 A1 | 2/2004 | Gourevitch |
| 2005/0227298 A1 | 10/2005 | Gourevitch |
| 2006/0188396 A1 | 8/2006 | Bedingham et al. |
| 2006/0275861 A1 | 12/2006 | Angros et al. |
| 2006/0275889 A1 | 12/2006 | Angros et al. |
| 2006/0281116 A1 | 12/2006 | Angros et al. |

FOREIGN PATENT DOCUMENTS

| | | |
|---|---|---|
| WO | 00/18686 | 11/2000 |
| WO | 01/07890 | 2/2001 |
| WO | 2004/059284 | 7/2004 |
| WO | 2006/127852 | 11/2006 |
| WO | 2009/055451 | 10/2009 |

OTHER PUBLICATIONS

U.S. Appl. No. 60/142,789, filed Jul. 8, 1999, Angros.
U.S. Appl. No. 60/375,679, filed Apr. 26, 2002, Ventana.
International Search Report and Written Opinion (PCT/US2009/55451); Oct. 15, 2009.
"Automated Systems" Brochure, BioGenex 2000.
"Dako® Autostainer Universal Staining System," Brochure, DAKO Corporation, 1999.
"Declere™, One Giant Step Towards Standardization of IHC," Brochure, Cell Marque, 1999.
"Expanding the Power of NexESz®", Ventana Brochure, 1998.
"Mark 5 HSS" Promotional Release and Flyer, Diagnostic Products Corporation, 1999.
"MISHA™" Catalog pp. 2-3, Shandon Lipshaw, 1997.
"One Platform. Infinite Possibilities™," Artisan Staining System Brochure, CytoLogix Corporation, 1999.
Pileri et al., "Antigen Retrieval Techniques in Immunohistochemistry: Comparison of Different Methods," Journal of Pathology, 1997, vol. 183:116-123.
"PROTOCOL™ MicroProbe® Staining System for Immunohistochemistry and Special Stains," Fisher Healthcare Brochure, 1998.
Shi et al., "Antigen Retrieval Immunohistochemistry: Past, Present, and Future," J. of Histochemistry & Cytochemistry, 45(3): 327-343, 1997.
Shi et al., "Development of an Optimal Protocol for Antigen Retrieval: A 'Test Batter' Approach Exemplified with Reference to the Staining of Retinoblastoma Protein (pRB) in Formalin-Fixed Paraffin Sections," J. of Pathology, 179:347-352, 1996.
Shi et al., "Use of pH 9.5 Tris-HCI Buffer Containing 5% Urea for Antigen Retrieval Immunohistochemistry," Biotechnic & Histochemistry, 71(4):190-195, 1996.
Taylor et al., "Comparative Study of Antigen Retrieval Heating Methods: Microwave, Microwave and Pressure cooker, Autoclave and Steamer," Biotechnic & Histochemistry, 71(5):263-270, 1996.
"TST Stainer Trio" Brochure, Mopec™,—dated prior to 1998.
"Walker-Away Automation for Special Stains and IHC" Brochure, CytoLogix Corporation,—dated prior to 1998.
"Zymed®" Immunohistopathology Catalog, Zymed Laboratories Inc., 1998-1999.
U.S. Appl. No. 09/612,605, Angros, Office Action Restriction dated Sep. 25, 2001.
U.S. Appl. No. 09/612,605, Angros, Response to Office Action Restriction filed Oct. 12, 2001.
U.S. Appl. No. 09/612,605, Angros, Notice of Allowance dated Jun. 10, 2002.
U.S. Appl. No. 09/612,605, Angros, Communication dated Jul. 12, 2002.
U.S. Appl. No. 10/245,035, Angros, Office Action Restriction dated Jan. 28, 2004.

(56) References Cited

OTHER PUBLICATIONS

U.S. Appl. No. 10/245,035, Angros, Response to Office Action Restriction filed Apr. 28, 2004.
U.S. Appl. No. 10/245,035, Angros, Office Action Restriction dated Jul. 27, 2004.
U.S. Appl. No. 10/245,035, Angros, Response to Office Action Restriction filed Sep. 17, 2004.
U.S. Appl. No. 10/245,035, Angros, Supplemental Preliminary Amendment filed Nov. 10, 2004.
U.S. Appl. No. 10/245,035, Angros, Office Action dated Jan. 26, 2005.
U.S. Appl. No. 10/245,035, Angros, Response to Office Action filed May 24, 2005.
U.S. Appl. No. 10/245,035, Angros, Supplemental Amendment filed Aug. 2, 2005.
U.S. Appl. No. 10/245,035, Angros, Final Office Action dated Jan. 19, 2006.
U.S. Appl. No. 10/245,035, Angros, Amendment and Request for Continued Exam filed Jun. 7, 2006.
U.S. Appl. No. 10/245,035, Angros, Supplemental Amendment filed Aug. 3, 2006.
U.S. Appl. No. 10/245,035, Angros, Second Supplemental Amendment filed Sep. 27, 2006.
U.S. Appl. No. 10/245,035, Angros, Third Supplemental Amendment filed Dec. 8, 2006.
U.S. Appl. No. 10/245,035, Angros, Interview Summary dated Jan. 11, 2007.
U.S. Appl. No. 10/245,035, Angros, Response to Interview Summary filed Jan. 29, 2007.
U.S. Appl. No. 10/245,035, Angros, Notice of Allowance dated Mar. 15, 2007.
U.S. Appl. No. 10/388,710, Angros, Office Action dated Mar. 18, 2004.
U.S. Appl. No. 10/388,710, Angros, Response to Office Action filed May 6, 2004.
U.S. Appl. No. 10/388,710, Angros, Notice of Allowance dated Jun. 15, 2004.
U.S. Appl. No. 10/388,710, Angros, Amendment after allowance dated Aug. 27, 2004.
U.S. Appl. No. 10/943,386, Angros, Office Action Restriction dated Apr. 9, 2007.
U.S. Appl. No. 10/943,386, Angros, Response to Election and Amendment filed Jul. 9, 2007.
U.S. Appl. No. 10/943,386, Angros, Second Preliminary Amendment filed Sep. 5, 2007.
U.S. Appl. No. 101943,386, Angros, Office Action dated Nov. 1, 2007.
U.S. Appl. No. 10/943,386, Angros, Response to Office Action filed Nov. 19, 2007.
U.S. Appl. No. 10/943,386, Angros, Office Action dated Feb. 22, 2008.
U.S. Appl. No. 10/943,386, Angros, Response to Office Action filed May 30, 2008.
U.S. Appl. No. 10/943,386, Angros, Second Amendment and Response to Office Action filed Aug. 15, 2008.
U.S. Appl. No. 10/943,386, Angros, Office Action Restriction dated Apr. 27, 2009.
U.S. Appl. No. 10/943,386, Angros, Amendment and Response to Office Action filed Jun. 26, 2009.
U.S. Appl. No. 10/943,386, Angros, Final Office Action dated Oct. 1, 2009.
U.S. Appl. No. 10/943,386, Angros, Notice of Allowance dated Oct. 2, 2009.
U.S. Appl. No. 10/943,386, Angros, Comments on Notice of Allowance dated Oct. 14, 2009.
U.S. Appl. No. 10/943,394, Angros, Office Action Restriction dated Apr. 9, 2007.
U.S. Appl. No. 10/943,394, Angros, Response to Office Action Restriction filed Jul. 9, 2007.
U.S. Appl. No. 10/943,394, Angros, Second Preliminary Amendment filed Sep. 5, 2007.
U.S. Appl. No. 10/943,394, Angros, Office Action dated Oct. 10, 2007.
U.S. Appl. No. 10/943,394, Angros, Response to Office Action filed Oct. 25, 2007.
U.S. Appl. No. 10/943,394, Angros, Office Action dated Feb. 22, 2008.
U.S. Appl. No. 10/943,394, Angros, Examiner Interview dated May 8, 2008.
U.S. Appl. No. 10/943,394, Angros, Response to Office Action filed May 30, 2008.
U.S. Appl. No. 10/943,394, Angros, Second Amendment and Response to Office Action filed Aug. 14, 2008.
U.S. Appl. No. 10/943,394, Angros, Third Amendment and Response to Office Action filed Aug. 18, 2008.
U.S. Appl. No. 10/943,394, Angros, Office Action Restriction dated Apr. 27, 2009.
U.S. Appl. No. 10/943,394, Angros, Amendment and Response to Office Action filed Jun. 26, 2009.
U.S. Appl. No. 10/943,394, Angros, Submission of Terminal Disclaimer filed Sep. 15, 2009.
U.S. Appl. No. 10/943,394, Angros, Final Office Action dated Sep. 16, 2009.
U.S. Appl. No. 10/943,394, Angros, Submission of Terminal Disclaimer in Response to Final Office Action filed Sep. 16, 2009.
U.S. Appl. No. 10/943,394, Angros, Notice of Allowance dated Oct. 6, 2009.
U.S. Appl. No. 10/943,394, Angros, Amendment and Comments of Notice of Allowance dated Oct. 14, 2009.
U.S. Appl. No. 10/943,546, Angros, Office Action dated Aug. 27, 2007.
U.S. Appl. No. 10/943,546, Angros, Amendment and Response to Office Action filed Feb. 27, 2008.
U.S. Appl. No. 10/943,546, Angros, Interview Summary Mar. 4, 2008.
U.S. Appl. No. 10/943,546, Angros, Notice of Non-Compliance dated Mar. 10, 2008.
U.S. Appl. No. 10/943,546, Angros, Notice of Allowance dated Mar. 18, 2008.
U.S. Appl. No. 10/943,546, Angros, Response to Interview Summary and Response to Notice of Non-Compliance filed Mar. 26, 2008 (mis-dated Feb. 27, 2008).
U.S. Appl. No. 10/943,546, Angros, Request for Continued Examination and Request for Withdrawal of Issuance filed Aug. 15, 2008.
U.S. Appl. No. 10/943,546, Angros, Notice of Allowance dated Aug. 29, 2008.
U.S. Appl. No. 10/943,546, Angros, Amendment and Request for Continued Examination filed Sep. 9, 2008.
U.S. Appl. No. 10/943,546, Angros, Notice of Allowance dated Sep. 22, 2008.
U.S. Appl. No. 11/439,722, Angros et al., Preliminary Amendment, Nov. 13, 2007.
U.S. Appl. No. 11/439,722, Angros et al., Office Action dated Apr. 15, 2008.
U.S. Appl. No. 11/439,722, Angros et al., Amendment and Response to Office Action, Oct. 13, 2008.
U.S. Appl. No. 11/439,722, Angros, et al., Office Action Restriction dated Oct. 6, 2009.
U.S. Appl. No. 11/439,722, Angros et al., Amendment and Response to Office Action Restriction dated Apr. 6, 2010.
U.S. Appl. No. 11/439,722, Angros, et al., Final Office Action dated Jul. 7, 2010.
U.S. Appl. No. 11/439,722, Angros et al., Amendment and Response dated Aug. 4, 2010.
U.S. Appl. No. 11/439,722, Angros et al., Notice of Allowance dated Aug. 27, 2010.
U.S. Appl. No. 11/439,722, Angros, et al., 312 Amendment filed Nov. 15, 2010.
U.S. Appl. No. 11/439,722, Angros et al., Second 312 Amendment filed Nov. 29, 2010.
U.S. Appl. No. 11/439,722, Angros et al., PTO Response to 312 Communication, mailed Dec. 6, 2010.

(56) References Cited

OTHER PUBLICATIONS

U.S. Appl. No. 11/439,722, Angros et al., PTO Response to Second 312 Communication, mailed Jan. 28, 2011.
U.S. Appl. No. 11/439,834, Angros et al., Preliminary Amendment, Nov. 13, 2007.
U.S. Appl. No. 11/439,834, Angros et al., Office Action dated Jan. 23, 2009.
U.S. Appl. No. 11/439,834, Angros et al., Amendment and Response dated Jun. 22, 2009.
U.S. Appl. No. 11/439,834, Angros et al., Office Action Restriction dated Oct. 15, 2009.
U.S. Appl. No. 11/439,834, Angros et al., Amendment and Response to Restriction Requirement dated Apr. 16, 2010.
U.S. Appl. No. 11/439,834, Angros et al., Supplemental Amendment and Response dated Sep. 28, 2010.
U.S. Appl. No. 11/439,834, Angros et al., Final Office Action dated Dec. 7, 2010.
U.S. Appl. No. 11/439,834, Angros et al., Response dated Dec. 28, 2010.
U.S. Appl. No. 11/439,834, Angros et al., PTO Advisory Action dated Jan. 13, 2011.
U.S. Appl. No. 11/439,834, Angros et al., Amendment and Response under 1.116 filed Feb. 8, 2011.
U.S. Appl. No. 11/439,834, Angros et al., PTO Notice of Allowance dated Mar. 17, 2011.
U.S. Appl. No. 11/440,312, Angros et al., Preliminary Amendment, Nov. 13, 2007.
U.S. Appl. No. 11/440,312, Angros et al., Office Action Restriction dated Apr. 2, 2009.
U.S. Appl. No. 11/440,312, Angros et al., Amendment and Response to Election dated Jul. 2, 2009.
U.S. Appl. No. 11/440,312, Angros et al., Office Action dated Oct. 27, 2009.
U.S. Appl. No. 11/440,312, Angros et al., Amendment and Response dated Apr. 21, 2010.
U.S. Appl. No. 11/440,312, Angros et al., Office Action dated Aug. 17, 2010.
U.S. Appl. No. 11/440,312, Angros et al., Response dated Dec. 15, 2010.
U.S. Appl. No. 11/440,312, Angros et al., Final Office Action dated Feb. 25, 2011.
U.S. Appl. No. 11/440,312, Amendment and Response filed Apr. 20, 2011.
U.S. Appl. No. 11/807,841, Angros et al., Amendment and Response dated Aug. 4, 2010.
U.S. Appl. No. 11/440,312, Angros et al., Notice of Allowance dated Jul. 13, 2012.
U.S. Appl. No. 11/807,841, Angros, Preliminary Amendment dated Nov. 13, 2007.
U.S. Appl. No. 11/807,841, Angros, Preliminary Amendment dated Aug. 29, 2008.
U.S. Appl. No. 11/807,841, Angros, Office Action Restriction dated Oct. 20, 2008.
U.S. Appl. No. 11/807,841, Angros, Response to Office Action Restriction filed Dec. 18, 2008.
U.S. Appl. No. 11/807,841, Angros, Office Action dated Mar. 30, 2009.
U.S. Appl. No. 11/807,841, Angros, Express Abandonment, filed Jun. 30, 2009.
Japanese Application No. 2008-513689, Angros et al., Office Action mailed Jul. 9, 2011.
Mexican Application No. MX/a/2007/014655, Angros et al., Response to Office Action filed Jul. 16, 2011.
Mexican Application No. MX/a/2007/014655, Angros et al., Office Action mailed Aug. 14, 2011.
Russian Application No. 2007146930, Angros et al., Request to Issue, dated Jul. 6, 2011.
EP 00947135.0, Angros, Voluntary Amendment Apr. 15, 2002.
EP 00947135.0, Angros, Office Action Jan. 19, 2006.
EP 00947135.0, Angros, Response to Office Action Jul. 28, 2006.
EP 00947135.0, Angros, Office Action Aug. 23, 2006.
EP 00947135.0, Angros, Response to Office Action Nov. 22, 2007.
EP 00947135.0, Angros, Office Action Jun. 14, 2007.
EP 00947135.0, Angros, EP Notice Jan. 28, 2008.
EP 00947135.0, Angros, Response to Office Action and Notice Apr. 24, 2008.
EP 00947135.0, Angros, Second Amendment May 20, 2008.
EP 00947135.0, Angros, Office Action Jun. 19, 2008.
EP 00947135.0, Angros, Response to Office Action Dec. 24, 2008.
EP 00947135.0, Angros, Office Action Jan. 19, 2011.
EP 00947135.0, Angros, Response to Office Action Jul. 19, 2011.
CA 2,379,410, Angros, Office Action Apr. 2, 2008.
CA 2,379,410, Angros, Response to Office Action Oct. 2, 2008.
CA 2,379,410, Angros, Office Action Mar. 12, 2009.
CA 2,379,410, Angros, Response to Office Action Sep. 14, 2009.
CA 2,379,410, Angros, Office Action Jun. 27, 2011.
U.S. Appl. No. 12/198,692, Angros, Office Action dated Dec. 24, 2009.
U.S. Appl. No. 12/198,692, Angros, Amendment and Response filed Jun. 24, 2010.
U.S. Appl. No. 12/198,692, Angros, Final Office Action dated Sep. 9, 2010.
U.S. Appl. No. 12/198,692, Angros, Interview Summary dated Jan. 21, 2011.
U.S. Appl. No. 12/198,692, Angros, Amendment and Response and Request for Continued Examination filed Jan. 28, 2011.
U.S. Appl. No. 12/198,692, Angros, Response to Interview Summary filed Feb. 8, 2011.
U.S. Appl. No. 12/198,692, Angros, Office Action dated Mar. 18, 2011.
U.S. Appl. No. 12/198,692, Angros, Amendment and Response, filed Apr. 18, 2011.
U.S. Appl. No. 12/198,692, Angros, Notice of Allowance, mailed Jun. 6, 2011.
U.S. Appl. No. 12/561,568, Angros, Office Action dated Jan. 5, 2010.
U.S. Appl. No. 12/561,568, Angros, Amendment and Response filed Jun. 24, 2010.
U.S. Appl. No. 12/561,568, Angros, Supplemental Amendment and Response filed Jun. 25, 2010.
U.S. Appl. No. 12/561,568, Angros, Office Action dated Aug. 25, 2010.
U.S. Appl. No. 12/561,568, Angros, Amendment and Response and Request for Continued Examination filed Feb. 24, 2011.
U.S. Appl. No. 12/561,568, Angros, Office Action dated Mar. 10, 2011.
U.S. Appl. No. 12/561,568, Angros, Amendment and Response, filed Apr. 18, 2011.
U.S. Appl. No. 12/561,568, Angros, Notice of Allowance, mailed Jun. 2, 2011.
U.S. Appl. No. 12/495,152, Angros, Preliminary Amendment filed Jul. 16, 2009.
U.S. Appl. No. 12/495,152, Angros, Office Action dated Jan. 14, 2011.
U.S. Appl. No. 12/495,152, Angros, Amendment and Response, filed May 10, 2011.
U.S. Appl. No. 12/495,152, Angros, Notice of Allowance, mailed Jul. 18, 2011.
U.S. Appl. No. 12/495,152, Angros, 312 Amendment, filed Sep. 13, 2011.
U.S. Appl. No. 12/495,152, Angros, Response to Rule 312 Communication, mailed Sep. 22, 2011.
U.S. Appl. No. 12/624,097, Angros, Office Action dated Oct. 4, 2010.
U.S. Appl. No. 12/624,097, Angros, Amendment and Response, filed Apr. 4, 2011.
U.S. Appl. No. 12/624,097, Angros, Office Action dated Aug. 31, 2011.
U.S. Appl. No. 12/624,097, Angros, Response and Amendment, filed Sep. 23, 2011.
U.S. Appl. No. 12/624,097, Angros, Notice of Allowance, mailed Nov. 29, 2011.

(56) References Cited

OTHER PUBLICATIONS

U.S. Appl. No. 12/624,120, Angros, Office Action dated Oct. 1, 2010.
U.S. Appl. No. 12/624,120, Angros, Amendment and Response filed Mar. 29, 2011.
U.S. Appl. No. 12/624,120, Angros, Office Action Aug. 15, 2011.
U.S. Appl. No. 12/624,120, Angros, Response to Final Action Under 37 CFR 1.116, filed Aug. 26, 2011.
U.S. Appl. No. 12/624,120, Angros, Further Remarks in Response to the Final Office Acton, filed Sep. 2, 2011.
U.S. Appl. No. 12/624,120, Angros, Notice of Allowance, mailed Oct. 6, 2011.
U.S. Appl. no. 12/550,288, Angros, Response to Office Action filed Jul. 27, 2012.
U.S. Appl. No. 12/550,288, Angros, Notice of Allowance dated Oct. 11, 2012.
U.S. Appl. No. 12/550,288, Angros, PTO Communication dated Dec. 5, 2012.
U.S. Appl. No. 12/550,288, Angros, Preliminary Amendment, filed Nov. 25, 2009.
U.S. Appl. No. 12/550,288, Angros, Office Action Restriction dated Mar. 27, 2012.
U.S. Appl. No. 13/036,873, Angros, Notice of Allowance dated Sep. 24, 2012.
U.S. Appl. No. 13/117,941, Angros, Final Office Action dated Nov. 8, 2012.
U.S. Appl. No. 13/220,438, Angros, Notice of Allowance dated Jul. 25, 2012.
U.S. Appl. No. 13/220,438, Angros, Interview Summary dated Aug. 1, 2012.
U.S. Appl. No. 13/220,438, Angros, 1.312 Amendment filed Sep. 27, 2012.
U.S. Appl. No. 13/220,438, Angros, PTO Communication dated Oct. 2, 2012.
U.S. Appl. No. 13/220,454, Angros, Interview Summary dated Aug. 2, 2012.
U.S. Appl. No. 13/220,454, Angros, Notice of Allowance dated Aug. 6, 2012.
U.S. Appl. No. 13/220,454, Angros, 1.312 Amendment filed Sep. 27, 2012.
U.S. Appl. No. 13/220,454, Angros, PTO Communication dated Oct. 11, 2012.
U.S. Appl. No. 13/311,066, Angros, Notice of Allowance Sep. 21, 2012.
Canadian Application No. 2,609,453, Angros, Response filed Oct. 26, 2012.
Chinese Application No. 200680026673.8, Angros, Office Action dated Jun. 14, 2012.
Chinese Application No. 200680026673.8, Angros, Response filed Oct. 25, 2012.
Chinese Application No. 200680026673.8, Angros, Office Action dated Nov. 8, 2012.
Chinese Application No. 200680026673.8, Angros, Response filed Nov. 12, 2012.
Japanese Application No. 2008-513689, Angros, Response filed Nov. 8, 2012.
Canadian Application No. 2,379,410, Angros, Office Action dated Oct. 12, 2012.
United Kingdom Application No. 1105321.2, Angros, Office Action dated Jul. 18, 2012.
United Kingdom Application No. 1105321.2, Angros, Response filed Nov. 15, 2012.
United Kingdom Application No. 1105321.2, Angros, Office Action dated Nov. 23, 2012.
Australian U.S. Appl. No. 2006249956, Angros et al., Voluntary Amendment dated Nov. 23, 2009.
Australian U.S. Appl. No. 2006249956, Angros et al., Office Action dated Feb. 24, 2011.
Brazilian Application No. 060989-3, Angros et al., Voluntary Amendment dated May 18, 2009.
Canadian Application No. 2,609,453, Angros et al., Voluntary Amendment dated Dec. 9, 2009.
Chinese Application No. 200680026673.8, Angros et al., Voluntary Amendment dated Nov. 30, 2009.
Chinese Application No. 200680026673.8, Angros et al., Office Action dated Feb. 12, 2010.
Chinese Application No. 200680026673.8, Angros et al., Response to Office Action dated Aug. 27, 2010.
Chinese Application No. 200680026673.8, Angros et al., Office Action dated Nov. 24, 2010.
Chinese Application No. 200680026673.8, Angros et al., Amendment and Response filed Apr. 11, 2011.
European Application No. 06771115.0, Angros et al., Voluntary Amendment dated Jan. 20, 2010.
Indian Application No. 9149/DELNP/2007, Angros et al., Voluntary Amendment dated May 19, 2009.
Japanese Application No. 2008-513689, Angros et al., Voluntary Amendment dated May 22, 2009.
Mexican Application No. MX/a/2007/014655, Angros et al., Voluntary Amendment dated Feb. 16, 2010.
Mexican Application No. MX/a/2007/014655, Angros et al., Office Action dated Mar. 28, 2011.
Russian Application No. 2007146930, Angros et al., Voluntary Amendment dated May 25, 2009.
Russian Application No. 2007146930, Angros et al., Office Action dated May 6, 2010.
Russian Application No. 2007146930, Angros et al., Response to Office Action dated Sep. 17, 2010.
Russian Application No. 2007146930, Angros et al., Office Action dated Nov. 29, 2010.
Russian Application No. 200714930, Angros et al., Amended Claims filed in Response Jan. 18, 2011.
Canadian Application No. 2,609,453, Angros et al., Office Action dated Apr. 30, 2012.
Chinese Application No. 200680026673.8, Angros et al., Office Action dated Aug. 10, 2011.
Chinese Application No. 200680026673.8, Angros et al., Response to Office Action dated Dec. 25, 2011.
European Application No. 06771115.0, Angros et al., Office Action dated Feb. 28, 2012.
European Application No. 067711115.0, Angros et al., Response to Office Action dated Apr. 25, 2012.
European Application No. 06771115.0, Angros et al., Office Action dated Jul. 13, 2012.
Japanese Application No. 2008-513689, Angros et al., Response to Office Action Jan. 12, 2012.
Japanese Application No. 2008-513689, Angros et al., Office Action dated Mar. 8, 2012.
Mexican Application No. MX/a/2007/014655, Angros et al., Response to Office Action dated Dec. 17, 2011.
Mexican Application No. MX/a/2007/014655, Angros et al., Allowance dated Jan. 9, 2012.
Canadian Application No. 2,379,410, Angros, Response to Office Action dated Dec. 12, 2011.
U.S. Appl. No. 12/550,296, Angros, Preliminary Amendment, filed Nov. 25, 2009.
U.S. Appl. No. 12/550,296, Angros, Preliminary Amendment filed Dec. 11, 2009.
U.S. Appl. No. 12/550,296, Angros, Office Action Restriction dated Apr. 24, 2012.
U.S. Appl. No. 12/550,296, Angros, Response to Office Action Restriction filed Jul. 24, 2012.
U.S. Appl. No. 12/550,296, Angros, Notice of Allowance dated Oct. 5, 2012.
U.S. Appl. No. 13/036,873, Angros, Preliminary Amendment, filed Mar. 4, 2011.
U.S. Appl. No. 13/036,873, Angros, Office Action dated Feb. 28, 2012.
U.S. Appl. No. 13/117,971, Angros, Office Action dated Dec. 13, 2011.
U.S. Appl. No. 13/117,971, Angros, Response to Office Action fired Jun. 12, 2012.

(56) References Cited

OTHER PUBLICATIONS

U.S. Appl. No. 13/220,438, Angros, Office Action dated Feb. 21, 2012.
U.S. Appl. No. 13/220,438, Angros, Response to Office Action, mailed Jul. 20, 2012.
U.S. Appl. No. 13/220,454, Angros, Notice of Allowance dated Sep. 21, 2012.
U.S. Appl. No. 13/220,454, Angros, Office Action dated Feb. 28, 2012.
U.S. Appl. No. 13/220,454, Angros, Response to Office Action Jul. 20, 2012.
U.S. Appl. No. 13/311,066, Angros, Office Action dated Mar. 28, 2012.
U.S. Appl. No. 13/311,066, Angros, Response to Office Action mailed Jul. 20, 2012.
Australian Application No. 2009 285551, Angros, Voluntary Amendment filed Mar. 29, 2011.
United Kingdom Application No. 1105321.2, Angros, Voluntary Amendment filed Apr. 4, 2011.
United Kingdom Application No. 1105321.2, Angros, Office Action Jan. 30, 2012.
United Kingdom Application No. 1105321.2, Angros, Response to Office Action May 30, 2012.
United Kingdom Application No. 1105321.2, Angros, Supplemental Response to Office Action dated Jun. 25, 2012.

* cited by examiner

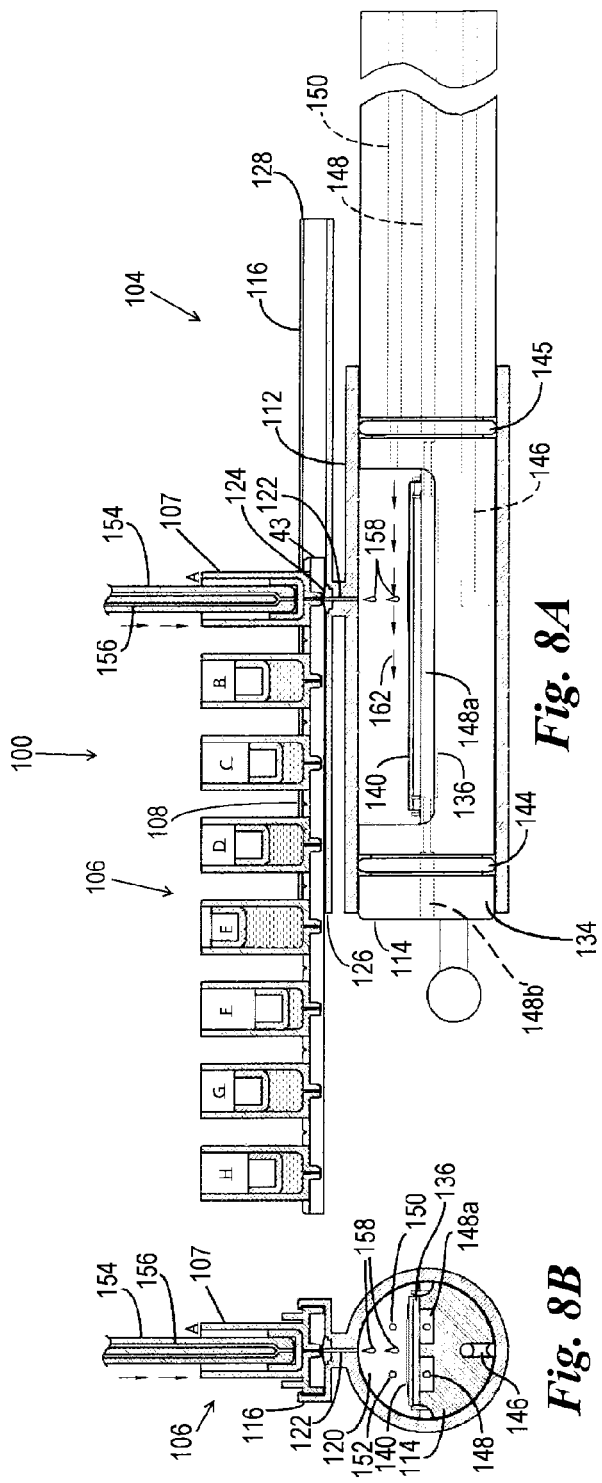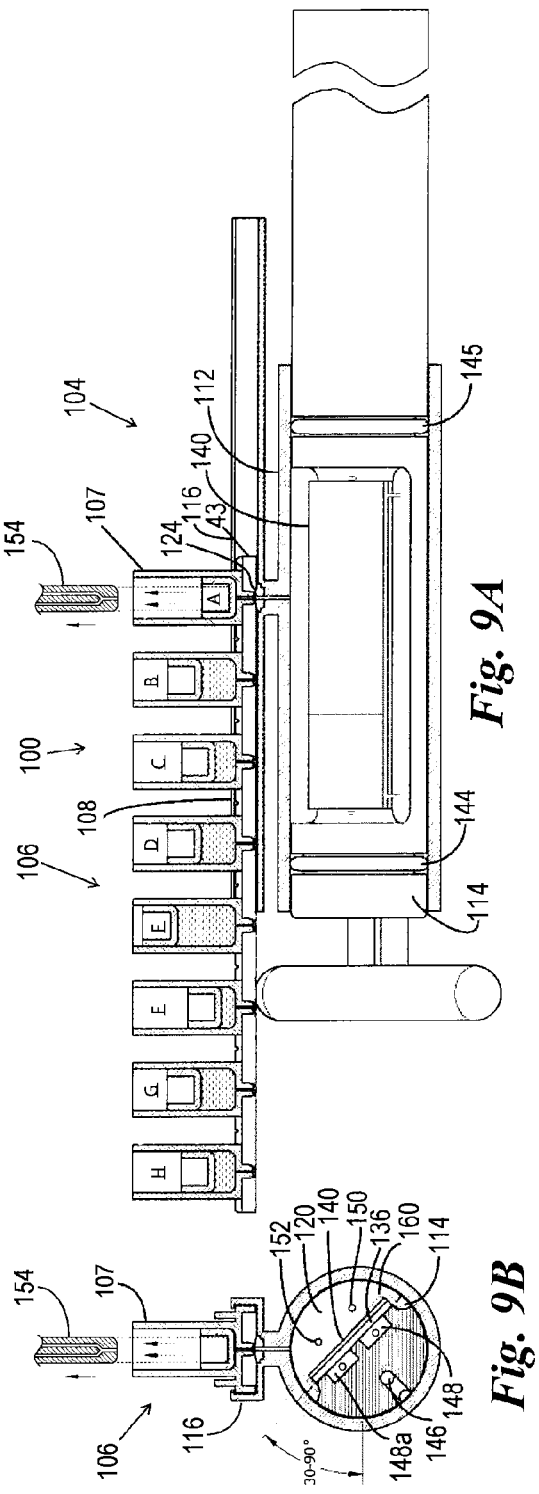

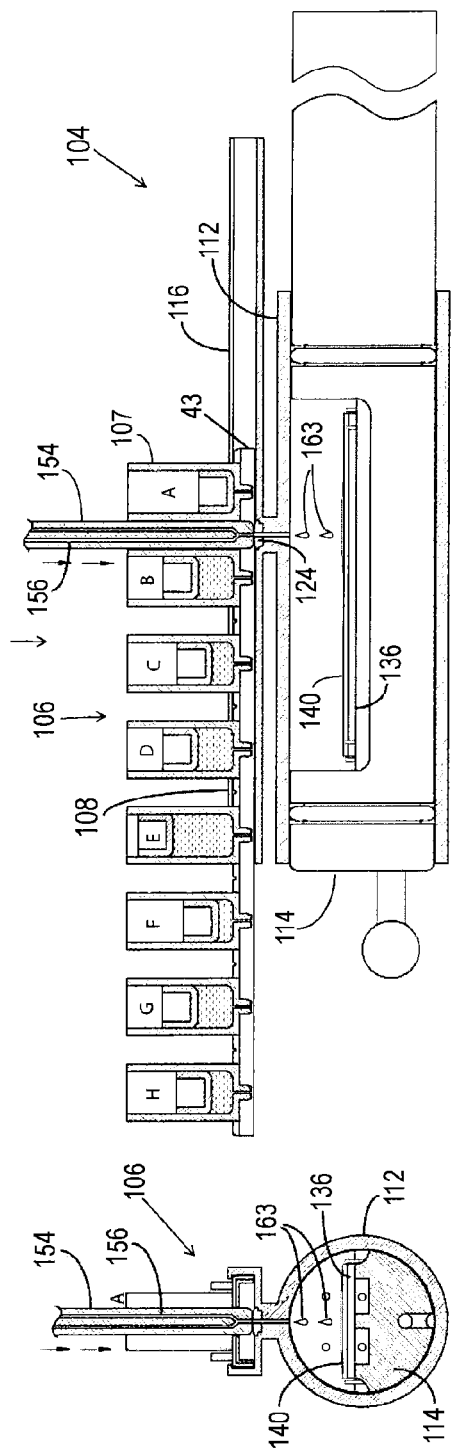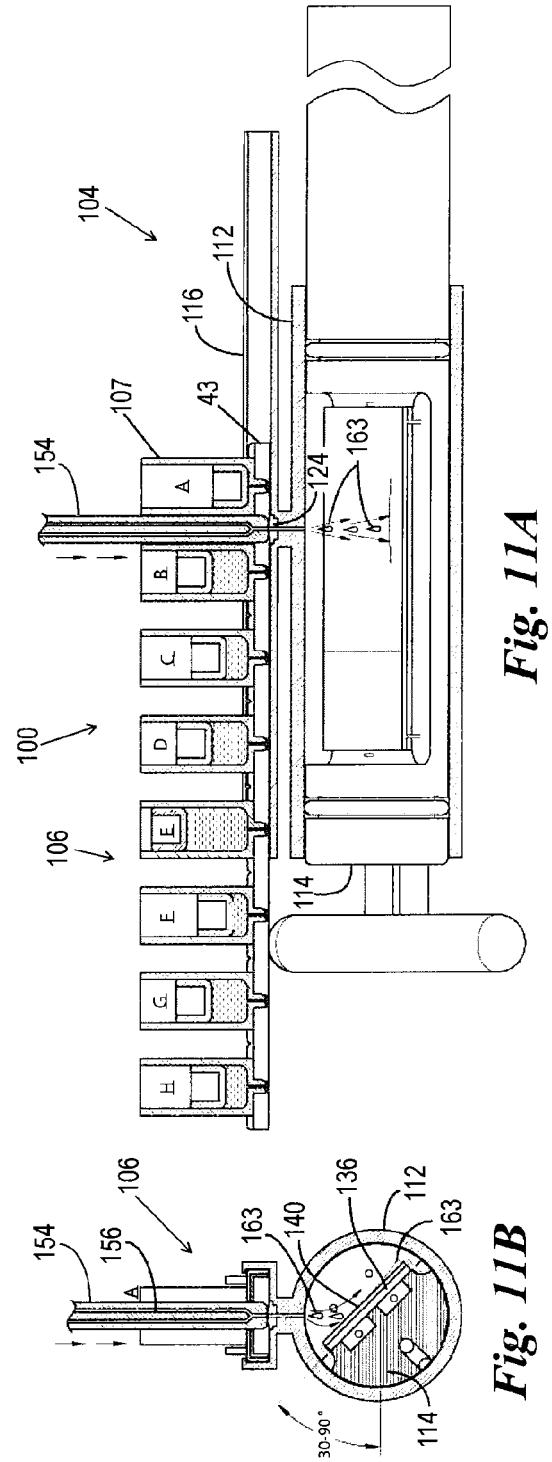

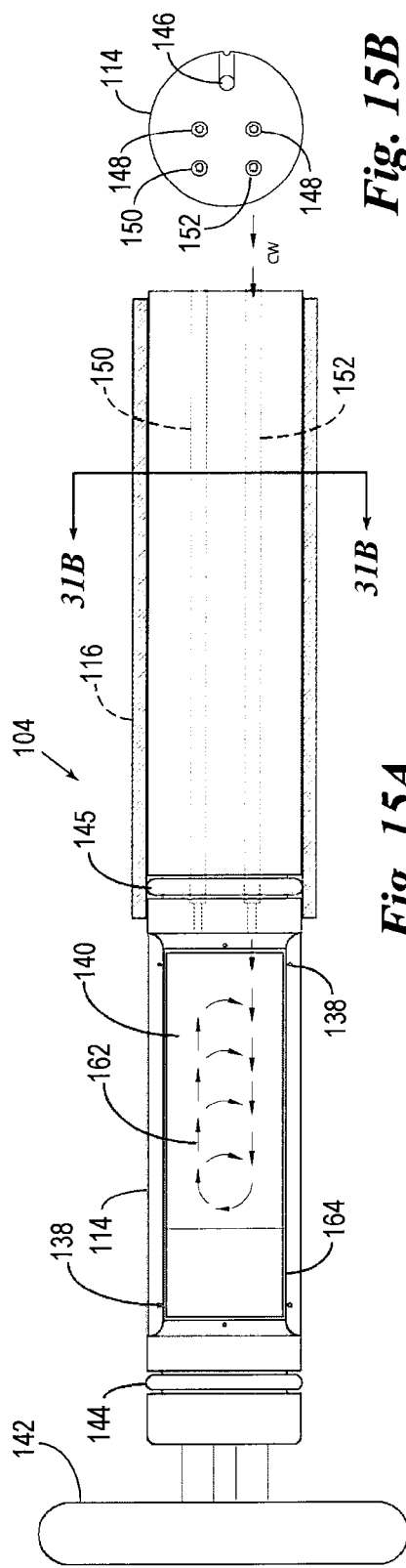
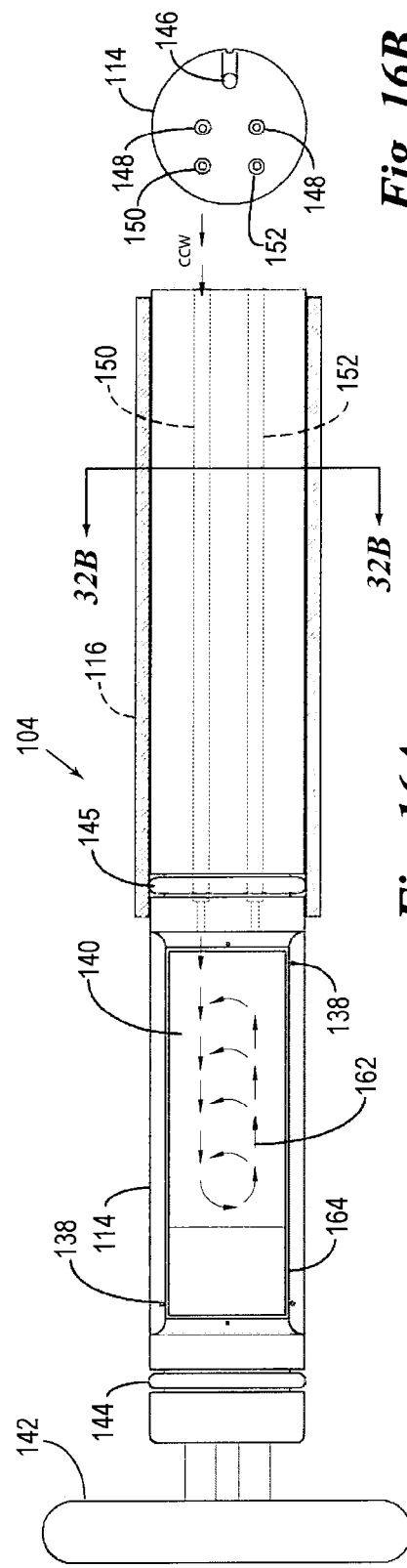

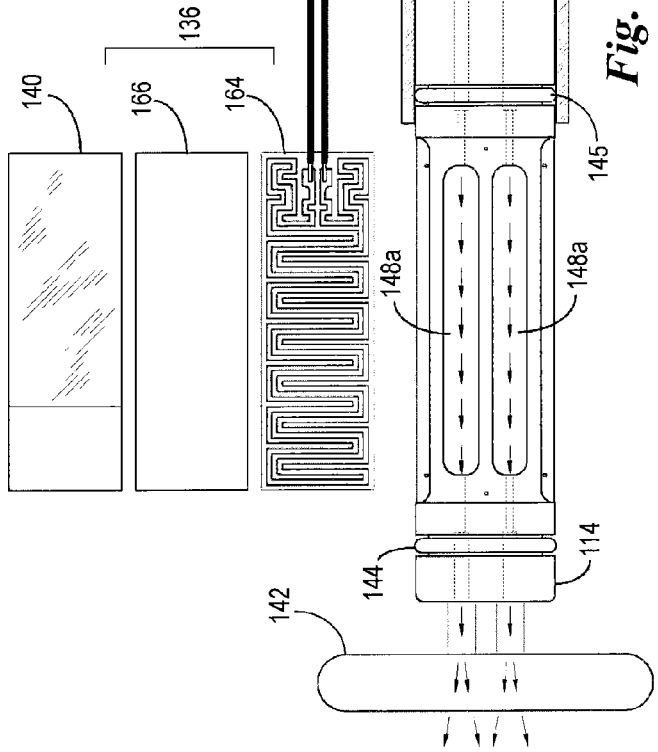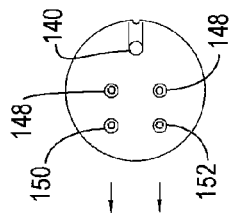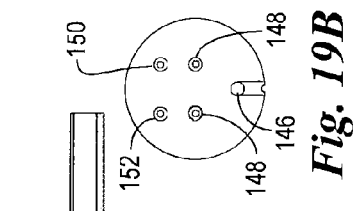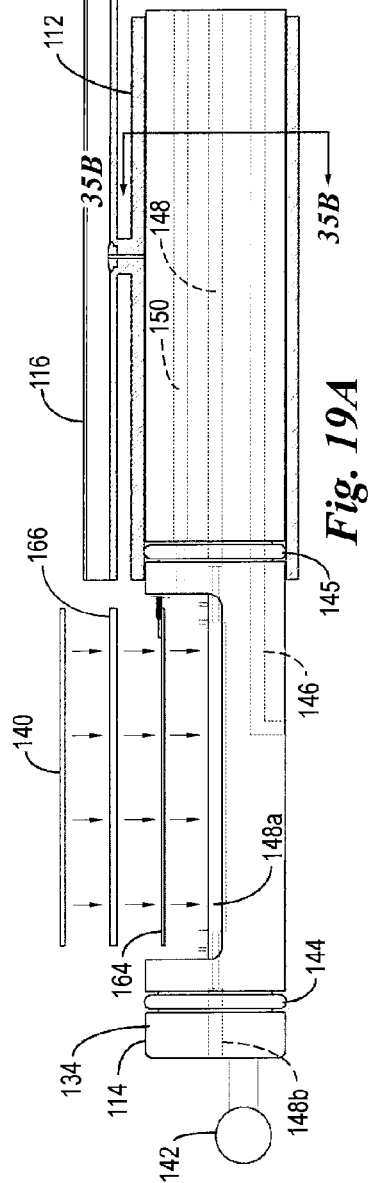

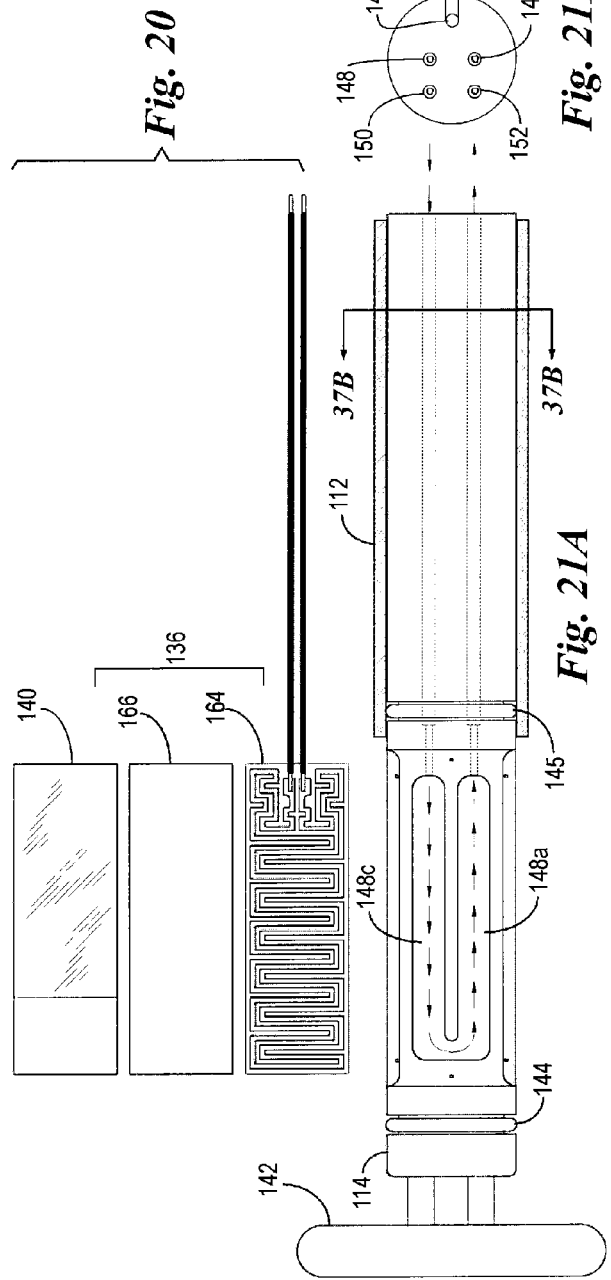

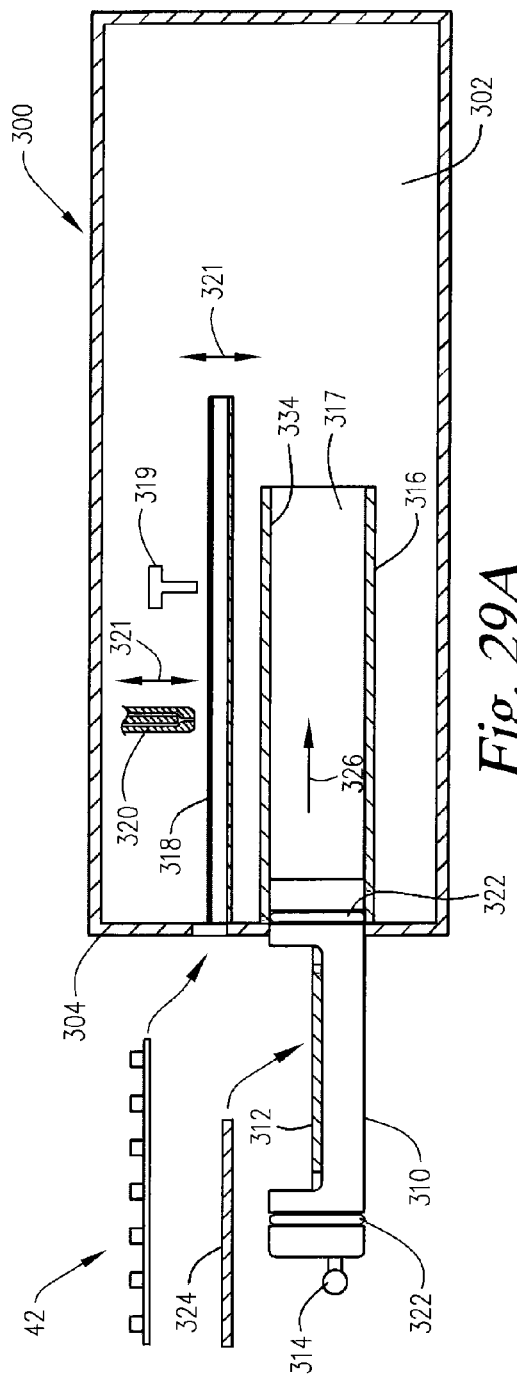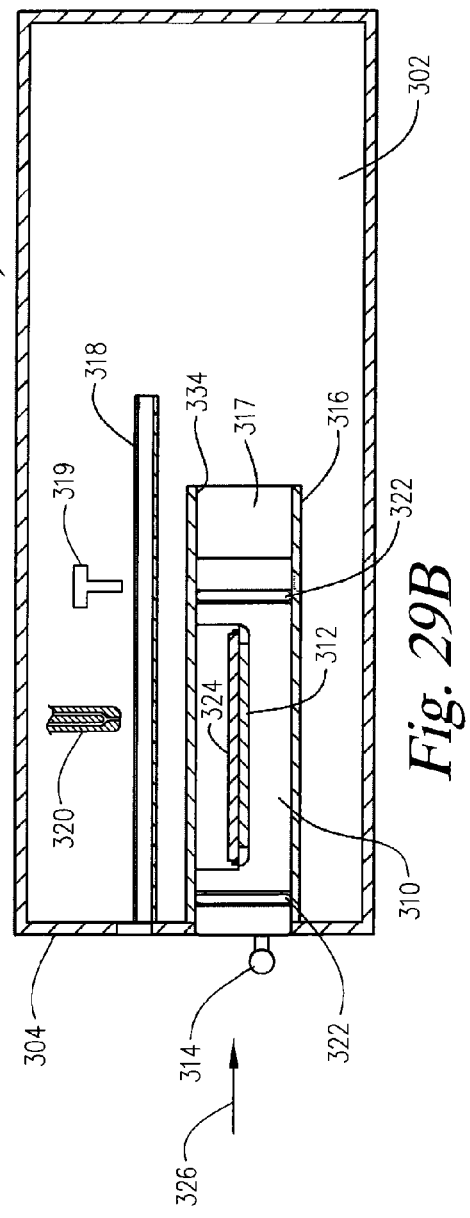
Fig. 29A
Fig. 29B

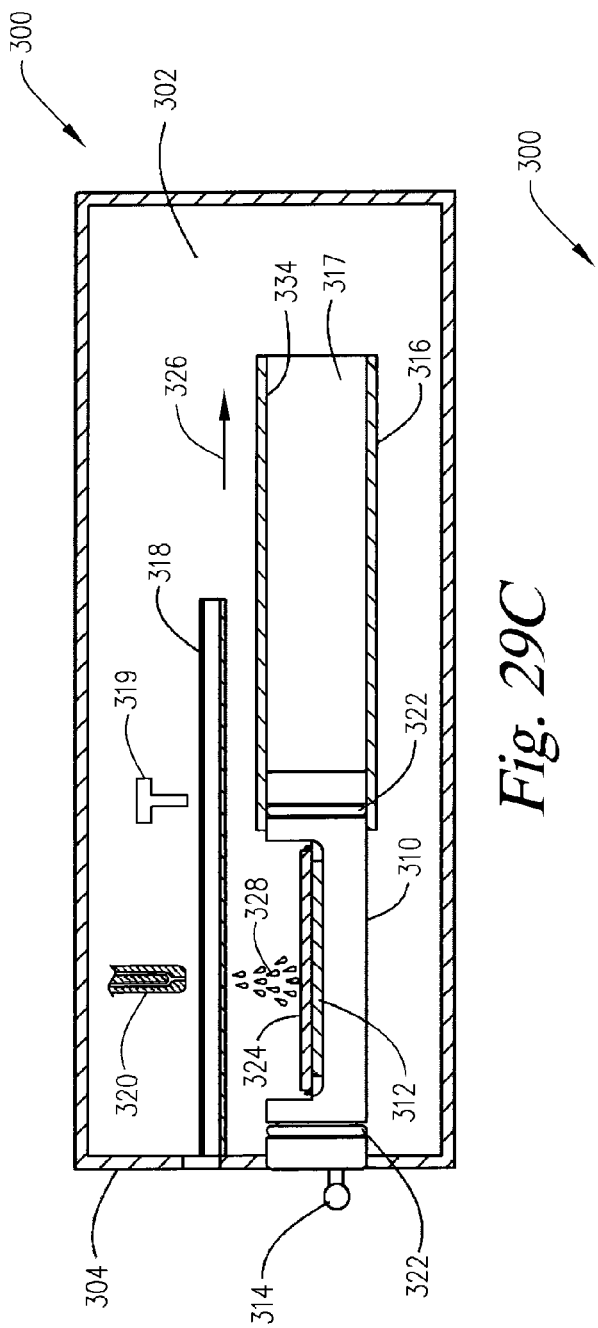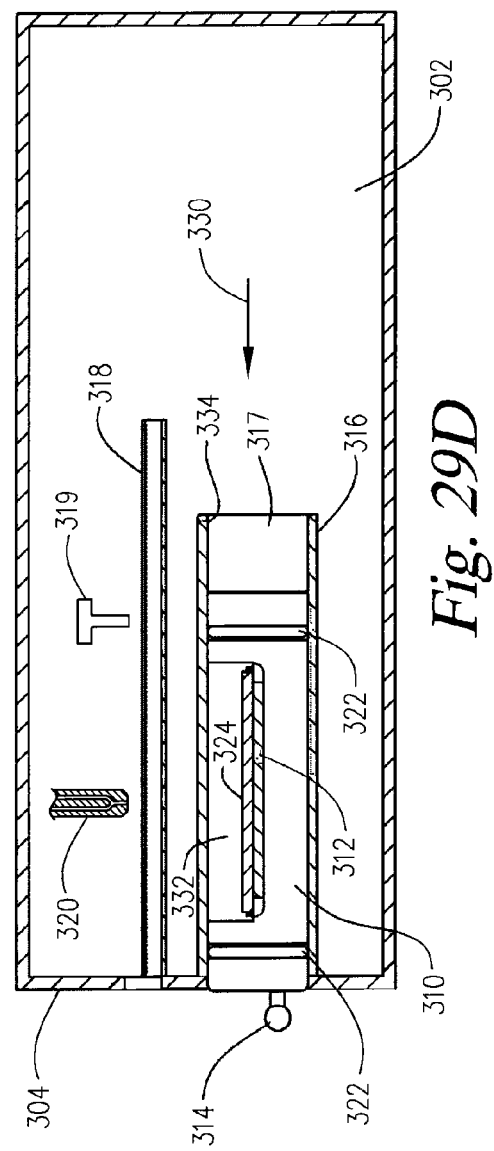

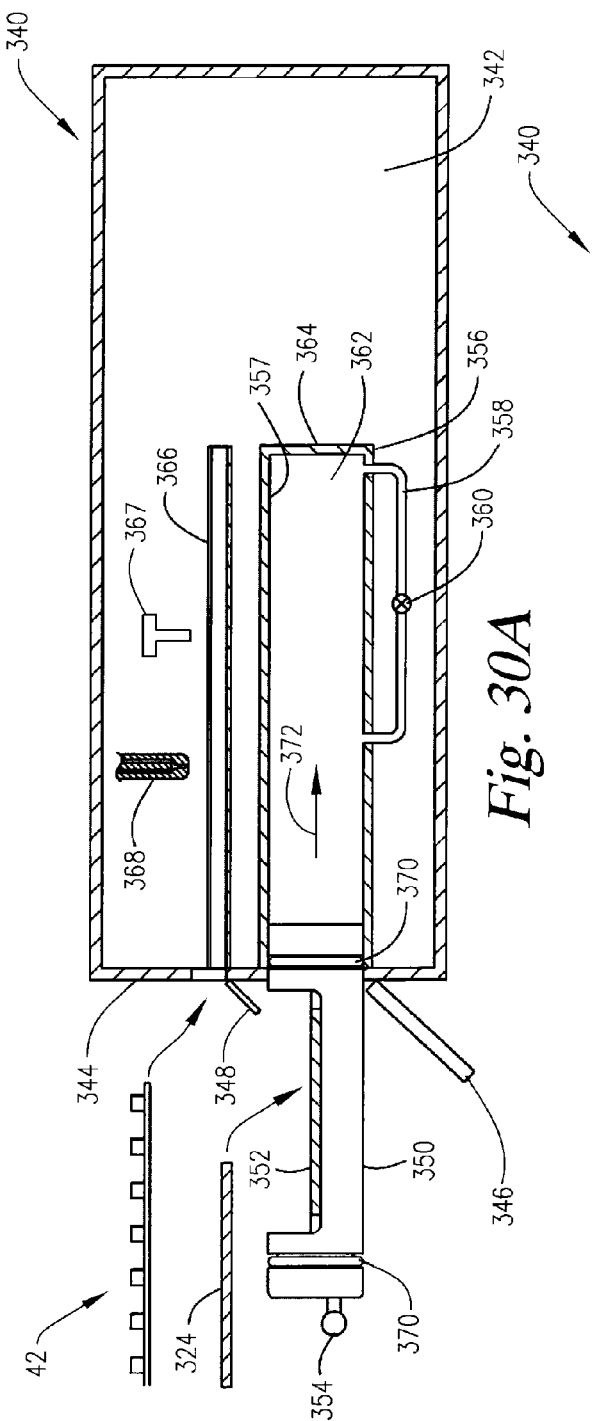
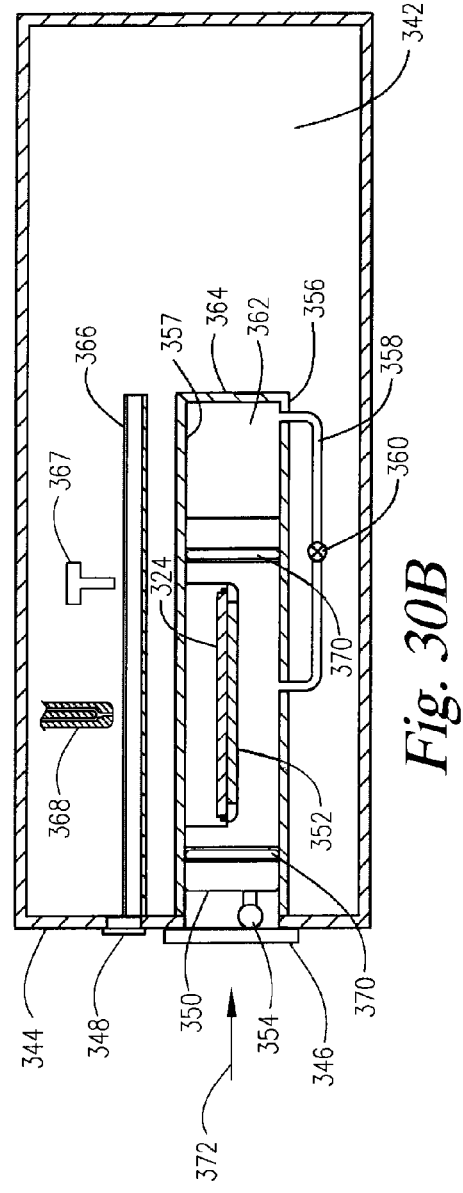
Fig. 30A
Fig. 30B

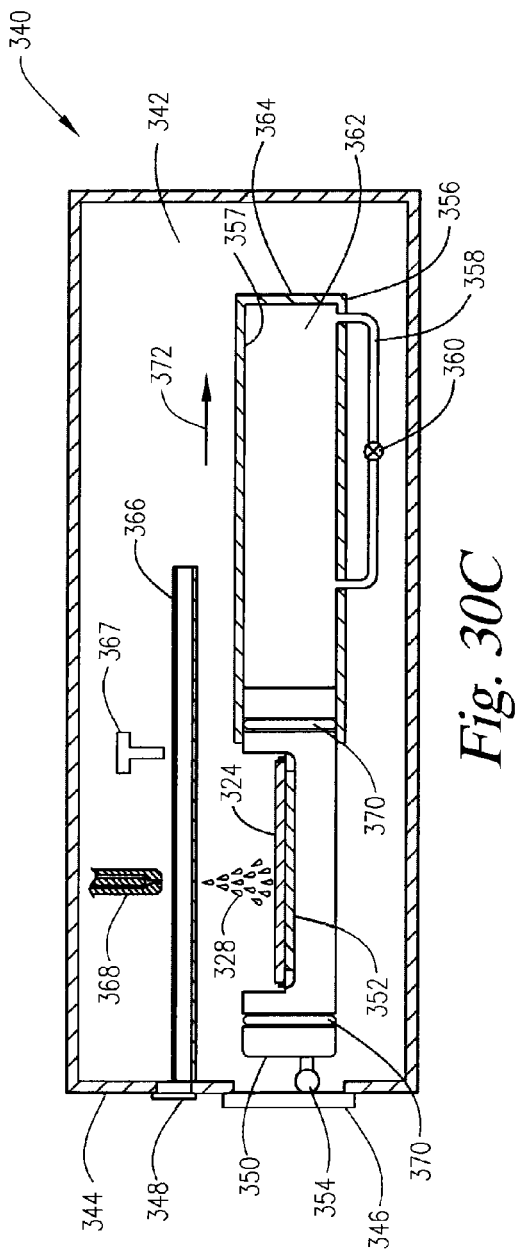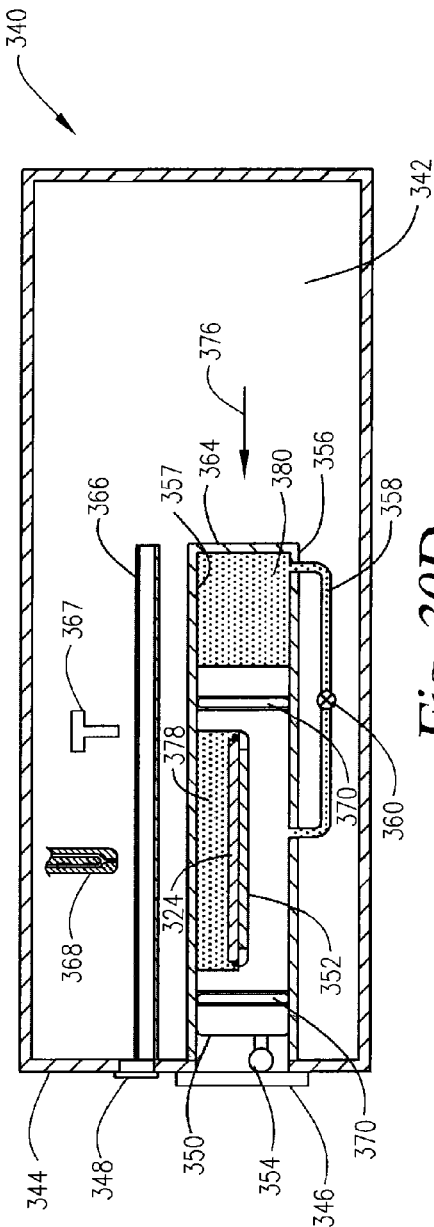
Fig. 30C
Fig. 30D

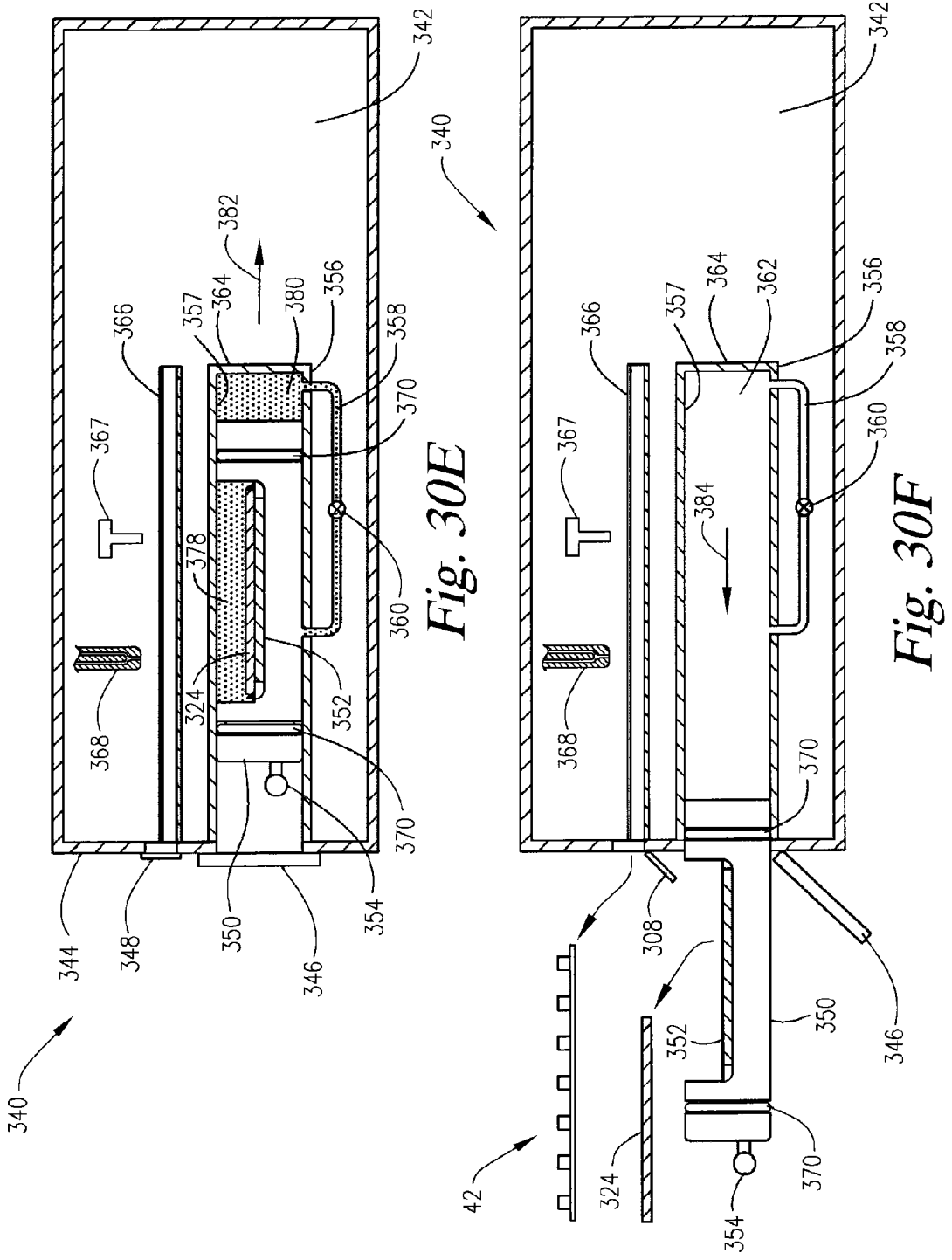

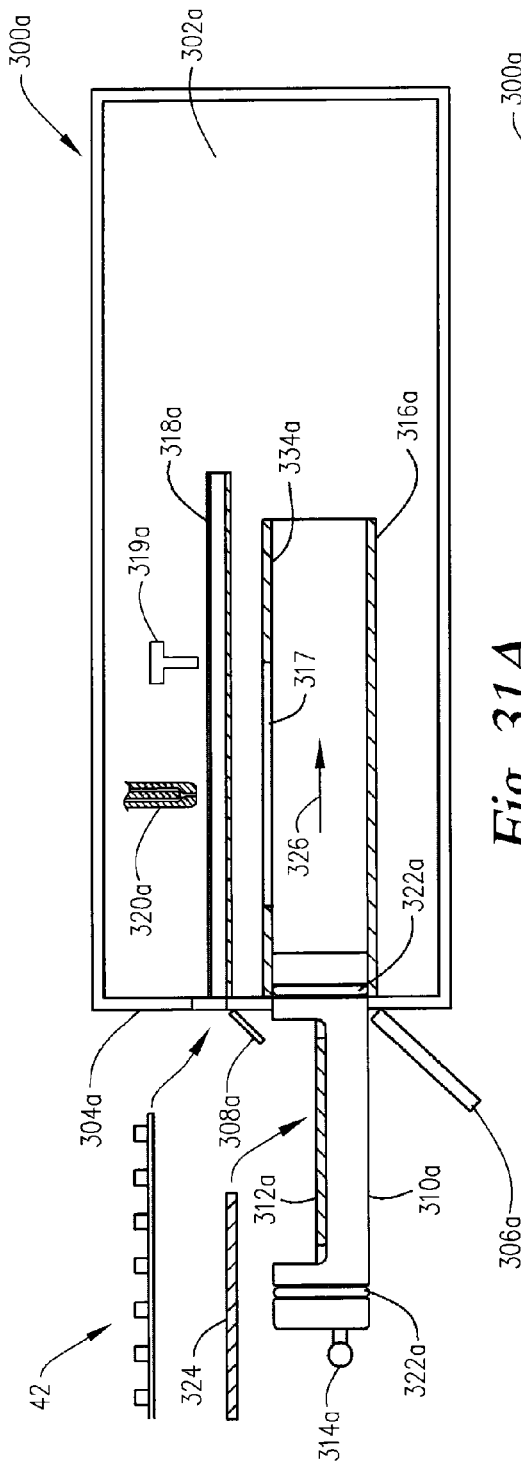
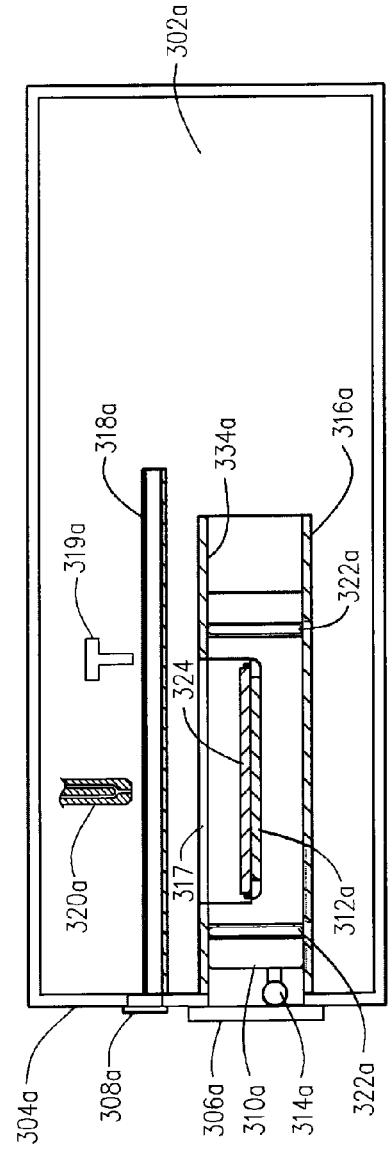
Fig. 31A
Fig. 31B

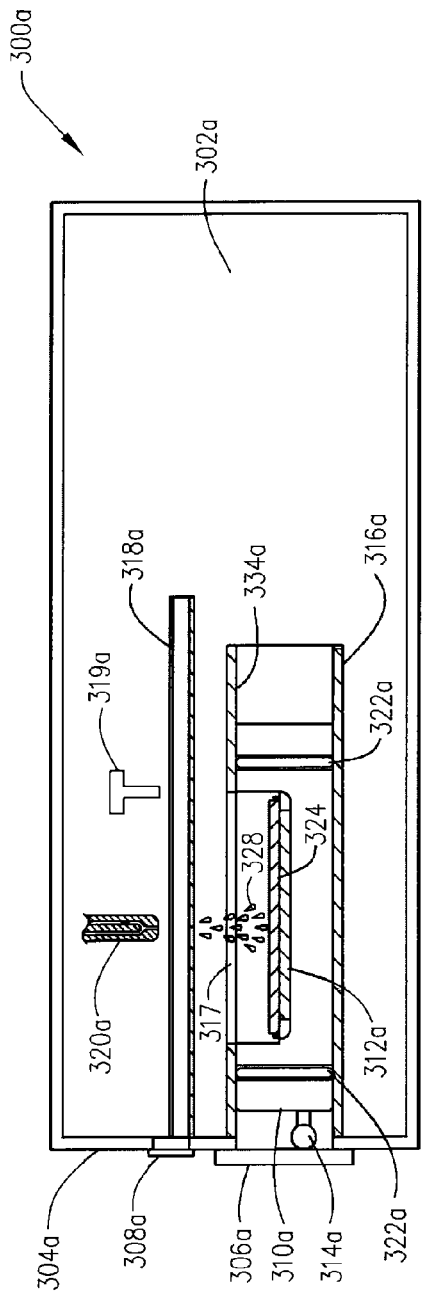
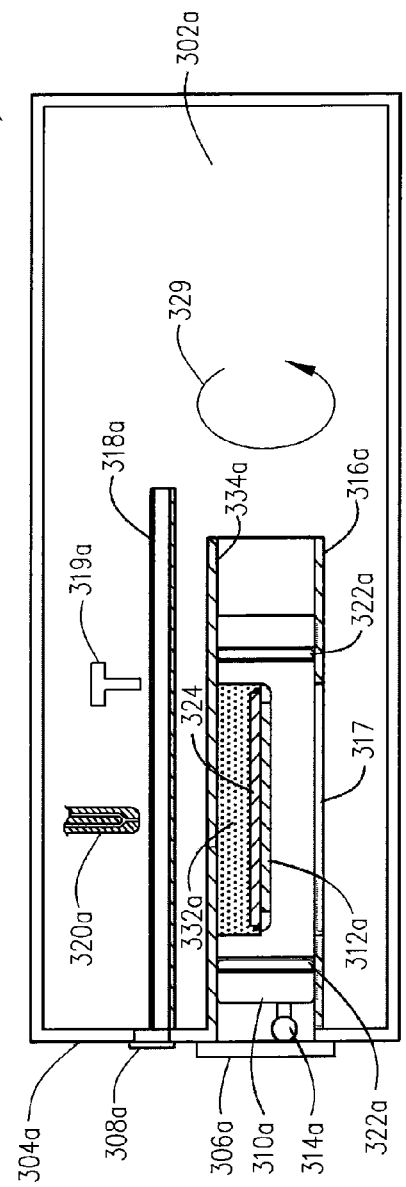
Fig. 31C
Fig. 31D

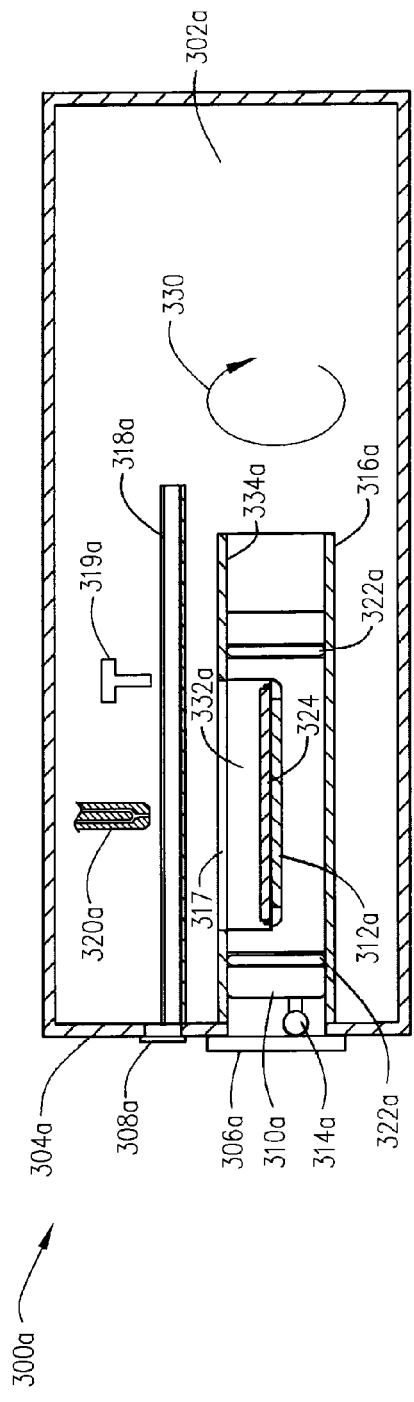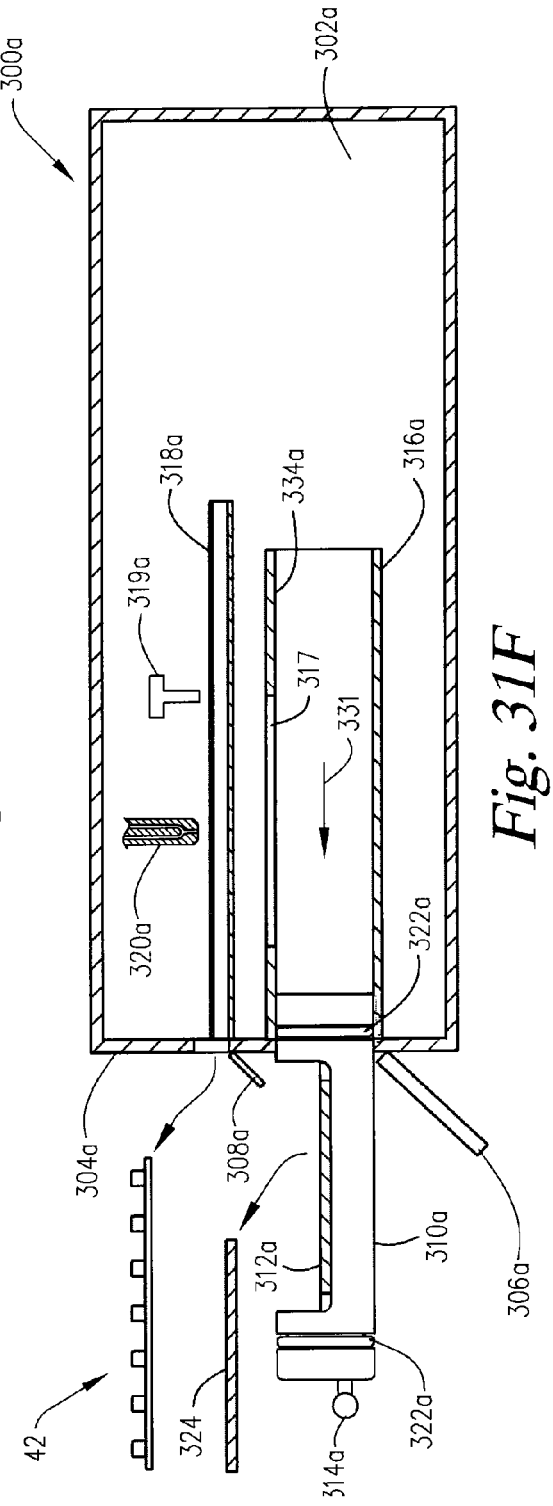

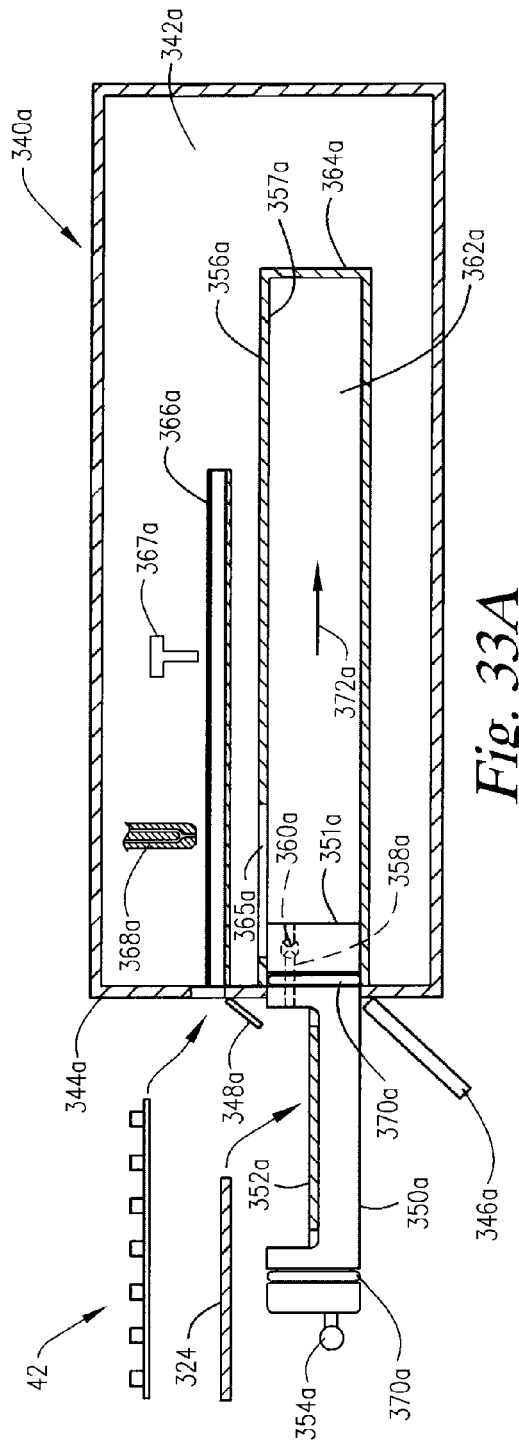
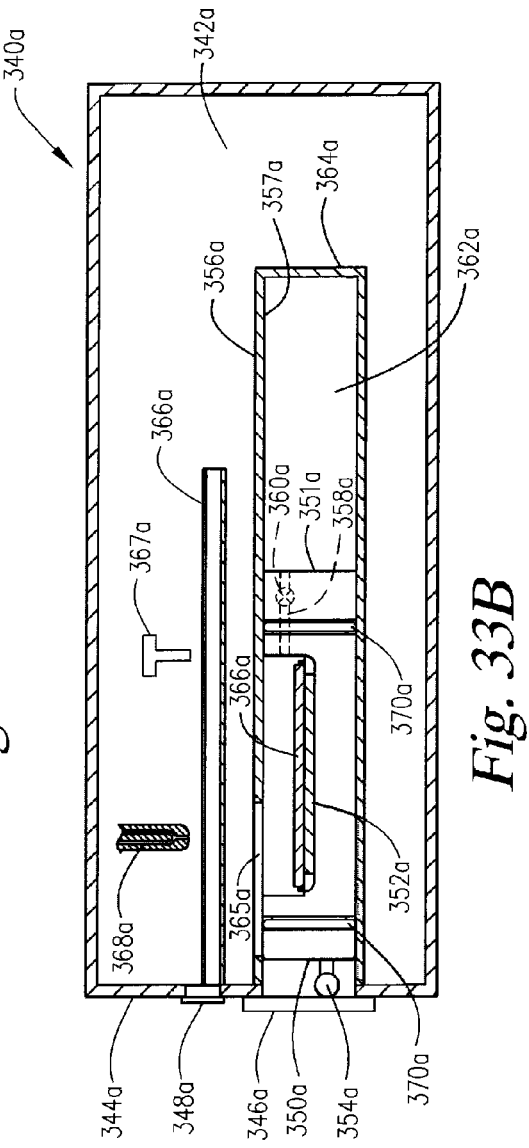

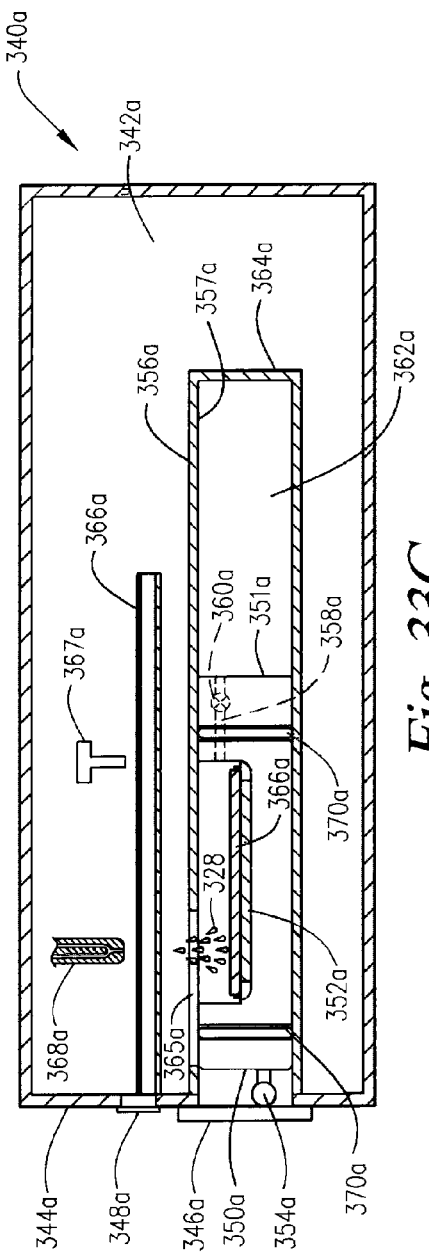
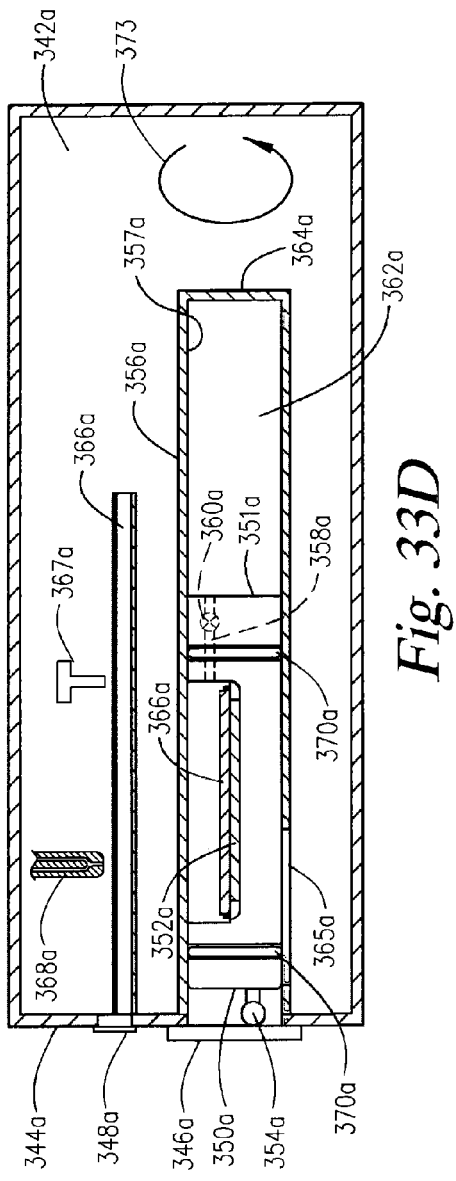
Fig. 33C
Fig. 33D

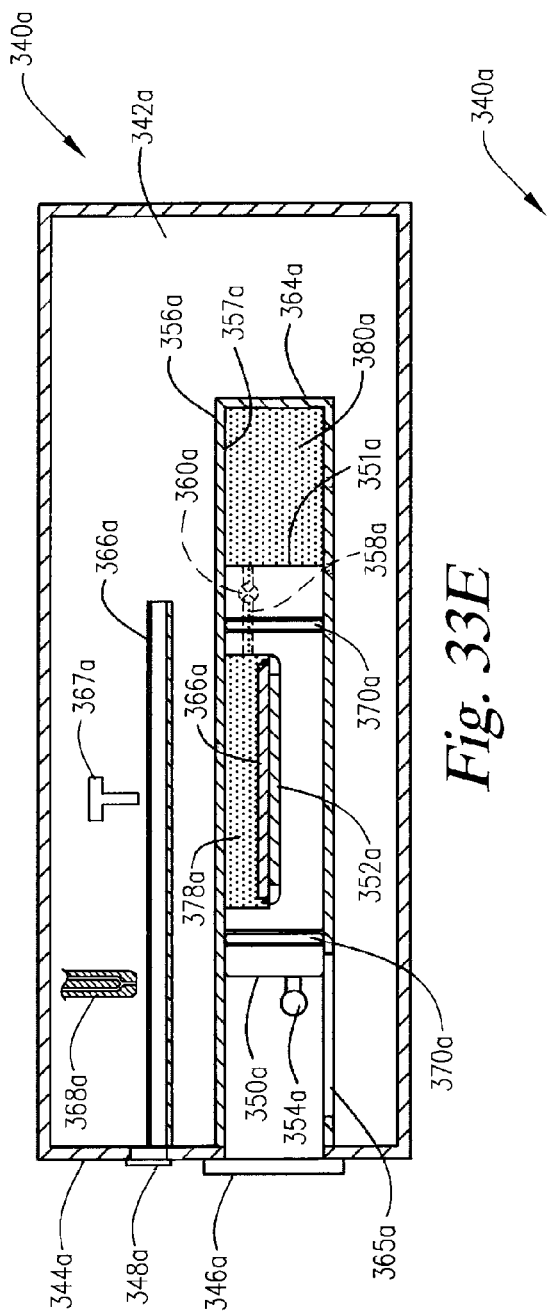
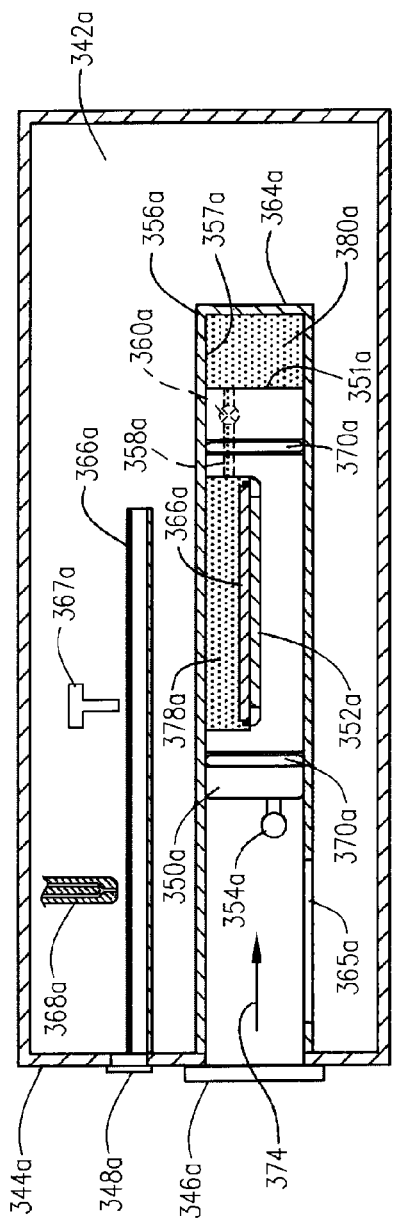
Fig. 33E
Fig. 33F

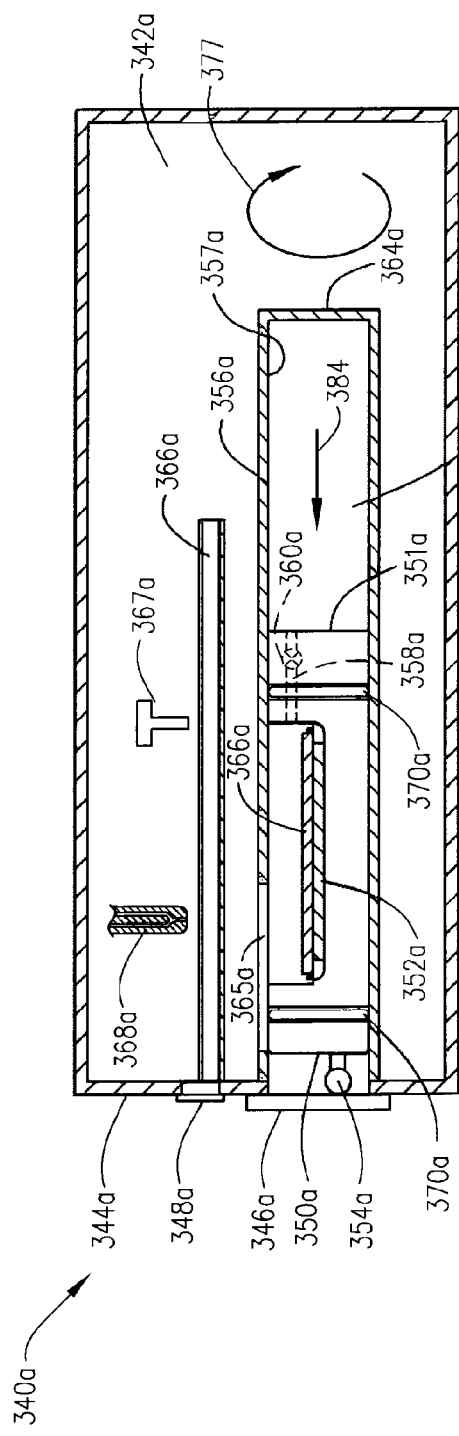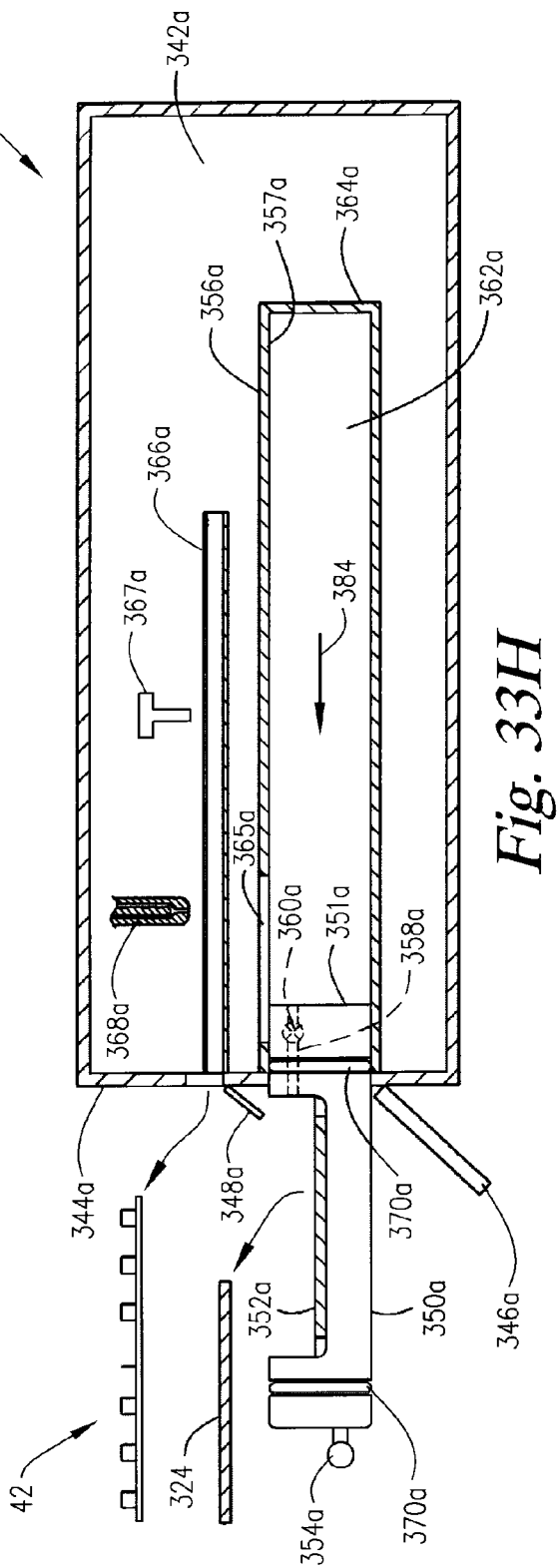

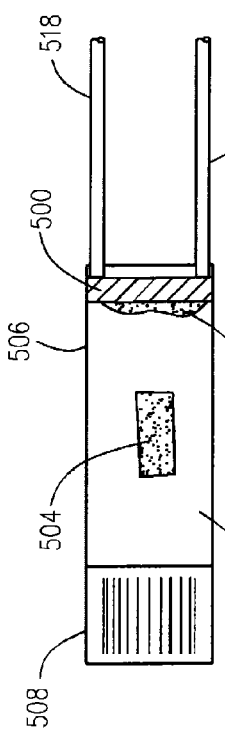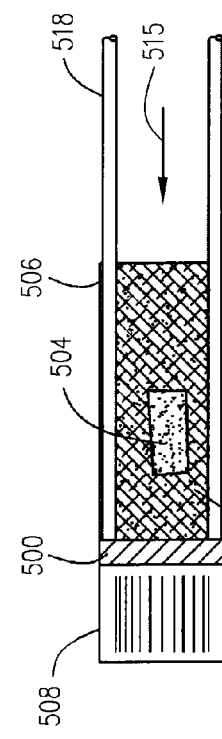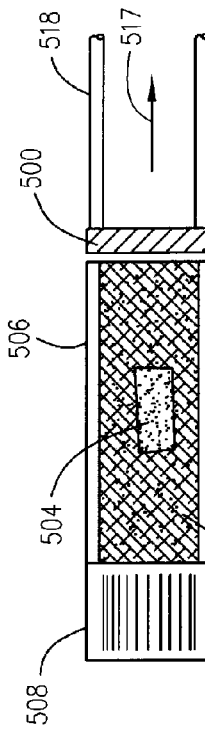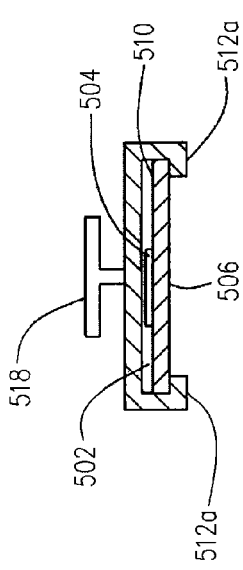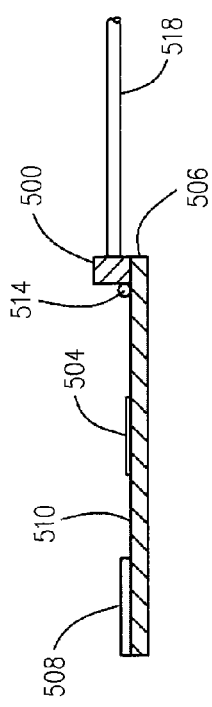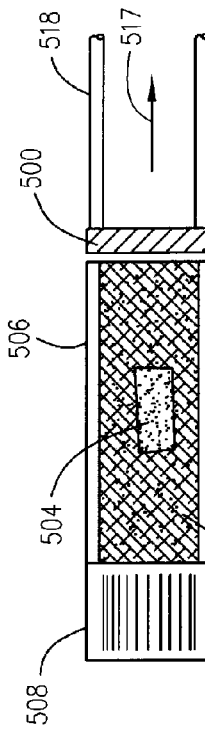

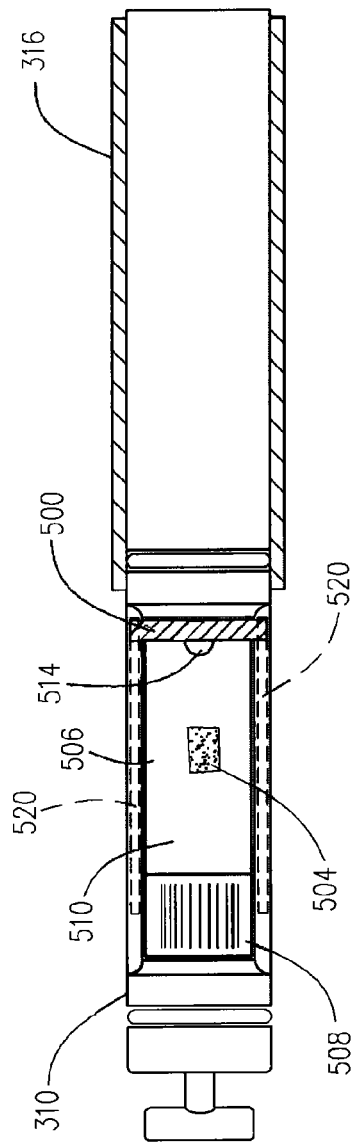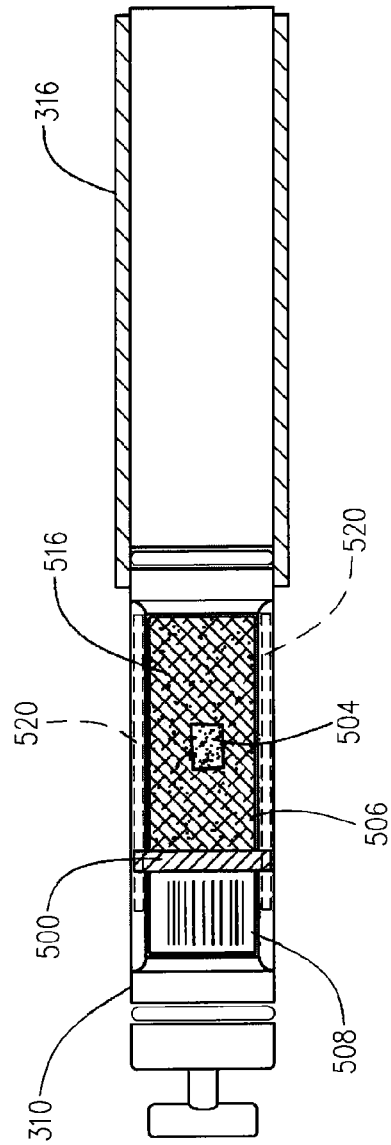

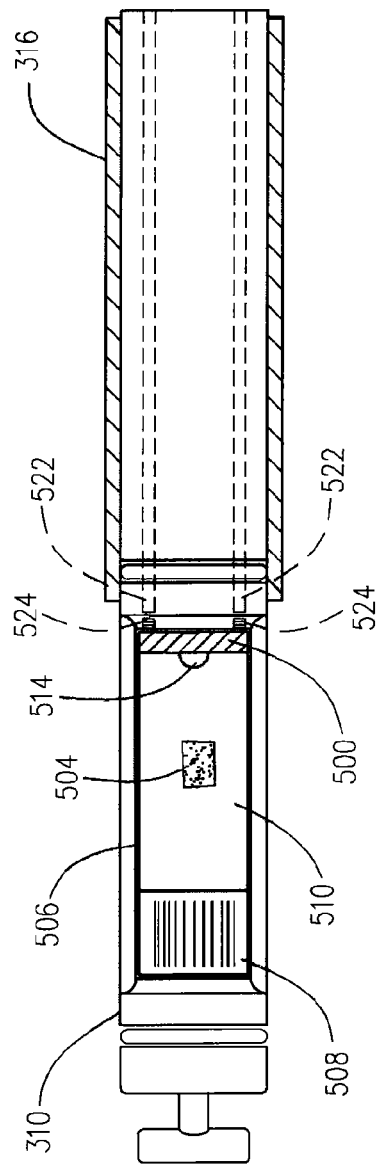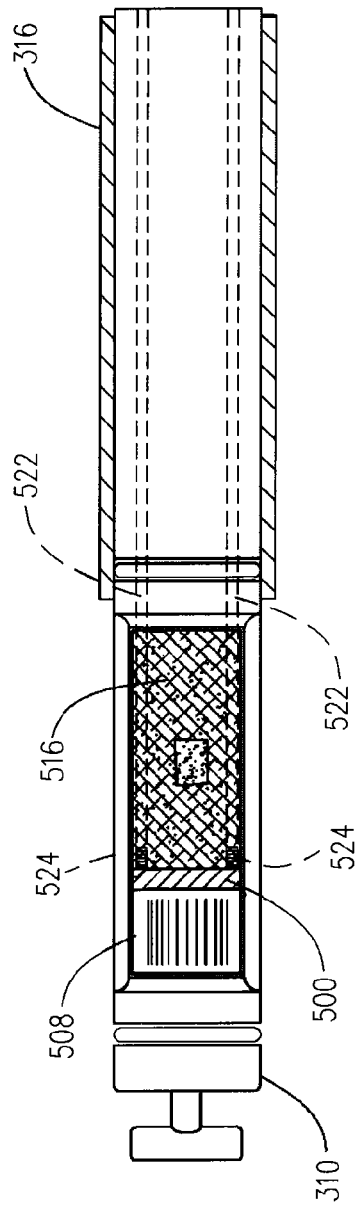

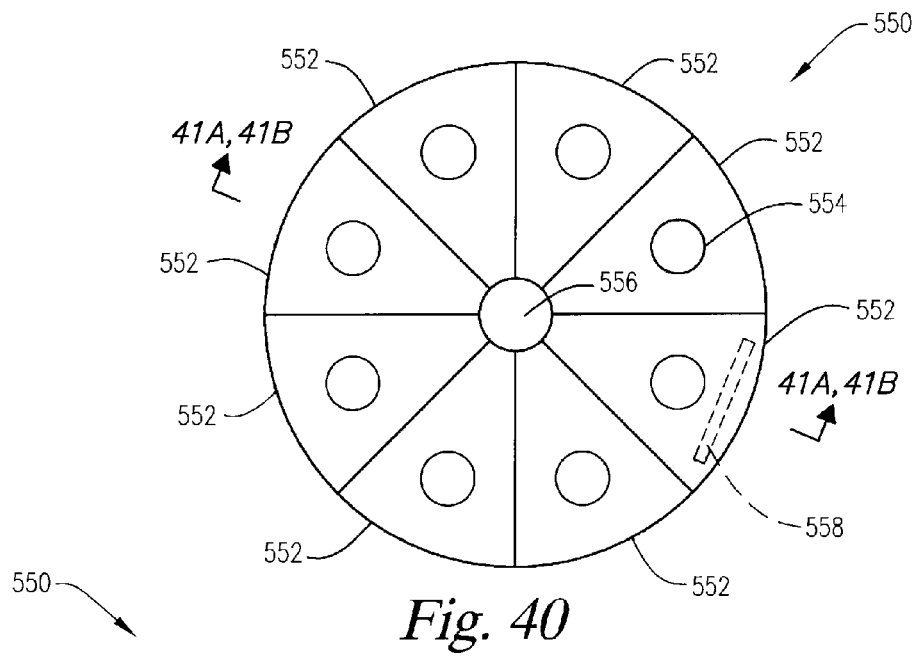
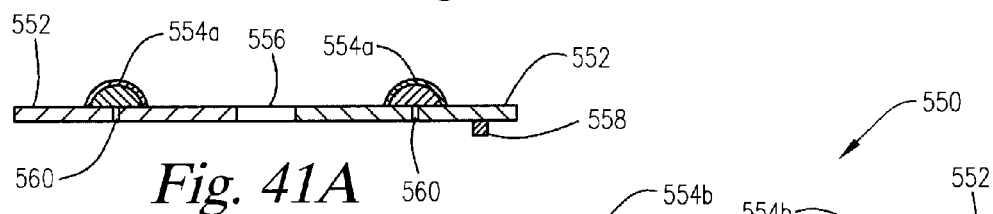
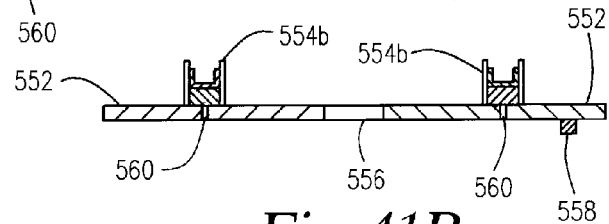
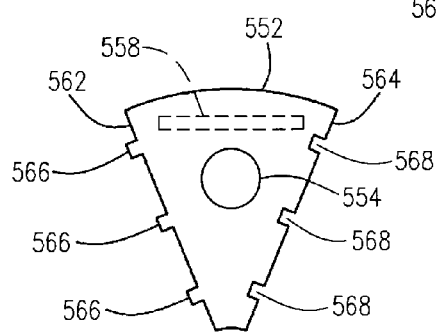
Fig. 40
Fig. 41A
Fig. 41B
Fig. 42

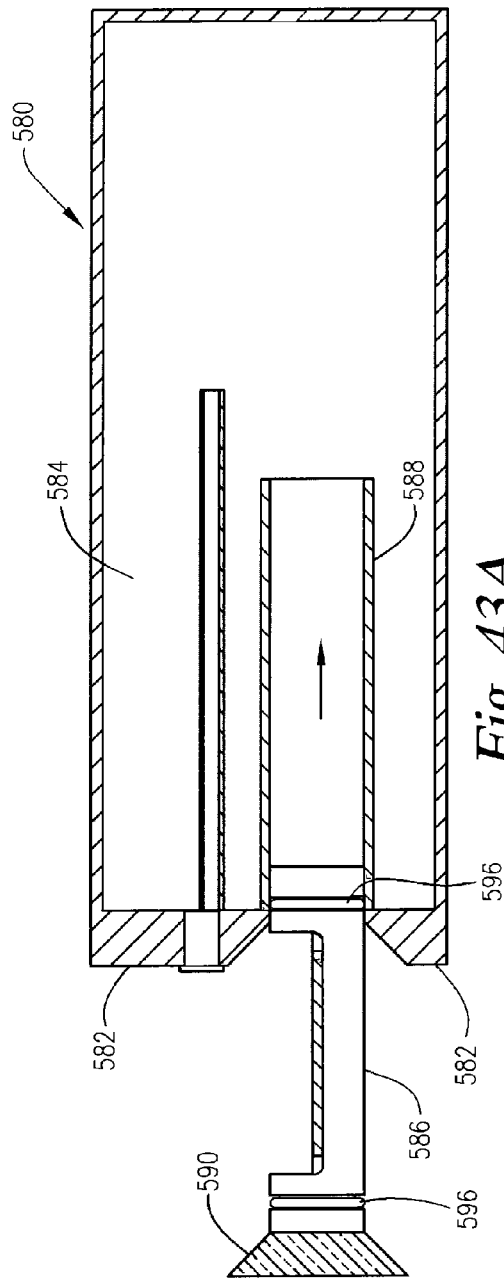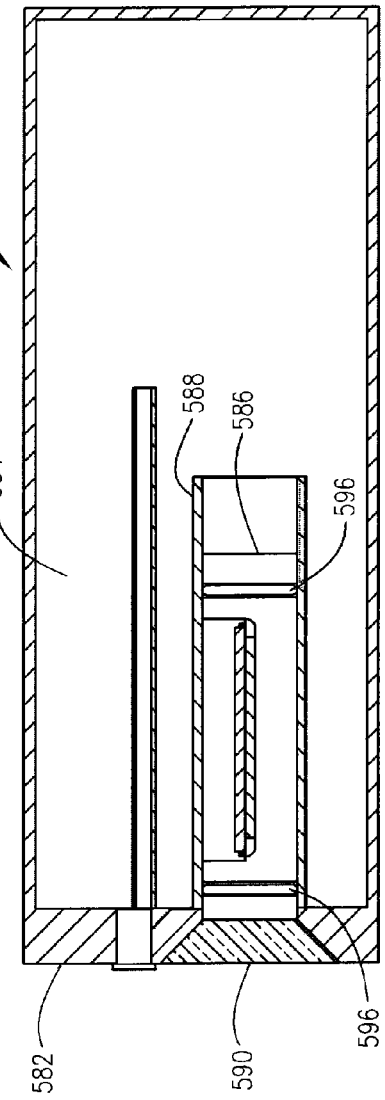

IN SITU HEAT INDUCED ANTIGEN RECOVERY AND STAINING APPARATUS AND METHOD

CROSS-REFERENCE TO RELATED APPLICATIONS

The present application is a continuation of U.S. Ser. No. 13/943,510, filed Jul. 16, 2013, which is a continuation of U.S. Ser. No. 12/550,296, filed Aug. 28, 2009, now U.S. Pat. No. 8,486,335, which claims the benefit of U.S. Provisional Application Ser. No. 61/190,503, filed Aug. 29, 2008; each of which is hereby expressly incorporated by reference herein in its entirety.

STATEMENT REGARDING FEDERALLY SPONSORED RESEARCH OR DEVELOPMENT

Not Applicable.

BACKGROUND

The present invention is related to the field of treating samples on microscope slides or other analytical substrates, and more specifically to the field of heat induced antigen recovery and staining of such samples.

In anatomical pathology labs (e.g., histology, cytology) it is known that certain immunohistochemical procedures, herein known as IHC assays, are performed on biological specimens including, for example, formalin-fixed paraffin-embedded tissues and cell preps. Also used in the art are several IHC antibodies (abs) like Estrogen receptor abs, Progesterone receptor abs, Proliferation abs like Ki-67, which require the use of high temperature unmasking techniques, (i.e., antigen retrieval, high temperature epitope recovery, and antigen unmasking), prior to application of the antibody for labeling cell structures (antigens).

There are several procedures known in the art for the "unmasking" of antigens that have been rendered "hidden" by formalin fixation. Procedures known in the art include treating the biological specimen in aqueous solutions (e.g., water) that may include buffers (e.g., citrate, EDTA, urea, etc.), along with detergents or surfactants (e.g., Brij 35, Tween, SDS, NP-40 and Igepal). These known formulations are heated to temperatures from around 60° C. to about 120° C. These heated formulations are in contact with the biological specimen for various amounts of time (e.g., about 10 minutes to about 90 minutes) thereby causing the "masked" antigen to become "unmasked" so the antibodies used in the IHC assays can attach to their corresponding antigens which are associated with the biological specimen.

Types of apparatuses that are known and used to perform the heating of the antigen retrieval solutions and the biological specimen include waterbaths, steamers, pressure cookers, autoclaves, microwave ovens and convection ovens. Since water boils at 100° C. at normal atmospheric pressure, antigen retrieval solutions even with other chemicals present have only been able to reach temperature from about 98° C. to 100° C. before evaporative heat loss inhibits the solution from reaching higher temperatures. Pressure cookers and autoclaves overcome this by allowing for pressurization of the solutions so higher temperatures can be achieved without evaporation of the heated fluid. Since there are antibodies that require the antigen retrieval solution be at temperatures exceeding 100° C., many laboratories must use pressure cookers to heat the biological specimen with its antigen retrieval solution to attain temperatures up to 120° C., without which the antigen would not be "unmasked" preventing the antibody from binding to the antigen.

There remains a need for an apparatus able to produce high temperature and pressure conditions for single slides being subjected to individualized antigen retrieval conditions without relying on clumsy and unwieldy devices such as pressure cookers and autoclaves.

BRIEF DESCRIPTION OF THE DRAWINGS

FIG. 8A is a cross-sectional side view of the reaction components of FIG. 7 in operation in a reagent dispensing phase.

FIG. 8B is a transverse cross-sectional view of the reaction components of FIG. 8A.

FIG. 9A is a cross-sectional side view of the reaction components of FIG. 7 and FIG. 8A in a reagent drainage phase.

FIG. 9B is a transverse cross-sectional view of the reaction components of FIG. 9A.

FIG. 10A is a cross-sectional side view of the reaction components of FIG. 9A in a rinse buffer dispensing phase.

FIG. 10B is a transverse cross-sectional view of the reaction components of FIG. 10A.

FIG. 11A is a cross-sectional side view of the reaction components of FIG. 10A in a rinse buffer drainage phase.

FIG. 11B is a transverse cross-sectional view of the reaction components of FIG. 11A.

FIG. 15A is a top plan view of the reaction compartment and slide support element of FIG. 13 which shows a clockwise air mixing step.

FIG. 15B is a transverse cross-sectional view of the air ports of the slide support element of FIG. 15A.

FIG. 16A is a top view of the reaction compartment and slide support element of FIG. 13 which shows a counter-clockwise air mixing step.

FIG. 16B is a transverse cross-sectional view of the air ports of the slide support element of FIG. 16A.

FIG. 17 is a view of the microscope slide and detached components of the heating element of the slide support element of FIG. 12.

FIG. 18A is a top plan view of a slide support element with the microscope slide and heating element detached to show air flow through the air cooling ducts which are used to enhance a rapid cooling of the heating element.

FIG. 18B is a transverse cross-sectional view through the air cooling ducts of the slide support element of FIG. 18A.

FIG. 19A is a cross-sectional side view of the reaction components of FIG. 18A.

FIG. 19B is a transverse cross-sectional view through the air cooling ducts of the slide support element of FIG. 19A.

FIG. 20 is a view of the microscope slide and detached components of the heating element of the slide support element of FIG. 12.

FIG. 21A is a top plan view of a slide support element with the microscope slide and heating element detached to show air flow through the air cooling ducts which are used to rapidly cool the heating element.

FIG. 21B is a transverse cross-sectional view through the air cooling ducts of the slide support element of 21A.

FIG. 22A is a cross-sectional side view of the reaction components of FIG. 18A.

FIG. 22B is a transverse cross-sectional view through the air cooling ducts of the slide support element of FIG. 22A.

FIGS. 29A-29F are cross-sectional side views of an embodiment of the invention wherein the slide support element is able to move into and out of the staining apparatus and reaction compartment, and the reaction compartment is able to move backwardly to enable application of the reagents directly onto the microscope slide on the slide support element.

FIGS. 30A-30F are cross-sectional side views of an embodiment of the invention wherein the slide support element is able to move to variable positions within the reaction compartment such that the pressurization within the reaction compartment is able to occur via compression of the head space ("in-situ" pressurization) of the reaction compartment by the slide support element.

FIGS. 31A-31F are cross-sectional side views of an embodiment of the invention which are similar to those of FIGS. 29A-29F, except the reaction compartment has an upper window through which reagents can be applied to the microscope slide without requiring movement of the reaction compartment backwardly. The reaction compartment can be rotated 180° (for example) to enclose the microscope slide within a pressurizable portion of the reaction compartment.

FIGS. 33A-33H are cross-sectional side views of an embodiment of the invention combining the "window" elements of FIGS. 30A-30F and the "in-situ" pressurization elements of FIGS. 31A-31F.

FIGS. 37A-37F shows a gap coating mechanism which causes a reagent to be spread over the biological specimen on the microscope during operation of the present invention. FIGS. 37A, 37B and 37C are cross-sectional views.

FIGS. 37D-37F are top views.

FIGS. 38A-38B shows top plan views of an alternate gap coater of the invention.

FIGS. 39A-39B are top plan views of alternate embodiments of the gap coater of the invention.

FIG. 40 is a top view of a reagent pack of the present invention.

FIG. 41A is a cross-sectional view taken through line 41A/41B of FIG. 40 which shows reagent containers as blisters or bubbles.

FIG. 41B is a cross-sectional view taken through line 41A/41B of FIG. 40 which shows the reagent containers as vials.

FIG. 42 is a top plan view of an attachable/detachable module of the reagent pack of FIG. 40 having a single reagent container thereon.

FIG. 43A-43B is a cross sectional side view of a slide support embodiment wherein the slide support element has a beveled seal for sealing with a front wall of the staining apparatus.

DETAILED DESCRIPTION OF THE INVENTION

Figure 1:
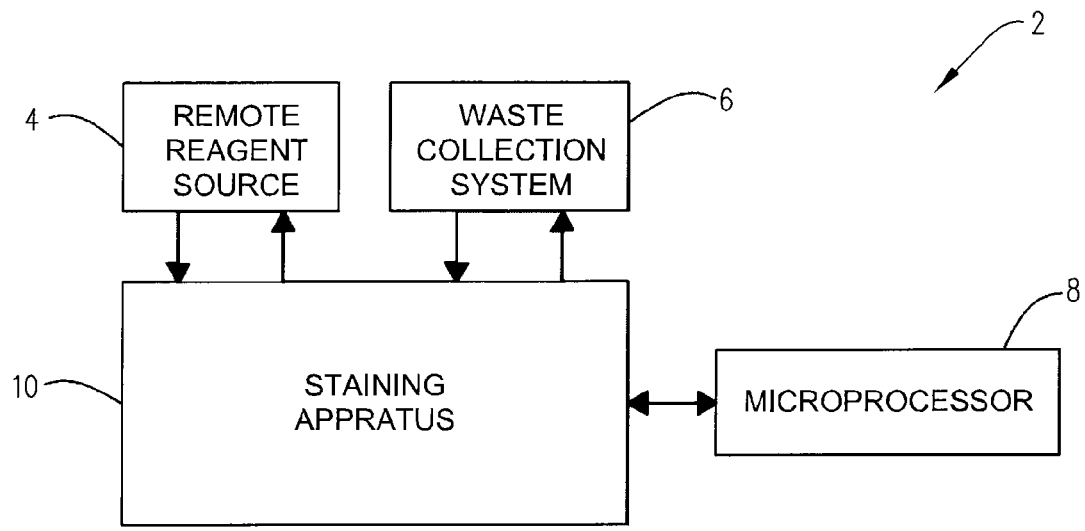
FIG. 1 is a schematic view of a microscope slide staining system of the invention.

Contemplated herein is an automated microscope slide staining system that features an apparatus comprising a plurality of independently movable and operable slide support elements for individually and independently processing and pressurizing a plurality of individual microscope slides. Where used herein the term "microscope slide" is intended to refer to conventional microscope slides as well as other microscopy analytical devices which are used as vessels, substrates, or support structures for supporting biological and biochemical specimens for testing, processing and/or analysis, and which are sized and shaped to fit on a support element as described and contemplated herein. Thus the term "microscope slide" includes, but is not limited to, devices such as biochips, vials, flasks, microtiter plates, test tubes, petri dishes, and microarray plates, as well as standard glass or plastic microscope slides. Preferably, the apparatus of the present invention is used as an automated in-situ antigen recovery and staining apparatus and preferably features independently movable slide support elements, each of which has an individually heatable heating plate or element associated therewith. Each slide support element preferably supports a single microscope slide. Each slide support element with the microscope slide thereon is, in a preferred embodiment, enclosable within its own individually and independently pressurizable reaction compartment and/or comprises a portion thereof. In one treatment step, for example, a solution such as an antigen retrieval solution is disposed on the microscope slide and the heating plate or element heats the slide and the antigen retrieval solution thereon to temperatures of, for example, 120° C. to 160° C. by regulating the pressure within the individual reaction compartment (or pressurizable common chamber of the staining apparatus as explained below) thereby increasing the temperature that the solution can attain. In one embodiment each reaction compartment has its own individual pressure regulator, device, or switch to regulate pressure within the reaction compartment but more preferably pressure is regulated by modulating heat and pressure within the reaction compartment. Pressures exceeding 1 atm (i.e., exceeding 14.7 psi, 0 psig or 101.325 kPa) or below 1 atm can be created and maintained in the reaction compartment and the biological specimen on the microscope slide is exposed to this pressure level. The reaction compartment can hold, for example, 0.1 ml to 100 ml of antigen retrieval solution.

Where used herein the term "biological specimen" includes, but is not limited to, unprocessed specimens, processed specimens, paraffin embedded tissue, whole mounts, frozen sections, cell preps, cell suspensions, touch preps, thin preps, cytospins, and other biological materials or molecules including blood, urine, cerebrospinal fluids, pleural fluids, ascites fluids, biopsy materials, fine needle aspirates, pap smears, swabbed cells or tissues, microbiological preps including bacteria, viruses, parasites, protozoans, biochemicals including, but not limited to, proteins, DNA, RNA, carbohydrates, lipids, ELISA reagents and analytes, synthetic macromolecules, phospholipids, support structures of biological molecules (e.g., metals, beads, plastics, polymers, glass), or any other materials attached to a biological testing substrate for processing, examination, or observation.

Each microscope slide at some point during treatment is treated with a liquid solution or reagent (generally referred to herein as "reagents" or "reagent elements" and including, but not limited to, antigen retrieval reagents, molecular RNA and DNA probes, citrate buffer, EDTA, TRIS, PBS, with or without surfactants or detergents like SDS, Tween, Brij, ionic and non ionic detergents, and silicone additives, rinse buffers, immunoreagents, immunohistochemical reagents, biological stains, histochemical reagents, counterstains, in-situ hybridization reagents, chromogens, PCR reagents, monoclonal antibodies, polyclonal antibodies, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives).

Because of the ability to pressurize and regulate pressure within the reaction compartment, and the ability to individually heat each slide, each slide can be heated to temperatures that could not be obtained without the elevated pressurized environment of the enclosed reaction compartment (or pressurizable common chamber). For example, since the vapor produced by the reagent is contained in the reaction compartment (or is released in a regulated manner), the pressure in the reaction compartment can be regulated to produce a reaction temperature required by the user. Pressures ("negative pressure", i.e., vacuums) below 1 atm (i.e., below 14.7 psi, 0 psig or 101.325 kPa) may also be created and maintained within the reaction compartment. For example, vacuum pressures of from 100 kPa to 10 kPa to 1 kPa to 100 Pa to 10 Pa to 1 Pa to 0.1 Pa may be formed and held in the reaction compartment.

In preferred embodiments, each reaction compartment and microscope slide can be heated separately and independently from the other reaction compartments and microscope slides by a conductive heating element (or heating plate) underneath or otherwise adjacent to the microscope slide (e.g., wherein the heating element is in a sidewall of the reaction compartment or in a cavity). In one embodiment in an enclosed reaction compartment, the microscope slide therein has an antigen retrieval solution deposited onto the microscope slide before or after being placed in the reaction compartment. The slide is then heated, in a preferred embodiment, to a temperature of about 100° C.-300° C. and under a pressure from 0.1 psig (102.015 kPa) to, for example, 350 psig (2515 kPa). In one embodiment the containment of the pressure is proportional to the temperature of the antigen retrieval solution, such that the regulation of both the temperature of the heating element of the reaction compartment and the regulation of the pressure generated by the solution on the slide can be adjusted during the automated staining procedure.

In one example, the heating element could heat the slide to 120° C. or greater and the pressure in the reaction compartment could be 16 psig (30.7 psi) wherein the solution on the microscope slide in contact with the biological specimen would be about 130° C., for example. It would be apparent to one of ordinary skill in the art of pressure regulated vessels that the temperature attained by the antigen retrieval solution would be dependant on the regulation and containment of either the pressure generated or the temperature of the heating element or both. If regulation of the temperature of the solution is to be at least partially determined by the pressure level in the reaction compartment, the heating plate can be set at 130° C. (for example) and the pressure relief valve could be set to a level to maintain a pressure of 19 psig (232.4 kPa) within the reaction compartment, for example. Thus, the temperature of the antigen retrieval solution would not substantially exceed 130° C. and would remain in the range of 120° C.-130° C.

If regulation of the temperature of the solution on the microscope slide is desired to be regulated by the temperature of the heating element, then the heating plate can be regulated to heat the slide to a desired temperature. Once the desired pressure within the reaction compartment has been reached, the temperature of the heating element is adjusted to keep the desired pressure within the desired limits. The reaction compartment under some conditions does not necessarily require a pressure regulator since the pressure in the reaction compartment may be determined solely by the temperature level of the heating element. In some embodiments it would be advantageous to have a regulator to relieve pressure if the pressure exceeds desired levels or to have a pressure regulator which would cause the heating element to be turned on and off depending on the desired pressure level.

Since "boiling" of the solution or reagent on the slide is suppressed by the containment of the pressure, the antigen recovery buffer or other reagent on the microscope slide may appear not to be boiling ("bubbling") even though it has actually reached a temperature at or above 100° C. Elimination or reduction of vapor loss due to boiling is advantageous because it removes the necessity of adding additional buffer during processing (such as is necessary when using certain other apparatuses known in the art, e.g., as shown in U.S. Pat. Nos. 5,654,200; 5,595,707; 6,296,809; 6,352,861; 6,582,962; 6,096,271; 6,180,061; 6,183,693; 6,541,261; or 6,783,733). This removal of the necessity to add reagent during treatment occurs even when only small amounts of buffers or reagents are initially used (e.g., 500 µl-4 ml) and treatment times may be extended up to 60 minutes at high temperatures (e.g., over 100° C., e.g., 120° C.-160° C.). Loss of reagent volume during heating in the present invention is thus minimal due to containment of vapors generated. Another important advantage to minimization of boiling at high temperatures is that the biological specimen on the slide is not subjected to extreme agitation from bubble formation which could cause the biological specimen to detach from the glass slide or be otherwise damaged. Moreover, the controlled pressurized micro-environment in the reaction compartment of the present invention is very efficient because the amount of buffer that is used is minimal and the amount of time needed to heat to high heat conditions (e.g., 120° C.-160° C.) is also minimal (e.g., 5 minutes).

Commercial pressure cookers which are currently available for use in antigen retrieval procedures are bulky and require a greater amount of buffer or reagent and time to complete the high temperature antigen retrieval process and furthermore must be used to treat many slides in the same container. The typical pressure cooker treatment cycle from start time to the last step (rinse) typically lasts 45-60 minutes. Only a few different buffers can be heated at the same time, (on the order of 5-6 separate slide treatment containers) within a pressure cooker's main reaction compartment. Moreover, each separate slide container in a conventional commercial pressure cooker requires significant volumes of antigen retrieval solution (e.g., 45-50 mls per container). As opposed to the pressure cookers which are used in the field of antigen retrieval, the apparatus and method of the present invention may use the vapor pressure generated by the reagent on the slide itself to produce an elevated pressure in the individual reaction compartment. Conventional pressure cookers, to the contrary, rely on a separate liquid present within the bottom of the vessel to produce the vapor necessary to cause increased pressure within the vessel for inducing antigen retrieval on the slides therein. This method requires the additional step of heating the separate liquid to an elevated temperature before the process of heating the slide and the reagent thereon can begin.

Each of the individual reaction compartments of the apparatus of the present invention, to the contrary, utilize relatively small quantities of antigen retrieval buffer (e.g., 0.5-5 ml per slide) and heat up quickly and cool quickly due to the small amounts of liquid and area to be heated and cooled. Even a volume of 0.1-1 ml per slide can be used with the present invention and the typical time from start to finish using the present invention may be just 20 minutes, for example.

In a preferred embodiment of the invention, to prevent small amounts of liquid reagents (e.g., including, but not limited to antigen retrieval reagents, RNA and DNA probes, citrate buffer, EDTA, TRIS, PBS, with or without surfactants or detergents like SDS, Tween, Brij, ionic and non ionic detergents, and silicone additives, rinse buffers, immunohistochemical reagents, histochemical reagents, in-situ hybridization reagents, PCR reagents, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives, or other reagent elements described herein) from being reduced in volume by the conversion from a liquid phase to a gaseous phase, and loss thereof, during heating (as occurs in other commercially available systems), the reaction compartment of the staining apparatus of the present invention, when closed, can be pre-pressurized, individually, prior to the heating of the slide and reagent. This pre-pressurization from a separate pressurization source, (i.e., rather than solely from the vapor pressure produced by the heated liquid in the reaction compartment), can significantly reduce the amount of loss of the gaseous phase (evaporation) of the small amounts of liquid reagents (e.g., 100 µl-5 ml) under high temperature conditions (e.g., 100° C.-160° C.) for extended heating times (e.g., 10-60 minutes) of the present invention, thereby eliminating the requirement of adding additional reagent after the treatment process has begun (i.e., after the reaction compartment or slide support element is isolated within the staining apparatus). For example, preferably, 0.1-4 milliliters of the reagent element (e.g., antigen retrieval reagent) is placed on the slide, the reaction compartment is then pre-pressurized and then the heating element begins to heat the reagent. The pre-pressurization of the reaction compartment, followed by heating of the reagent, produces an environment for the reagent to reach temperatures exceeding 100° C., for example up to 160° C., with minimal reagent loss due to gas phase formation (evaporation).

It is apparent that with the present invention particular temperatures and pressures can alternatively be established at any desired level for any treatment protocol known in the art of staining biological specimens. Super high temperature conditions can also be achieved using the present invention. These super high heating conditions can reach and exceed, for example, 350° C. and 300 psig (2170 kPa) due to pressurization, pre-pressurization, and the particular construction of the reaction compartment (described in further detail below). The individual pre-pressurizable reaction compartments of the present invention can be adapted to hold any type of vessel or substrate known in the art for containing a biological specimen for testing as described elsewhere herein.

In a preferred embodiment, the reaction compartment can be pre-pressurized and remain pressurized even under very high pressures of over 300 psig (2170 kPa) to produce very high temperatures exceeding 300° C. for use in special procedures that require such very high temperature conditions. In alternate embodiments, the reaction compartment can generate and sustain temperatures and pressures, for high heat conditions, in the range of 100° C. to 160° C. to 200° C. to 250° C. to 300° C., for example. Preferably, a pressure of at least 15 psig (204.8 kPa) is maintained within the reaction compartment during heating.

As described elsewhere herein, this heat can be generated by a conductive heating element positioned on or in the slide support element beneath the microscope slide, a conductive heating element in the reaction compartment wall, other types of heating devices in locations adjacent to the reagents being heated, microwaves passed into the reaction compartment to heat the regents, and/or magnetic induction for example. These types of heating devices can all be incorporated separately or together with the systems described herein for the regulation of pressure.

The regulation of pressure within the reaction compartment (or pressurizable common chamber), either by pre-pressurization from an extended source, or by pressure produced by evaporation of the heated reagent, or other means such as in situ pressurization described herein, is an important component of the invention.

A preferred embodiment the present invention eliminates the use of a single large container (e.g., a pressure cooker) to treat one or a plurality of slides under pressure. Each individually operable reaction compartment of a staining apparatus of the present apparatus can treat at least one individual microscope slide disposed therein with one or more individually applied reagents at an individualized temperature and pressure without relying on or affecting any of the other plurality of microscope slides in their respective reaction compartments in the same apparatus, i.e., each pressurizable reaction compartment can operate independently of each other pressurizable reaction compartment. An advantage of this embodiment of the invention is in its ability to treat every slide in the instrument separately and independently at an individualized temperature and pressure within a dedicated reaction compartment thereby increasing efficiency in the production and processing of specimens and providing a constant workflow advantage. Using this embodiment of the invention, a technician can separately begin a test of a slide utilizing any protocol at any temperature or pressure without affecting or stopping the other reaction compartments even when those other reaction compartments are already in use.

As described above, the temperature of the reagent on the microscope slide on the slide support element can be maintained by regulating the temperature of the heating element or by regulating the pressure to which the microscope slide is exposed or by both in combination. In one embodiment, for example, the heating element can be set to reach 125° C., the maintenance pressure can be set to 23 psig (259.9 kPa), and the reaction compartment can be pre-pressurized to 23 psig (259.9 kPa), and the slide can be heated such that the reagent on the microscope slide reaches a temperature of 125° C. for 10 minutes, and is then cooled for further processing. In a preferred embodiment, the pre-pressurized conditions may be attained before the microscope slide is heated so that, in this embodiment, the pressure in the reaction compartment is not produced by the vaporization of the liquid reagent contained in the reaction compartment, but rather by a separate pressurization method, system or device. The reaction compartment preferably holds a single microscope slide but can be adapted to hold two or more microscope slides. In the preferred embodiment, an individual reaction compartment is pre-pressurizable and is constructed to contain only a single microscope slide.

Without wishing to be held to theory, the pre-pressurization process, when using reagents (including any reagents described elsewhere herein) features conditions to minimize evaporative loss of reagents and or aqueous phase (water) or oil phase (oil) of reagents during heating and/or ambient temperature staining conditions. A further aspect of the embodiment featuring the independently pre-pressurized reaction compartments is that during the reaction process, pressure within the reaction compartment causes the reagents to come in close physical contact with the biological specimen by being "pressed" against the biological specimen wherein the physical contact between them is increased due to the pressure exerted on the reagent and thereby of the reagent upon the biological specimen.

This pressurized force of the reagent upon the biological specimen on the microscope slide helps to decrease the time of treatment by the reagents due to very efficient contact of the reagents with the biological specimen. Specimens may have their processing times significantly reduced due to superior staining caused by the reagents being physically "pressed" against the biological specimen, thus enhancing intimate contact with the biological specimen.

Polymerase Chain Reaction (PCR), including tissue PCR, is dependant on the retention of the water levels in the reagents during processing. Specific water concentrations, pH conditions, and temperatures must be strictly met in order for the PCR reaction to be successful. The pressurized conditions of the reaction compartment of the present invention are ideal for these conditions (low evaporation) to be met during staining. This low evaporation, due to an individually pressurized micro-environment (the individual reaction compartment) is ideal for PCR reactions on glass microscope slides, plastic microscope slides, vessels, tubes, micro arrays, micro titer plates, plates, or any other vessel used for the containment of biological specimens. This pressurization can also be used at ambient temperature as well (e.g., 25° C.).

In one embodiment of the apparatus, the pre-pressurizable reaction compartments are sized to hold only one microscope slide, while in an alternate embodiment, the reaction compartment can hold several microscope slides e.g., two, three, four, or more and can be pre-pressurized to decrease processing time and reduce evaporation or reagent loss.

The heating of the reagent on the microscope slide can be done by pre-pressurizing the reaction compartment with heated (below 100° C.) or super heated (above 100° C.) air (or gas) that would maintain the required temperature for the treatment protocol or would at least pre-heat the reaction compartment prior to the heating element reaching heating temperature or being turned on to heat, and maintain the heating of the reagent on the microscope slide. As noted above, in a particularly preferred embodiment of the invention, one or more of the reaction compartments of the staining apparatus is pre-pressurized after the microscope slide or slides are enclosed therein. The pre-pressurization of the reaction compartment may occur before, during, or after the heating element is actuated to heat the microscope slide and reagent thereon.

In another embodiment of the invention in which the apparatus comprises a pressurizable common chamber for pressurization without separate pressurizable reaction compartments (e.g., see FIGS. 35-36 below), a plurality of microscope slides together in the pressurizable common chamber may be pre-pressurized and heated thereby eliminating the need to add additional reagent to each microscope slide during the antigen retrieval process. For example, the plurality of microscope slides in the apparatuses shown in U.S. Pat. Nos. 5,654,200; 5,595,707; 6,296,809; 6,352,861; 6,582,962; 6,096,271; 6,180,061; 6,183,693; 6,541,261; or 6,783,733 may be enclosed within a pressurizable common chamber and pre-pressurized before, during, or after the heating step begins. In this embodiment, a plurality of microscope slides on independently movable slide support elements are enclosed within a pressurizable common chamber, reagent is applied to the microscope slides (before or after enclosure within the pressurizable common chamber), the pressurizable common chamber is pressurized to a level above atmospheric pressure, and the microscope slides are heated so the temperature of the reagent on the microscope slide exceeds 85° C. and more preferably exceeds 100° C. Further, the reagent could be applied to the microscope slides after the pressurizable common chamber is pressurized.

The same steps as above could be followed in an alternate embodiment absent inclusion of a heating process. The result of the process without heating is reduced evaporation or vaporization of the reagent from the slide while reagent is reacting with the specimen or sample on the slide and an increase in the physical interaction thereof, due to increased pressure of the reagent with the specimen or sample on the slide.

In a preferred embodiment wherein the apparatus comprises separate pressurizable reaction compartments, each microscope slide on each separate slide support element is processed within its own individual reaction compartment that can be individually pressurized. Each reaction compartment is operable separately from each other reaction compartment. Together they comprise an automated slide staining apparatus able to process a plurality of microscope slides simultaneously, if desired, yet independently. Each reaction compartment (and slide support element) is functionally operably independent (i.e., non-interdependent) from each other reaction compartment. The independent operability of each reaction compartment (and slide support element) is due to each reaction compartment having separate operational mechanisms, including but not limited to, individually moving slide support elements, individually moving reagent dispensing packs and/or reagent dispensing devices, and individually movable or stationary ports and dispensers for rinses, pressure, vacuum and waste disposal. Preferably each single individual processing device corresponding and dedicated to any of the reaction compartments is independent at any time of the operation of the dedicated processing components of another reaction compartment whether it is in operation or not, including, preferably, microprocessing programs unique to each reaction compartment. All processing components (e.g., including, but not limited to, reagent dispensers, rinse ports, vacuum ports, pressure ports, waste ports, mixing ports, slide support elements, reaction compartments, air cooling ducts, and liquid cooling ducts) can be individually and independently moveable and/or usable. The exception to this, in an embodiment of the apparatus, is one or more "X-Y-Z" positioning devices discussed elsewhere herein (e.g., FIGS. 34 and 35).

The apparatus of the present invention preferably comprises a microprocessor which utilizes an operating system that can have multiple, individually, and/or simultaneously running processing programs, partially or completely specific to each individual reaction compartment and/or slide support element. This would enable a simple approach to programming by eliminating the need for the microprocessor to have one operating program to determine and evaluate the status of all processing steps as in current slide staining instruments (e.g., as shown in U.S. Pat. Nos. 5,439,649, 5,595,707, 5,758,033, 5,839,091, 6,296,809, 6,352,861 and 6,783,733). In such staining instruments known in the prior art, microprocessors have a processing program which is "aware" of all the steps for each microscope slide in the staining process and which determines the correct time to activate a common processing device for a particular slide's use (i.e.—reagent dispenser, rinses, air applications, etc.) This "thinking and reacting" approach to the microprocessor's involvement in processing a plurality of microscope slides is inefficient. A lagtime is produced when all the microscope slides are under the control of one program. This inefficient use of time causes increased time for processing just because of the requirement of the microprocessor to determine the next step for each microscope slide and determine any conflicts with two or more microscope slides needing to be processed by a common device at the same time. This type of microprocessing delays the completion of the processing of a microscope slide that would need a processing device at the same time as another microscope slide or multiple microscope slides.

Some staining instruments known in the art feature a "STAT RUN" option. With this type of processing, the user has already started a staining run and has decided that one or more additional microscope slides need to be placed on the instrument and processed because the processing of the "additional microscope slides" is more urgent. The user can put the "original" microscope slides on a lesser priority setting. The "new microscope slides" can then be placed on the instrument and would receive the priority use of the "new microscope slides" of all the processing devices (e.g., reagent dispensers). In between the priority staining protocol, the processing devices can then be used to treat the "original" or "non stat" microscope slides that were on the independently operable instrument initially. The requirement for this type of interrupted processing is eliminated due to the features of the present invention.

The advantages of the microprocessor of the present invention having a single or unique program for each reaction compartment (and/or slide support element and/or reagent dispenser) eliminates the need for a microprocessor which is able to plan the interdependent steps for a plurality of slides being processed, as required by prior art systems. A further advantage of having a separate microprocessing program unique to each reaction compartment (and/or slide support element, etc.), is that if the programs of one or several reaction compartments fail, there will be no effect on the operation of the other reaction compartments (or slide support elements). One advantage to the individualized microprocessing system contemplated above is that there is no appreciable downtime in the event of a failure in one or a few reaction compartments (or slide support elements). To the contrary, in the instruments of the prior art, if the microprocessor or operating system fails, then the instrument is completely inoperable and must be repaired.

In the present invention, in a preferred embodiment, there can be a common "master" operating system that could be in communication with each individually unique program so that the user can open a separate program specific to any or all of the reaction compartments (and/or slide support elements) at anytime. The separate individual program running a specific reaction compartment (and/or slide support elements) would have all the protocols loaded therein for completely processing a microscope slide. The separate program could be updated and edited by the user and with the help of the master program could update all the other separate programs so that each reaction compartment (and/or slide support elements) could have the same protocols updates or edits. In the event of a master program failure, the separate unique programs to each reaction compartment (and/or slide support elements) would still be operational to process microscope slides; it just would lose the ability of communicate with the separate programs of the other reaction compartments (and/or slide support elements) for updating, downloading, or uploading information. In a variation of this, each reaction compartment (and/or slide support elements) may be individually separated and unique to itself with regard to its operating program with no link to the other reaction compartments (and/or slide support elements). A further advantage to having a master operating system is the ability to communicate with the other separate reaction compartment (and/or slide support elements) programs for diagnostic purposes, uploading, downloading, and general and specific communications between reaction compartments (and/or slide support elements).

In one embodiment of the present invention, all the motion control requirement necessary for operation of the system can be in the form of AC, DC, solar, and optionally other power sources like pneumatic and steam. The microprocessor can be run on AC, DC, and solar for example. The entire instrument is compact and can be configured with any amount or numbers of reaction compartments necessary. The instrument can be portable to be used in the field (research for example) or carried to an area of use. The number of reaction compartments (and/or slide support elements) typically would be 10-20 per chamber and are stackable or are joined linearly or are connected in any other manner which is appropriate (e.g., see FIG. 3B). A portable field unit could have as few as 1-5, or 5-10, reaction compartments (and/or slide support elements per chamber), for example, for less weight. Preferably the components are made from light weight, anti-corrosive materials. A further advantage of the present invention is that the instrument can be serviced in a modular approach. Each reaction compartment and/or slide support element and/or reagent pack support device in the module can be removed individually and serviced or discarded and replaced with an all new component. All the motion controls are preferably modular and either serviceable or completely replaceable. An advantage to this modular serviceability is that the other reaction compartments and/or slide support elements that are in use or could be used, are not affected during servicing of any device or part from a different reaction compartment and/or slide support element.

An advantage of the present invention, as explained previously, is that each microscope slide can be treated with a separate unique reagent, inferring that any microscope slide can have any reagent and be treated at pressures and for varying amounts of treatment times which are the same or different from any other microscope slide loaded into the apparatus. Examples of reagents which may be used in the present invention include, but are not limited to: antigen retrieval reagents, RNA and DNA probes, citrate buffer, EDTA, TRIS, PBS, with or without surfactants or detergents like SDS, Tween, Brij, ionic and non ionic detergents, and silicone additives, rinse buffers, immunohistochemical reagents, histochemical reagents, in-situ hybridization reagents, PCR reagents, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives. Another advantage with the present invention is that cross contamination from reagents or biological specimens on adjacent or nearby microscope slides is eliminated because each microscope slide is separated and treated with its own reagent in a separate reaction compartment or on a separate slide support element.

Another important advantage of present invention is that each individual reaction compartment and/or slide support element can be cleaned or repaired separately and automatically at the same time that other reaction compartments and/or slide support elements are being used to process microscope slides. Thus, there is no downtime or interruption for the other reaction compartments and/or slide support elements when a particular individual reaction compartment and/or slide support element is being cleaned or repaired. Each reaction compartment and/or slide support element can be separately cleaned and/or sterilized by steam, with or without a detergent or sterilizing reagent and dried with heated (below 100° C.) or super heated (above 100° C.) air. This type of sterilized cleaning could be used for example if a biological specimen that was being processed had infectious properties. Each reaction compartment essentially has the properties of an individual self-regulated and controlled miniature autoclave. Sterilization of each reaction compartment prior to use with the next biological specimen process can provide an inherent technical advantage due to the elimination of cross contamination and direct contact with infectious biological specimens. Sterilization can be performed using steam alone, or chemicals dispensed by a reagent pack or another dispensing element.

Pressure Cooker Method Vs. Present Method

The regulation of pressure in the reaction compartments or pressurizable common chambers of the staining apparatus of the present invention is different from that of a pressure cooker. A pressure cooker utilizes water at the bottom of the cooker to produce steam to heat the inside chamber and produce the pressure inside the chamber. A pressure cooker is constantly producing steam and therefore is pressurized from initial heating thru cooling. This pressure is constantly being released through a vapor pressure release device. The mode of release can be a "rocker valve" that is set for a certain psig release by the "rocker valve" having a specific weight. When the pressure cooker's closed chamber builds up pressure that exceeds the weight of the "rocker valve", the valve unseats or opens the closed chamber until the pressure decreases to a psig under the weight of the "rocker valve" This hissing that is normally heard around a pressurized pressure cooker is very apparent. The hissing is the unseating of the "rocker valve" to release pressure exceeding the "rocker valve" weight. This is the regulator system of a pressure cooker. Other models of commercial pressure cookers can also use a vapor pressure release device that are a pre-set one way valve that releases pressure in the pressure cooker's chamber when the pressure exceeds the pre-set valve psig. In all pressure cookers commercially known today there is always some way of releasing the pressure to maintain the pre-set limit of the pressure cooker. The pressure limits of commercial pressure cookers are not adjustable; in fact they are required to release the pressure in the chamber in a controlled manner to keep the pressure at a constant psig which is usually 24-26 psig.

The present invention uses a separate source of pressure to pressurize the individual reaction compartment or pressurizable common chamber before, during, or after the heating of the chamber or reagent. In the present invention, in this embodiment, maintaining pressure is in strict contrast to commercial pressure cooker's maintenance of pressure. The present invention doesn't release pressure to maintain a desired psig or temperature requirement. The present invention can pressurize in a range of 0.001 psig to 5000 psig. The present invention maintains the pressure at a desired psig by not releasing any of the pressure in the chamber. The pressure of the present invention is maintained by modulating (turning off and on) the heating plate temperature and the amount of pressure initially added to the individual reaction compartment or to the pressurizable common chamber, an example being the pressurizable chamber of the present invention, whether it's an individual reaction compartment holding a single microscope slide or biological specimen containing vessel, or a pressurizable common chamber holding a plurality of microscope slides or biological specimen containing vessels which is pressurized by a remote source of pressure initially and can be increased (if desired) by the minimal evaporation of the reagent associated with the biological specimen or microscope slide. The pressure of the present invention is maintained by containing, not releasing, the pressure generated during pressurization or heating. The pressure source can be from the head space, as describe elsewhere herein, or from a remote source. If the present invention utilized the method of a commercial pressure cooker to maintain and regulate pressure by producing pressure by evaporation and the subsequent release to maintain a desired psig, the reagent(s) present individual reaction compartments or pressurizable common chamber would go dry due to the complete evaporation of the reagent to produce the pressure that ultimately must be released to maintain the desired psig. The volume of the present invention typically utilizes very small amounts of reagents on the microscope slide to treat each slide (e.g., 0.1 microliters to 5000 microliters, preferably 1 microliter to 3000 microliters). If the pressure produced by the reagent(s) evaporating was allowed to be release from the present invention to maintain the desired psig, these very small amounts of reagent(s) present on the microscope slide would completely evaporate because the pressure they are producing is being released to maintain the desired psig by using the commercial pressure cooker's maintenance method.

In a preferred embodiment of the invention, particular reagents are supplied to the reaction compartment and/or slide on the slide support element from a reagent pack (also referred to herein as a reagent dispensing strip or pack) individualized for a single reaction compartment and/or slide on the slide support element as described in more detail in FIGS. 1-22 and 39-78 of Published PCT application WO 2006/127852 and elsewhere herein (e.g., FIG. 40-42). Due to the extensive discussion of such reagent packs described therein, it is not considered necessary to provide further explanation in the present disclosure except to the extent that further embodiments or details of operation are newly presented herein.

While the invention is now described herein in connection with certain embodiments and examples so that aspects thereof may be more fully understood and appreciated, it is not intended to limit the invention to these particular embodiments and examples. To the contrary, it is intended to cover all alternatives, modifications and equivalents as may be included within the scope of the invention as defined by the claims below. Thus, these examples and embodiments, which include preferred embodiments, will serve to illustrate the practice of this invention, it being understood that the particulars shown are by way of example and for purposes of illustrative discussion of various embodiments of the present invention for providing various principles and aspects of the present invention.

Moreover while various systems, devices, components, and apparatuses of the invention are described herein in particular embodiments and examples, it is intended that all such systems, devices, components and apparatuses be interchangeable in regard to the various combinations thereof which may be envisioned as embodiments of the invention described and claimed herein as long as such other embodiments which are not explicitly herein function in accordance with the present invention. For example, the various types of reaction compartments, slide support elements, heating elements, reagent pack support devices, dispensers, plungers, closure and sealing means, chambers, pressurization apparatuses, and spreading devices, to list but a few, can replace each other in various alternative embodiments of the invention.

Embodiments of FIGS. 1-6

Turning now to the figures, shown in FIG. 1 is a microscope slide staining system designated by the general reference numeral 2. The microscope slide staining system 2 in a preferred embodiment comprises a staining apparatus 10, a remote reagent source 4 operatively connected to the staining apparatus 10, a waste collection system 6 operatively connected to the staining apparatus 10, and a microprocessor operatively connected to the staining apparatus 10, and preferably to the remote reagent source 4 and waste collection system 6. The remote reagent source 4 of the microscope slide staining system 2 preferably has a self-contained D.I. water, buffer, and/or reagent liquid production and management module which is operatively attached to the staining apparatus 10. The remote reagent source 4 is also referred to elsewhere herein as a "reagent module" or as a "remote reagent source". This reagent module 4 can be plumbed to the staining apparatus 10 for "on-demand" efficient production of rinse buffers, antigen retrieval solution, or any type of liquid reagent used in treatment of microscope slides. The reagent module 4 can provide buffers or reagents like wash rinses, antigen retrieval solutions, fixation solutions hydration solutions, dehydration solutions, mineral oil solutions, surfactants solutions, ionic and or non-ionic additives solutions, buffer solutions, D.I. water rinses solutions, polyol additives solutions, alcohol solutions, xylene solutions, limonene solutions, Tween solutions, Brij solutions, and other reagents or solutions. The reagent module 4 can provide liquids for use in the staining apparatus 10 by filling a bulk bottle, bottles, or storage reservoir to be used by the staining apparatus 10. The bulk bottles would be operatively connected to each set of reaction components or to each reagent dispenser or to a dispenser of the X-Y-Z positioning device for use therein. The reagent module 4 can be connected to a known D.I. water source in the lab or can be plumbed to a tap water source to produce D.I. water in-situ. The regent module 4 may comprise reagent canisters (not shown) which are operatively connected in a series or parallel for different types of liquids to be dispensed in the staining apparatus 10. Different types of reagent canisters can be employed by the reagent module 4 to produce different types of liquids for the staining apparatus 10. Each reagent canister can produce its own "type" of "liquid" for use. The reagent module 4 preferably has a plumbed water supply, an electrical connection, and conduits or plumbing to the staining apparatus 10 for a closed system of operation. The reagent canisters may contain chemicals in a solid, liquid, gel, semi-solid, colloidal, or any known physical state for treating a water source to produce a "ready to use" or "on demand" production of reagents for the staining apparatus 10. The reagent canisters of the reagent module 4 can be plumbed in a series or parallel to facilitate removal and replacement of the reagent canisters when the staining apparatus 10 is in operation. There can be two or more of one specific "type" of reagent canister plumbed in a series or parallel on the reagent module to facilitate the removal of one empty canister, while the other or others are still in operation. Preferably, operation of the staining apparatus 10 does not have to be stopped to add or replace a reagent canister while the reagent module 4 is in use. The microprocessor 8 of the staining system 2 or a microprocessor in the reagent module can alert the technician to replace or remove a used or empty reagent canister.

In a preferred embodiment of the reagent module 4, the reagent module 4 is plumbed in line with a tap water source or DI water source to the staining apparatus 10. The staining apparatus 10 could use a salt-free rinse solution, for example, produced by the reagent module 4 comprising deionized water (DI water) with an ionic detergent, non-ionic detergent, cationic detergent or surfactant present. The tap water plumbed to the reagent module 4 can be deionized, distilled, purified, and or sterilized by the reagent module 4 by UV irradiation, and/or chemicals present in one of the canisters in the reagent module 4. If DI water is initially plumbed to the reagent module 4, the DI water can be treated similar to non-DI water or tap water to produce a very high quality sterile DI non-salt rinse with a surfactant present. The reagent module 4 may also be constructed to provide antigen retrieval solutions with different types of salts or surfactants known in the art of antigen retrieval solution or antigen unmasking solutions. These chemical or solutions are well known in the art. Antigen unmasking solutions can be, for example, citrate buffer, EDTA, antigen retrieval solutions having a pH in the range of 1-14, urea, with or without surfactants or detergents like Tween, Brij, IGEPAL, SDS, glycols, polyols, alcohols, and other ionic or non-ionic surfactants or detergents known in the art or others described elsewhere herein. This is a very convenient and economical way of providing these buffers or reagents "on demand" and delivering the buffers or reagents to the individual reaction components of the staining apparatus 10 without stopping or interrupting the slide being processed on the staining apparatus 10. The microprocessor 8 can alert the technician that one or more reagent canisters in the reagent module 4 are to be removed or replaced. The fittings on the reagent module 4 and reagent canister therein can be of any type of "quick connect" or "quick disconnect" component know in the art for liquid distribution connections. This concept of removing or replacing the reagent canisters "on the fly" without stopping the slide staining processes, complements the "independent access" of the staining apparatus 10 of the present invention. All prior art automated slide strainers have to, at some time, stop the slide staining process to either replenish, replace, or add reagents to their staining apparatus 10 during slide processing or before starting a new staining protocol. This embodiment of the present invention eliminates the need to stop the staining apparatus 10 merely to replace, change, or refill reagents required to stain a biological specimen on a microscope slide while the staining apparatus 10 is in operation processing at least one biological specimen on a microscope slide.

In a further embodiment of the present invention, as indicated in FIG. 1, the microscope slide staining system 2 comprises a self-contained waste collection system 6 also referred to herein as a "waste module 6" or "waste management module". This waste module 6 is operatively connected to the staining apparatus 10 for treatment of hazardous wastes or biological wastes or other wastes produced therein. The waste module 6 treats "on demand" both solid and liquid wastes. The waste module 6 preferably can separate liquid waste from solid wastes. The waste module 6 can treat the solid and liquid waste to produce non-hazardous waste that can be disposed by the laboratory disposal services. The waste module 6 preferably can separate hazardous waste from non-hazardous waste. If a hazardous waste can't be decontaminated by the waste module 6, the module will place the solid or liquid non-treatable waste into a sealed container (not shown) that can be disposed by lab personnel without the need to place the removable and disposable hazardous waste container in any other container for disposal. The waste container to be disposed will have fitted on its self a "break-away" fitting to seal the waste container from the lab's environment. The waste module 6 is preferably plumbed in a series or parallel to provide waste management while the staining apparatus 10 is in operation. The waste module 6 can decontaminate several hazardous wastes like, but not limited to DAB, Fast Red, Special Stains, Xylene, alcohol, chromogens, reagents, buffers, infectious and biological waste, etc. Each hazardous chemical, liquid, gas, or solid can be decontaminated by its own decontaminating canister or non-treatable waste can be separated into disposable waste canisters. Each decontamination canister can be separately removed or replaced on demand without stopping the staining apparatus 10 during operation.

The schematic in FIG. 1 is intended to representative of any microscope slide staining system contemplated herein and may comprise components of any of the invention embodiments described or contemplated herein in any combination which functions in accordance with the treatment, staining, and pressurization aspects of the present invention.

Figure 2:
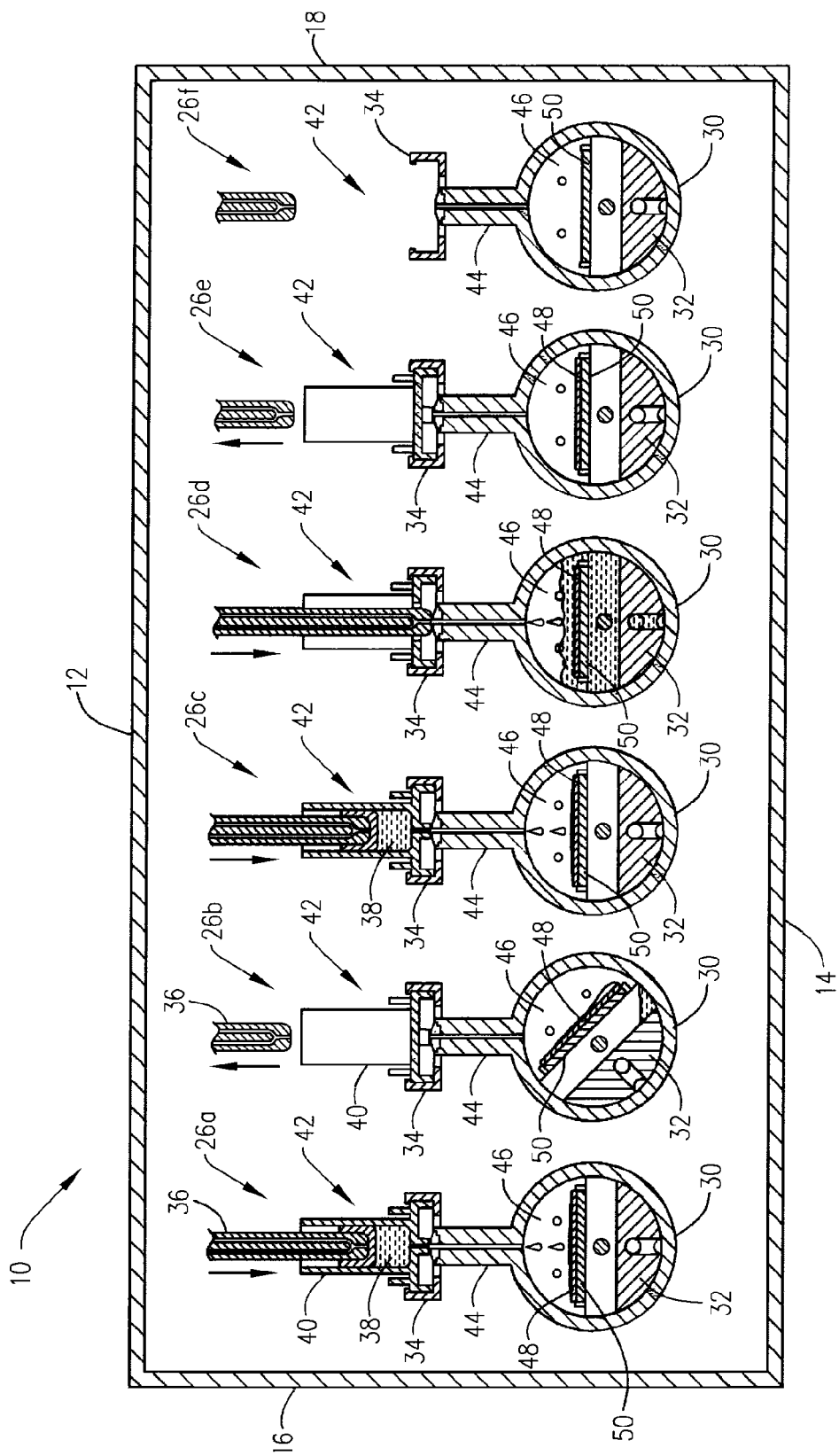
FIG. 2 is a front cross-sectional view of a staining apparatus of a microscope slide staining system of the present invention.

Shown in greater detail in FIG. 2 is the staining apparatus 10 of the microscope slide staining system 2 of the present invention. Staining apparatus 10, shown in FIG. 2, is substantially the same as the single chamber 282 shown in FIG. 85 of the parent application U.S. Ser. No. 11/439,722, comprises a top upper wall 12, a bottom wall 14, first side wall 16 and second side wall 18. The staining apparatus 10 further comprises a front wall 20 (FIG. 3A), a back wall 22 (FIG. 4), and an inner space 24. Contained within the inner space 24 are a plurality of sets of reaction components 26 (also referred to herein as reaction modules). FIGS. 2-6 and 34-36 show six sets of reaction components 26a-26f in the staining apparatus 10, but this is for illustration only. In other embodiments of the staining apparatus 10 any number of sets of reaction components 26 may be present, for example, less than or more than 6, such as 4 to 50 sets of reaction components 26.

Each set of reaction components 26a-26f comprises, in the embodiment of the invention of FIG. 2, a reaction compartment 30, a slide support element 32 for supporting a microscope slide 48, a reagent pack support device 34 for supporting a reagent pack 42, and a dispenser plunger 36 for causing expulsion of a reagent from a reagent container 40 of the reagent pack 42 onto the microscope slide 48. The dispenser plunger 36 (also referred to herein in some embodiments as a dispensing element) may move in an upward or downward direction for being positioned to dispense a reagent 38 onto the microscope slide 48. For example, in FIG. 2, reaction components 26a and 26c show the dispenser plunger 36 forcing the reagent 38 from the reagent container 40 of the reagent pack 42 which is positioned on a reagent pack support device 34. The reagent 38 is forced through a reagent conduit 44 of the reaction compartment 30 into an inner space 46 thereof onto a microscope slide 48 placed upon the slide support element 32. The dispenser plunger 36 is then withdrawn from the reagent container 40 (as shown for reagent components 26b and 26e). In some cases the dispenser plunger 36 is able to cause expulsion of a reagent 38 from the reagent pack 42, and is also able to separately dispense a reagent delivered from a remote reagent source 4. In other embodiments, these functions may be performed by separate devices such as the dispensers 319 and 320 described in further detail below in regard to FIG. 29A for example. The microscope slide 48 may be heated by a heating element 50 which is positioned on the slide support element 32 underneath the microscope slide 48. As is indicated in FIG. 2, each set of reaction components 26 can be in a different phase of operation independently of each other. For example, in FIG. 2, reagent 38 is being dispensed onto the microscope slide 48 in reaction components 26a and 26c. Reagent 38 is being removed from slide support element 32 by tilting thereof in reaction components 26b. In reaction components 26d, the inner space 46 of the reaction compartment 30 has been flooded with a reagent 38 for treating or rinsing the microscope slide 48. In reaction components 26e, the dispenser plunger 36 has been removed from the reagent pack 42, reagent 38 has been removed from the microscope slide 48 and the slide support element 32 is in an "upright" position for allowing further treatment or disposition of the microscope slide 48. In reaction components 26f, the reagent pack 42 has been removed from the reagent pack support device 34 and the slide support element 32 is without a microscope slide 48.

Figure 3B:
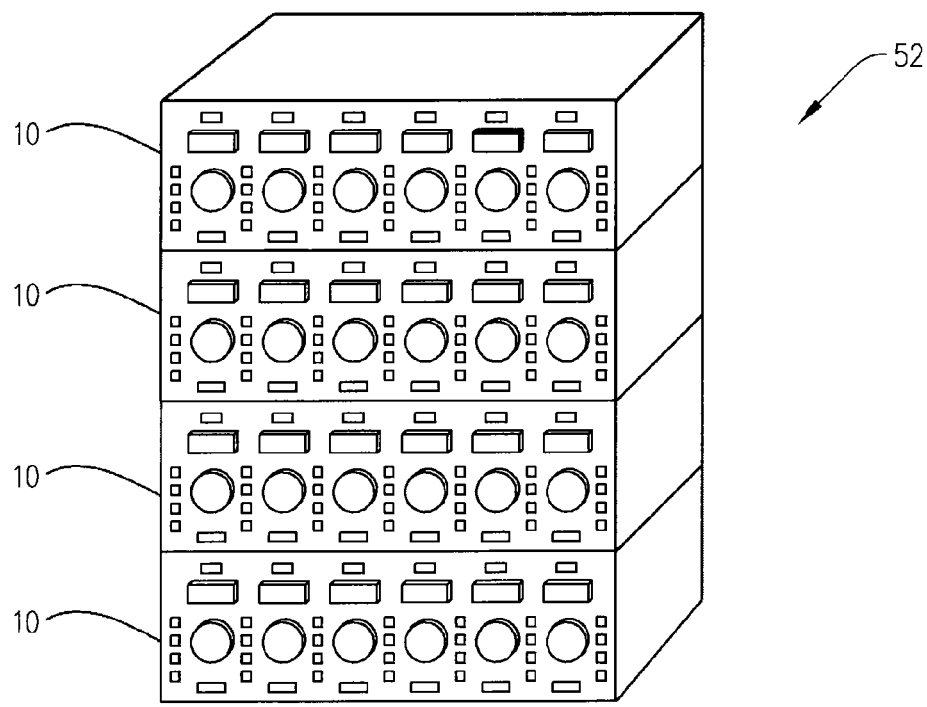
FIG. 3B is a perspective view of a microscope slide staining system of the present invention having four staining apparatuses such as the apparatus of FIG. 3A.
Figure 3A:
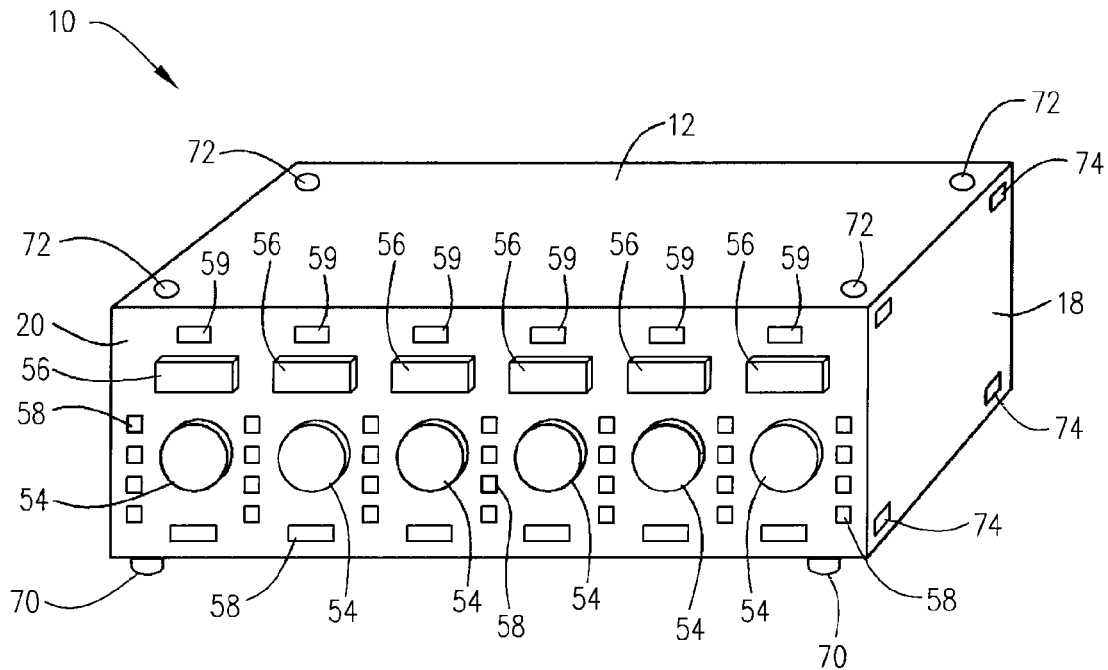
FIG. 3A is a perspective view of the staining apparatus of FIG. 2.

FIG. 3A shows a perspective view of the embodiment of the staining apparatus 10 of FIG. 2. The front wall 20 of the staining apparatus 10 comprises a plurality of slide support element doors 54 which can open (see FIG. 5) to allow the slide support elements 32 to be ejected from the staining apparatus inner space 24, or returned to the inner space 24. Similarly, the front wall 20 of the staining apparatus 10 comprises a plurality of reagent pack support device doors 56 which can open to allow the reagent packs 42 to be inserted into or ejected from the reagent pack support devices 34 for use in a treatment protocol, or after such use. Additionally, the reagent pack support device 34 can be constructed so as to be able to be ejected from the staining apparatus 10 through the door 56 (or without a door) for removal of a reagent pack 42 therefrom, or for placement of a reagent pack 42 thereon. The reagent pack support device 34 can then be returned (reinserted) into the inner space 24 of the staining apparatus 10 for treatment of the microscope slide 48 on the slide support element 32. The reagent pack support device 34 can, in an alternate embodiment, be positioned inside the staining apparatus 10 and only the reagent pack 42 is inserted into the reagent pack loading/removal opening (with or without an access door 56) wherein the reagent pack support device 34 "captures" or "grabs" the reagent pack 42 and pulls the reagent pack 42 into the staining apparatus 10 (like a CD-player in an automobile). When the reagent pack 42 is inside the staining apparatus 10 the microprocessor can recognize the reagent pack 42 and initiate the particular treatment protocol associated with that reagent pack 42. The reagent pack 42 may move outside and inside the staining apparatus 10 during staining to line up the desired reagent container thereon or can remain entirely inside the staining apparatus 10 during staining and only be moved outside of the staining apparatus 10 when ejected for disposal.

The staining apparatus 10 of FIG. 3A further comprises one or more of indicator lights, buttons, or gauges 58 and at least one display panel 59 which correspond to a particular slide support element, reaction compartment or reagent pack or reagent pack support device. For example, one indicator light, button (e.g., an eject/insert button), or gauge 58 may be used to cause a door 54 or 56 to open or close, or slide support element 32 to be inserted, or may indicate that the component is "on" or "off", or may indicate some physical parameter associated with the component, such as its temperature, pressure, or operational status. The display panel 59 may show the status or identify of the treatment protocol or reagent 38 to be used or currently in use in the reaction compartment 30.

Shown in FIG. 3B is a multi-staining apparatus version of the microscope slide staining system of the present invention designated by reference numeral 52 which comprises four staining apparatuses 10. Each staining apparatus 10 is indicated as containing 6 sets of reaction components 26. As noted above, the staining apparatus 10 may contain any number of sets of reaction components 26 (also referred to herein as reaction modules), for example from 4-50 sets and each microscope slide staining system of the invention may comprise one or more staining apparatuses 10. For example, in the microscope slide staining system 2 of the present invention, a single staining apparatus 10 may comprise the entire treatment unit of the staining system of the invention. The staining apparatus 10 may be arranged vertically of horizontally or in any configuration suitable for operating and the staining apparatus 10 may be constructed so that the sets of reaction components 26 are arranged in an arcuate pattern relative to one another within the staining apparatus 10 rather than linear.

Figure 4:
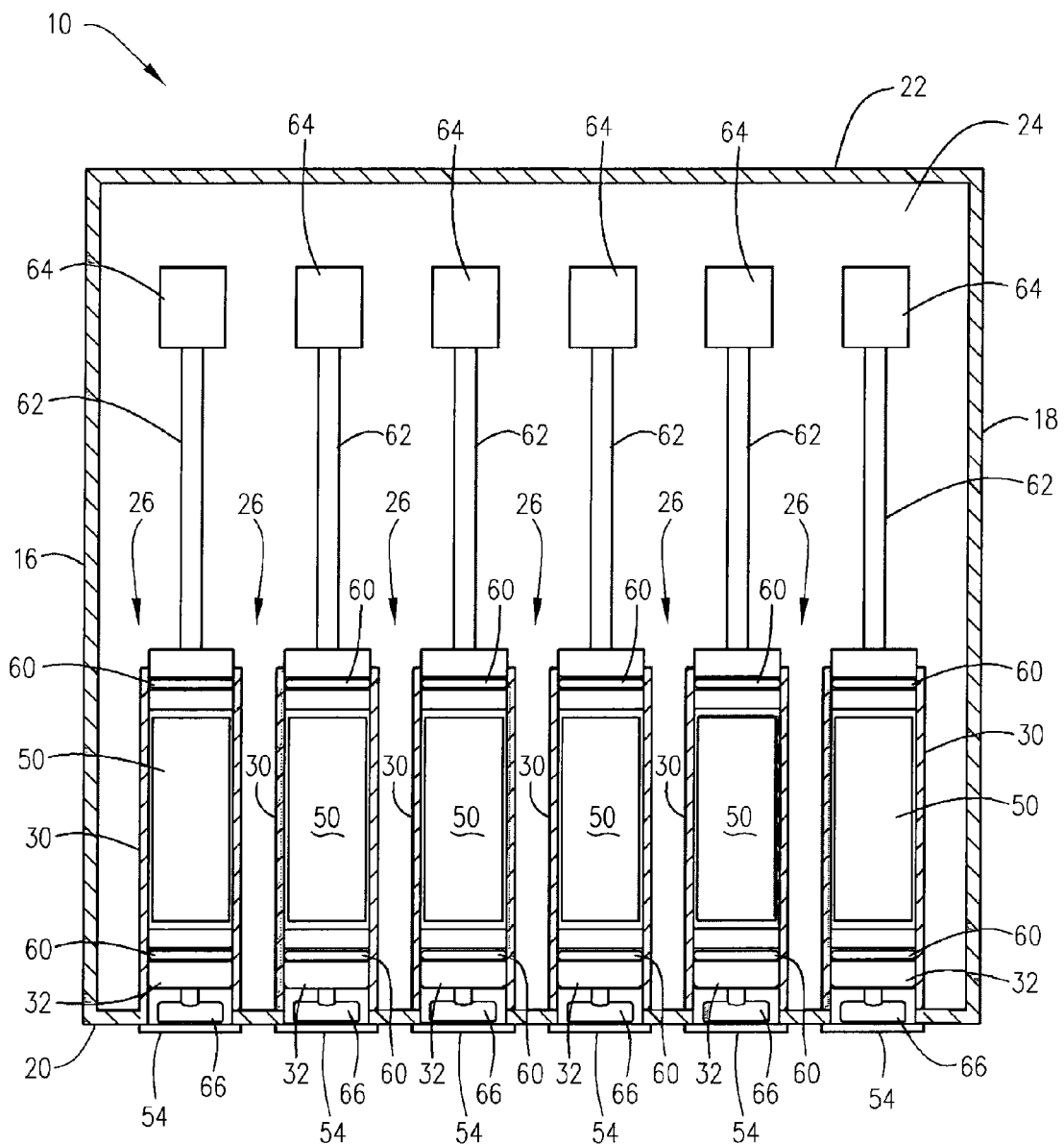
FIG. 4 is a top plan view of the staining apparatus of FIG. 3A.

Shown in FIG. 4 is a top plan view of the staining apparatus 10 of FIGS. 2-3B comprising reaction components 26 including reaction compartments 30, and slide support elements 32. Each slide support element 32 has sealing means 60 (such as O-rings or ground glass surfaces). Each slide support element 32 in this embodiment is connected by a shaft 62 to a motor 64 for pushing the slide support element 32 in a forward direction for ejection from the inner space 24 of the staining apparatus 10 and/or reaction compartment 30, for loading or removal of a microscope slide 48, or in a reverse direction for retracting the slide support element 32 into the staining apparatus inner space 24 and/or the reaction compartment 30 for treatment of the microscope slide 48. Optionally, each slide support element 32 may have a handle 66 for manually pulling or pushing the slide support element 32 into or out of the staining apparatus 10.

Figure 5:
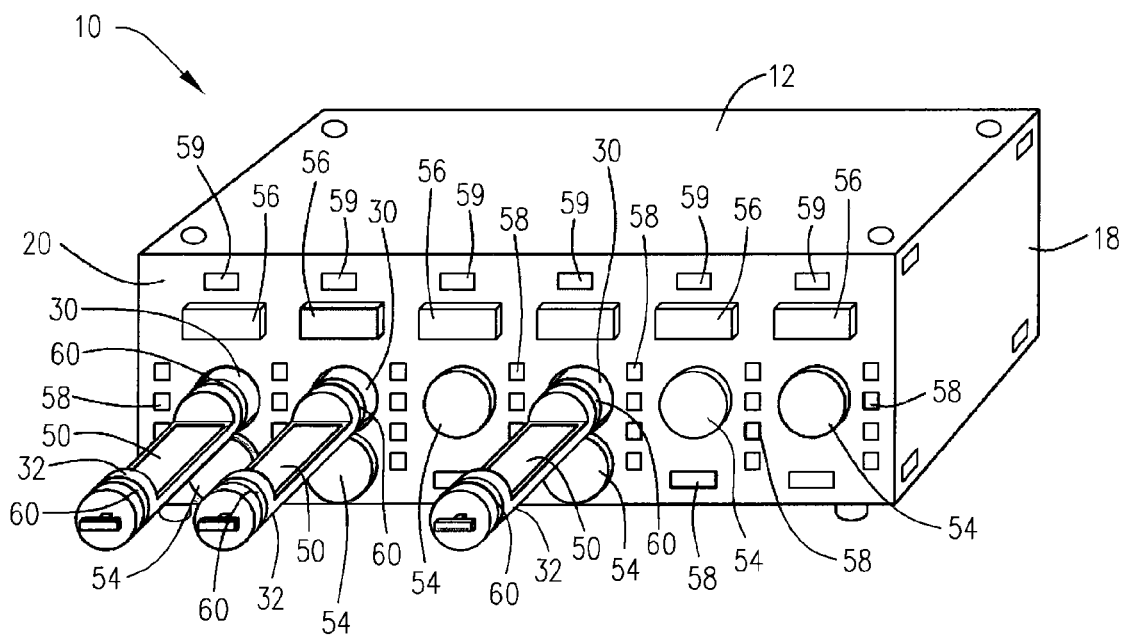
FIG. 5 is a perspective view of the staining apparatus of FIG. 3A shown as having three slide support elements ejected from the inner space of the staining apparatus.
Figure 6:
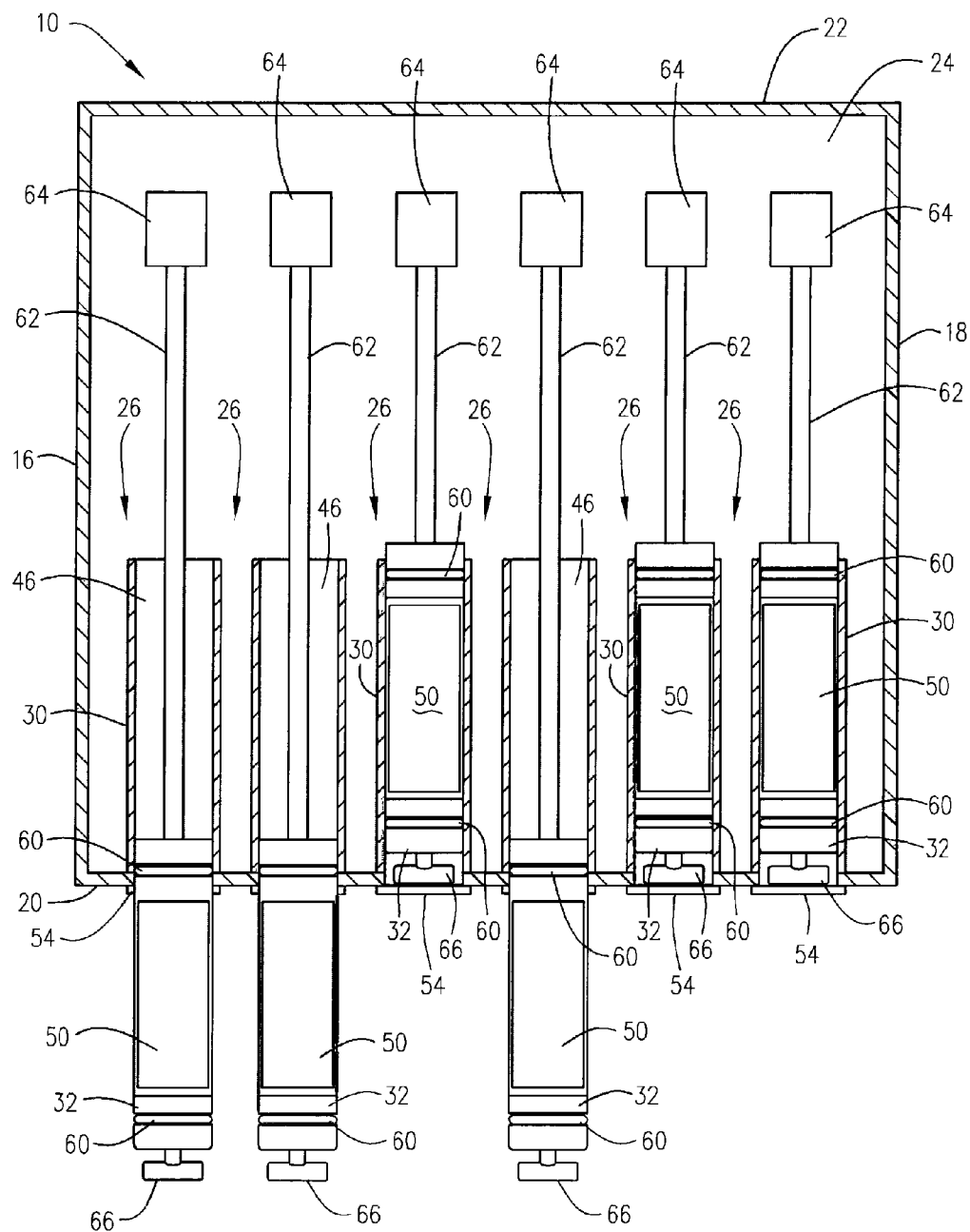
FIG. 6 is a top plan view of the staining apparatus of FIG. 5.

FIG. 5 shows the first, second, and fourth slide support elements 32 from the left ejected from the staining apparatus 10, in positions for placement of microscope slides 48 thereon. FIG. 6 is a top plan view of the staining apparatus 10 of FIG. 5 wherein the first, second and fourth slide support elements 32 from the left are shown in a placement or removal position outside of the inner space 24 of the staining apparatus 10. The motors 64 have caused extension of the shafts 62 causing expulsion of the slide support elements 32 from the corresponding reaction compartments 30, which in this embodiment are preferably open-ended.

The slide support elements of the invention preferably can be automatically moved in any position while the reaction compartment is pressurized (positively or negatively) with or without a heating means to heat the reagent under said positive or negative pressure. Said heating means can be a conductive, convective, and/or radiant heating element incorporated in or adjacent to the slide support element for heating the microscope slide and a biological specimen thereon. The slide support elements can be moved independently forward, backward, rotated along a longitudinal axis, and/or tilted, while the reaction compartment's inner space in under positive or negative pressure. Such movement of the slide support element, does not cause the positive or negative pressure to be expelled or otherwise "leak out" of the inner space of the reaction compartment since the slide support element is sealed therein. The seal of the slide support element to the reaction compartment causes retention of the pressure (positive or negative) held in the inner space of the reaction compartment during movement of the slide support element in within the reaction compartment.

This movement, which does not alter the pressure in the reaction compartment, would be advantageous when it is desired for the microscope slide to be moved when the reaction compartment is under positive or negative pressure, e.g., during a treatment protocol. For example, the reagent contacting the biological specimen on the microscope slide present on the slide support element can be mixed or agitated by mechanical movement of the slide support element under positive or negative pressure. This movement for mixing the reagent on the microscope slide can be, for example, a forward and alternating backward movement along with a tilting from side to side movement to cause a circular rotation of the reagent on the microscope slide. Further, the microscope slide can be rotated completely or partially to an upside down position (0° to 180° from its original upright horizontal staining position, for example) and rinsed under pressure to remove the reagent on the microscope slide. Any protocol step requiring movement of the slide support element under positive or negative pressure is contemplated. The movement contemplated above can be employed for mixing, rinsing, or otherwise treating the microscope slide with a protocol that has at least one step which benefits from, requires, or otherwise needs the microscope to be moved or mobile under positive or negative pressure, for example, for rinsing the slide and retaining the slide to the main treatment position. It also preferred that the slide support element is moveable at any time under or not under pressure. The slide support element can be moved forward, backward, and rotated 360° in relation to the stationary reaction compartment. Alternatively, the reaction compartment can also move relative to the stationary slide support element in a forward, backward, or 360° rotational movement.

In the staining apparatus of any of the embodiments contemplated herein the chamber may be constructed so that a portion of the front wall, upper wall, bottom wall, back wall, and/or side walls, can be detached or opened to enable access to the inner space of the staining apparatus for removal, replacement, repair, or insertion of any of the reaction components therein. For example, a portion of the front wall in front of a slide support element or reaction compartment can be removed to enable replacement thereof, without having to access or disturb other sets of reaction components.

In an alternate embodiment of the invention, the apparatus is an automated biological processing instrument having a pressurizable common chamber (e.g., see FIGS. 35 and 36) that can hold a plurality of microscope slides on a plurality of independently movable slide support elements in the pressurizable common chamber, wherein the slide support elements are automatically and independently movable inside the processing chamber while the common chamber is under positive or negative pressure with or without heating means to heat reagents on the microscope slides while under said positive or negative pressure. Said heating means can be a conductive, convective, and/or radiant heating element incorporated in or adjacent to the slide support element. The movements of the slide support elements are independent of each other while in the pressurizable common chamber and microscope slides therein are under positive or negative pressure. In an alternate embodiment, the slide support elements are positioned on a common platform which is movable, wherein a plurality of slide support elements under positive or negative pressure are movable together with or without heating means to heat reagents disposed on the microscope slides.

The automated biological processing apparatus contemplated herein can have movable biological processing devices (e.g., reagent dispensers) that move over or around the microscope slides on the slide support elements whether the microscope slides and slide support elements are movable (or in movement) relative to the processing devices or are in a fixed position while being under positive or negative pressure (and with or without a heating means to heat a reagent associated with the microscope slide). As contemplated herein, said biological processing devices can be (but are not limited to) reagent-air mixing gas jets, rinse dispensers, air knives for blowing off reagents, reagent dispensers to dispense reagents (such as antibodies, stains, molecular probes, detection reagents, RNA probes, DNA probes, in-situ hybridization reagents, evaporation inhibition oils, or detection reagents or other reagent elements contemplated herein), Optical Recognition Characters (ORC) code readers, machine readable devices to read codes or symbols, reagent spreaders, or any other processing devices known in the art of processing biological specimens on biological supports.

In preferred embodiments, the present invention comprises automatically, independently, and/or simultaneously movable slide support elements and/or automatically, independently, and/or simultaneously movable biological processing devices and/or reaction compartments, under positive or negative pressure which are operable while a reagent associated with a biological specimen on the microscope slide on the slide support element is being heated by a conductive, convective, and/or radiant heating element incorporated into or adjacent to the moveable slide support element and/or movable biological processing devices and/or movable reaction compartments. All such movable components present inside the staining apparatus of the apparatus can automatically move under positive or negative pressure wherein a reagent associated with a biological specimen on the microscope slide on the slide support element is heated by heating means present in or adjacent to the slide support element or microscope slide. Preferably these movements of the movable components present in the staining apparatus (or reaction compartments) under positive or negative pressure, with or without heat, do not release or otherwise change the positive or negative pressure within the staining apparatus (or reaction compartments) while the components are in motion.

Figure 34:
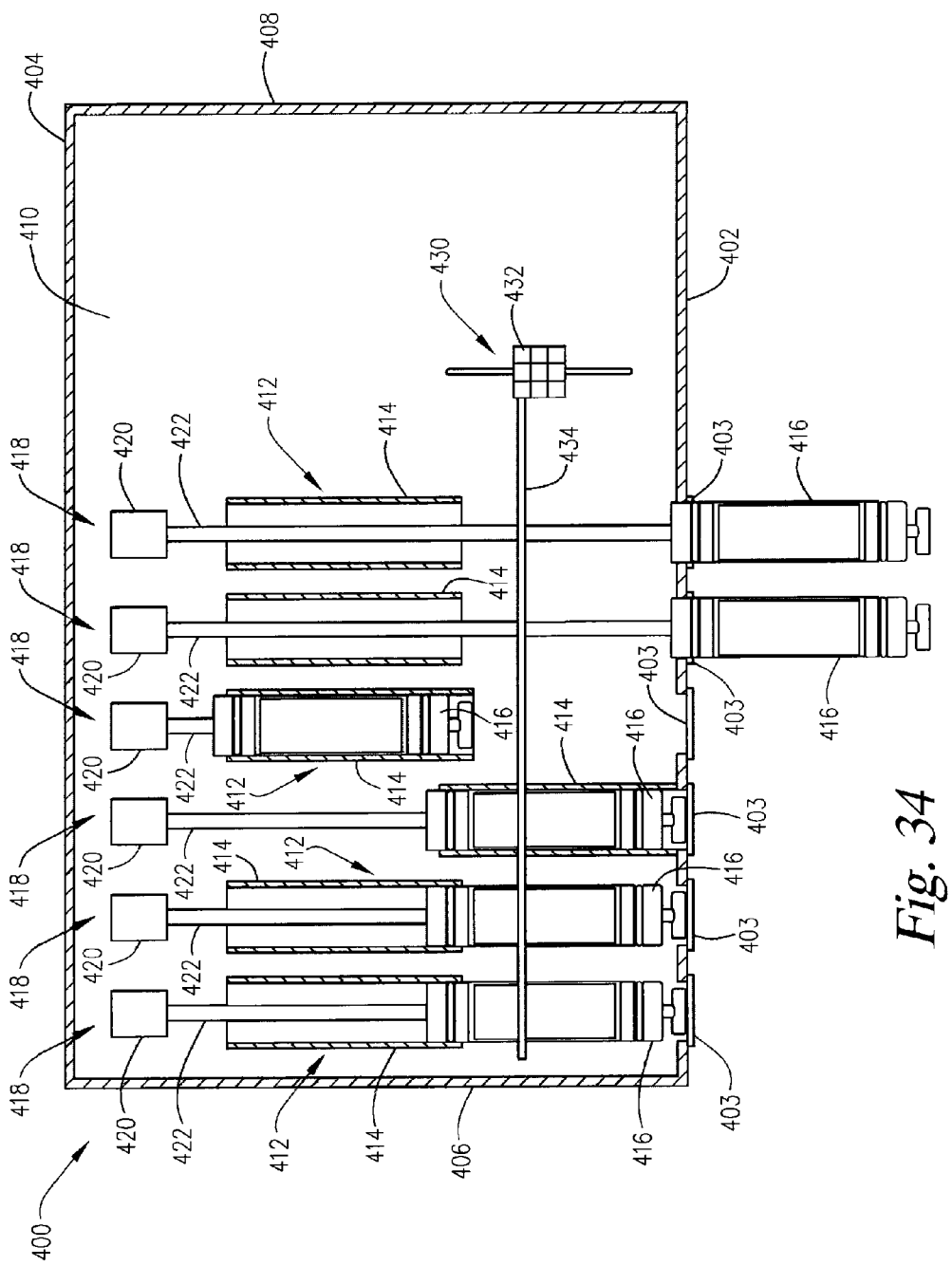
FIG. 34 is a top plan view of an apparatus of the invention similar to the apparatus of FIG. 4 except additionally having an X-Y-Z positioning apparatus comprising a dispenser head and a rotary reagent carousel comprising a plurality of reagent vials for dispensing reagents onto the microscope slides.
Figure 35:
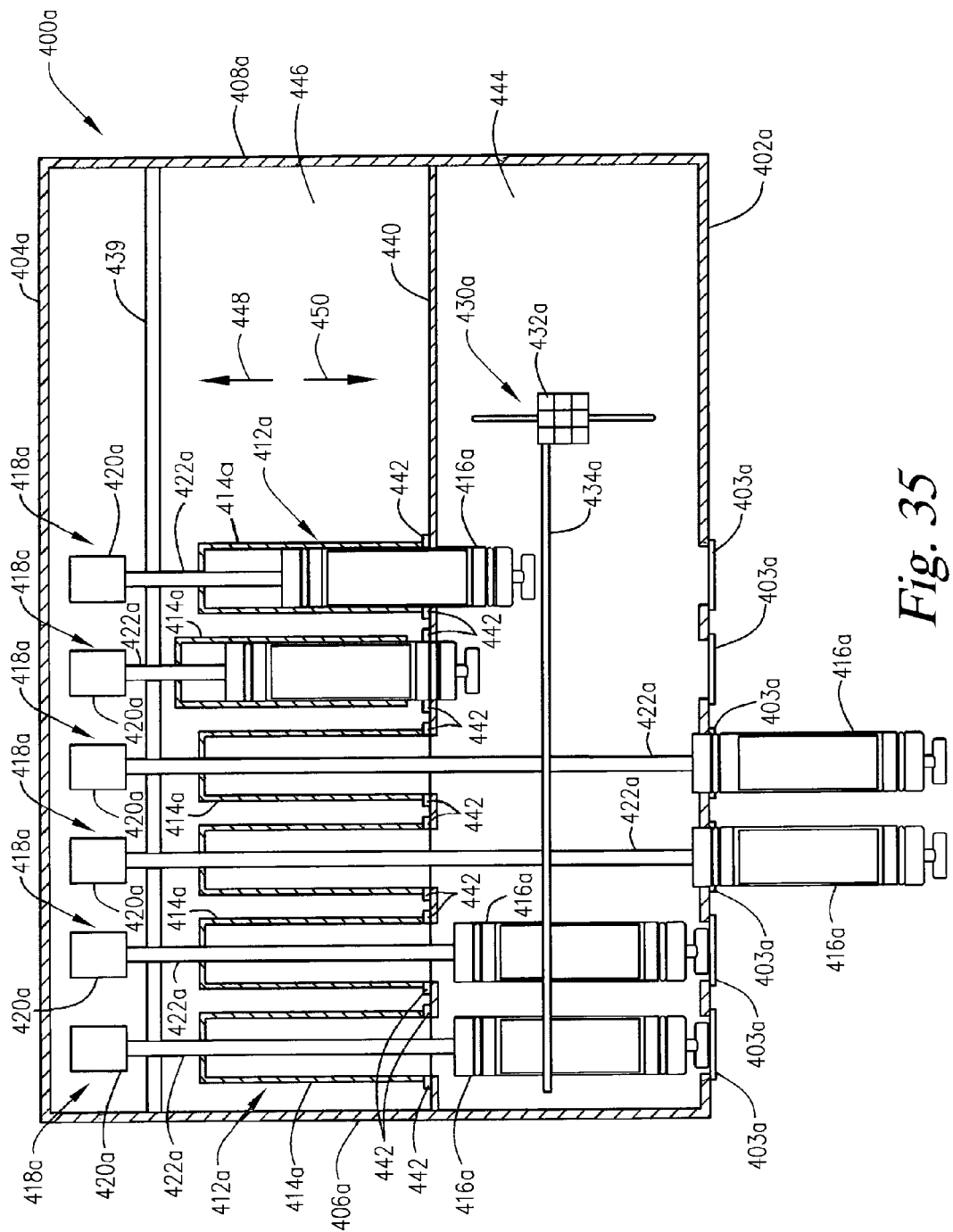
FIG. 35 is a top plan view of an apparatus similar to the apparatus of FIG. 34 except further having a separate pressurizable common chamber isolated from an application chamber in which reagents are applied to the microscope slides.

In an alternate embodiment of the invention, represented for example in FIGS. 34 and 35, the staining apparatus of the invention may comprise an X-Y-Z positioning device. X-Y-Z positioning devices are commonly used in the art of dispensing reagents to microscopes slides and other biological substrates. One commercially available X-Y-Z positioning device can be obtained from Tecan Group Ltd., 103 CH-8708 Mannedorf, Switzerland. The X-Y-Z positioning device comprises a movable head as a dispensing component and can be used to dispense reagents to the microscope slide on the slide support element outside or inside of the reaction compartment as described elsewhere herein. The X-Y-Z positioning device is able to move the movable dispensing component horizontally, laterally, or vertically to enable the movable dispensing head to be used as a dispensing device independently of the reagent pack or as an adjunct thereto.

This embodiment may use the reagent pack to dispense reagents in addition to reagents dispensed directly from the X-Y-Z positioning device. The dispensing head of the X-Y-Z positioning device can dispense reagents through conduits therein, as for the dispensing plunger which causes expulsion of reagents from the reagent pack. The dispensing head may comprise a distal portion forming a dispensing head which may have a pipette attached for dispensing reagents from an array of containers or the distal position could have disposable pipette tip attached that can be used and removed between application of each reagent. The dispensing head of the X-Y-Z positioning device can, in one embodiment, be used as the dispensing plunger to dispense reagents from the reagent pack or as an inkjet printer, an optical code reader, a scanner, or an aspirator.

All the heating elements of the present invention (e.g., the slide heater, reaction compartment heater, dispensing port heater, cavity heater, reagent strip holder heater, and the slide support heater (described below)) can be adapted to heat and sustain heating from about 1° C. to about 1000° C. The temperature of the reagent in the reaction compartment can be in the range of ambient, (25° C.) or heated to 100° C. or greater. The reagent is preferably in the range of 25° C. to 400° C., and is more preferably in the range of 25° C. to 150° C. The temperature of the reagent when heated is preferably in the range of 100° C. to 160° C. More preferably, the temperature of the reagent is in the range of 101° C. to 150° C. More preferably, the reagent temperature would b in the range of 110° C. to 130° C. The reaction compartment can be pre-pressured by a separate gas source described in US Pat Applications 20060281116, 20060275889, and 20060275861 or the pressured gas can be produced by the compression of the "head space" of the reaction compartment described in detail below. The pre-pressure gas sent to the reaction compartment is also known as "pre-reaction pressure" The reaction compartment can have further pressure produced from the evaporation of the liquid reagent present on or around the microscope slide. An example being, the separate source of gas being brought to the reaction compartment to pre-pressurize the reaction compartment is say 25 psig. The heating source would heat the reagent around the microscope slide and/or heat the reagent on the microscope slide. The evaporating reagent around the microscope slide and/or the reagent on the microscope slide produced an additional 5 psig, for example. The total psig, for example, would be the initial 25 psig from the pre-pressure source plus the psig from the evaporated reagent totals 30 psig. This addition of the separate source of gas and the addition of the evaporated reagent total is known as the "total reaction pressure" or "TRP". The evaporating reagent producing pressure is directly related to the type of reagent being heated and its evaporation characteristics. The reagent evaporation pressure can be in the range of 0-10 psig, for example. Pressures for pre-pressurization, regular pressurization or in-situ pressurizations can be in the range of 0.01 PSIG to 1000 PSIG, more preferably in the range of 1 to 500 PSIG, and still more preferably, in the range of 10 to 150 PSIG.

In an alternate embodiment of the present invention, each of the slide support elements can support at least two microscope slides. Preferably each separate microscope slide would be heated by separate heating elements, but they could be heated by a common heating element. This slide support element which is able to hold at least two microscope slides would have a single reaction compartment for pressurized treatment of the at least two microscope slides on the single slide support element. This embodiment is optimally used in high volume microscope slide testing laboratories, wherein instead of one slide per slide support element and each slide support element having its own single reaction compartment, this embodiment would result in a decrease of the number of slide support elements which carry only a single microscope slide per slide support element. For example, in this embodiment, the staining apparatus could comprise 10 slide support elements each able to hold at least two slides. If the staining apparatus had 10 of these double slide support elements these 10 slide support elements would support 20 slides together if they were all in use for an initial treatment run of these 20 microscope slides. Preferably the staining apparatus would also comprise a plurality of slide support elements which support single microscope slides enabling the addition or removal of single slides onto and into the staining apparatus for independent access to the staining apparatus. Thus, individual single slides could be inserted or removed from the staining apparatus while the other double slide supports were already in operation. For example, in one embodiment of a staining apparatus able to treat 40 slides, there could be 10 double slide support elements holding 20 slides, and 20 single slide support elements for independent access to 20 slides enabling a total of 40 slides to be treated. The staining apparatus could comprise any combination of double, triple, (or more) slide support elements along with a plurality of single slide support elements in any combination of single or plural slide support elements. As stated above, if a slide support element is sized to support 2 or more microscope slides, this slide support element would have its own reaction compartment unique to itself for treatment of the slides thereon. If a movable slide support element, for example, held 3 microscope slides, this slide support element would be associated with its own reaction compartment for the pressurized treatment or treatment of the 3 slides present thereon. In an alternate embodiment, the staining apparatus may comprise separate reaction compartments that separately enclose or at least partially enclose the at least two or more microscope slides on the single slide support element, thereby enabling separate treatment of the at least two or more microscope slides even though they are movable together on the common slide support element. In an alternative embodiment the at least 2 microscope slide support elements can be moved into or out of a staining apparatus having a pressurizable common chamber for treatment of the microscope slides along with any single slide support element that is also capable of moving into or out of the staining apparatus with the pressurizable common chamber.

Embodiments of FIGS. 7-22B

Figure 7:
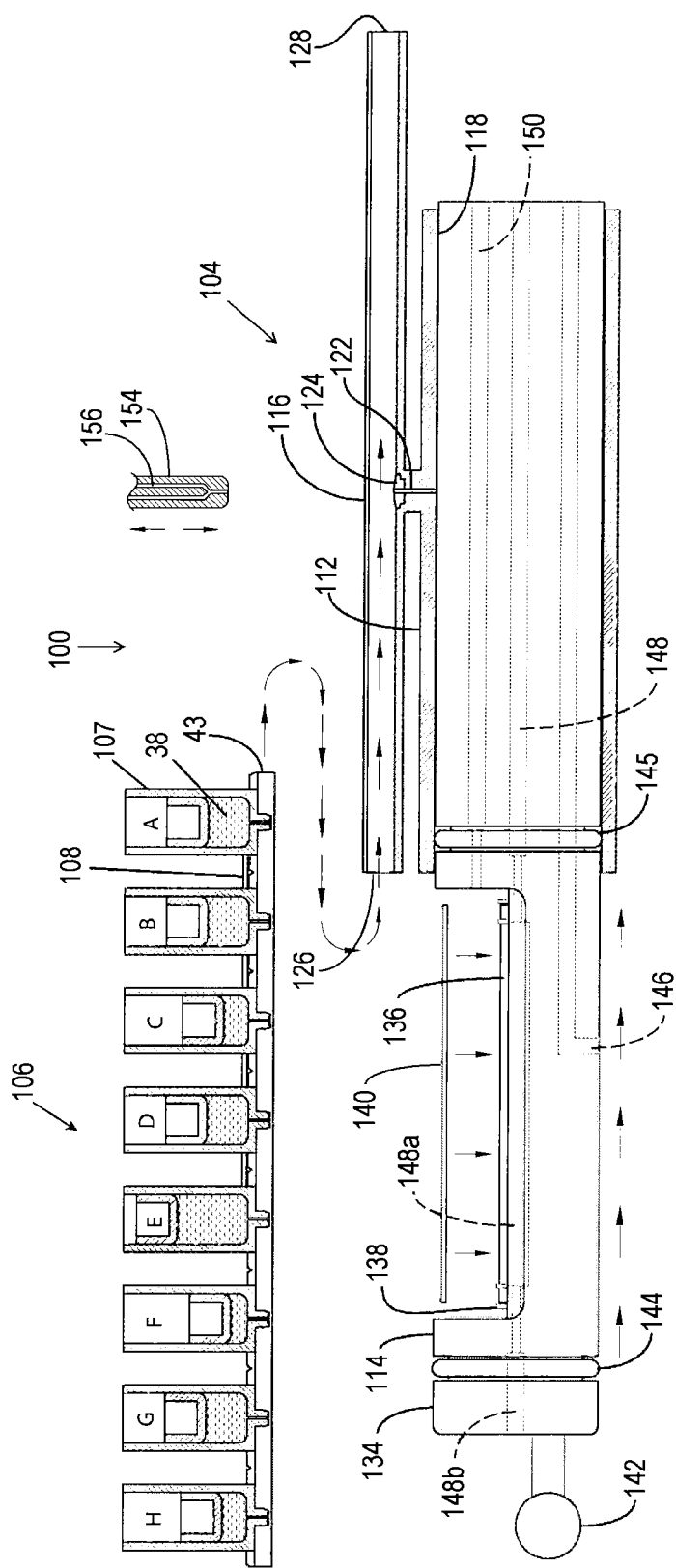
FIG. 7 is a cross-sectional side view of a set of reaction components (e.g., reaction compartment, slide support element, and reagent pack support device) in a staining apparatus of the present invention before the reagent pack has been inserted into the reagent pack support device, and before a microscope slide has been disposed on the slide support element. The walls of the staining apparatus are not shown for simplification.

Shown in FIGS. 7-22B are reaction components 104 of a staining apparatus 100 such as staining apparatus 10 of an analytic apparatus of the present invention having a cylindrical reaction compartment 112, a slide support element 114, and a reagent pack support device 116 for supporting a reagent pack, such as previously described elsewhere herein. Preferably, the reaction compartment 112 has an inner diameter of 1.5-5 cm, and more preferably 2-3 cm, and more preferably 2.5-2.8 cm, and has a wall thickness of 2 mm to 3 mm. The length of the slide support element 114 is preferably 10-20 cm, and more preferably 12-15 cm. The length of the reaction compartment 112 is preferably 15-30 cm, and more preferably 18-22 cm. The reagent pack support device 116 in this embodiment is operatingly connected (e.g., attached at a top) to the reaction compartment 112 via a reagent conduit 122 in the reagent pack support device 116 or reaction compartment 112 which opens to an inner space 120 of the reaction compartment 112. There is an injector port orifice 124 in the reagent pack support device 116 which is adapted to receive an injector nozzle or port from a reagent container of a reagent pack 106. The reagent pack support device 116 has a front end 126 and a rear end 128. The reagent pack support device 116 functions to receive, support, move and eject a reagent pack 106 of the present invention and preferably can move upwardly and downwardly and forward and backward. The slide support element 114 has a base 134 which can reciprocatingly move into and out of the reaction compartment 112 and into or out of the staining apparatus 100. The slide support element 114 comprises a heating element 136 upon which a microscope slide 140 (like microscope slide 48) is placed. The slide support element 114 may optionally have a handle 142 which enables a technician to manually insert and withdraw the slide support element 114 from the reaction compartment 112 and staining apparatus 100. The slide support element 114 preferably further comprises a sealing means which in the embodiment of FIG. 7 is a front O-ring 144 and a rear O-ring 145 for providing a pressure resistant seal of the base 134 against the inner surface 118 of the reaction compartment 112. Other embodiments of sealing means which can be employed in the invention are described elsewhere herein. The slide support element 114 (and base 134) can be constructed from materials which include, but are not limited to, glass, quartz, Pyrex®, borosilicate, steel, metals, aluminum, composites, polymers such as polycarbonate and plastics or combinations thereof.

The slide support element 114 also preferably has a drainage port 146 for receiving and draining reagents and waste liquids from the reaction compartment 112. The slide support element 114 further preferably has one or more cooling ducts 148 which are operatively connected to a sub heating element cooling space 148a beneath the heating element 136, and one or more cooling duct exits 148b which evacuate the cooling air or liquid from the sub heating element cooling space 148a. The slide support element 114 preferably further comprises a first air/pressure duct 150 and a second air/pressure duct 152 for regulation of the pressure within the reaction compartment 112 as discussed elsewhere herein. The duct 150 and/or duct 152 or an additional duct (not shown) can be used for releasing and/or regulating pressure from the reaction compartment 112. The slide support element 114, as noted above, comprises a heating element 136 upon which the microscope slide 140 is placed for application of reagents thereon. The reaction components 104 may further comprise a thermocouple or other temperature measuring device for measuring temperatures of the slide or other components therein. Before operation the slide support element 114 is inserted by a sliding motion into the inner space 120 of the reaction compartment 112 (see FIG. 8A-8B). Also before operation the reagent pack 106 (or any other reagent pack described or enabled herein) is inserted into the reagent pack support device 116, for example, inserting a first end 43 of the reagent pack 106 into the front end of 126 of the reagent pack support device 116, wherein during operation the reagent pack 106 is moved in a direction toward the rear end 128 of the reagent pack support device 116. The reagent pack 106 may be advanced manually or automatically via a pulling or pushing device, including rollers or a track which incrementally advances the reagent pack 106 as instructed by a microprocessor. The reaction compartment 112 further comprises a reagent conduit 122 (like reagent conduit 44) for allowing passage of a reagent from the reagent pack 42 into the reaction compartment 112. The reaction components 104 also comprise a dispenser plunger 154 (also referred to herein as a dispensing element and similar to dispenser plunger 36 above), which has a dispensing canal 156 therein for allowing passage of another reagent or solution therethrough preferably from a remote source. The reagent pack support device 116 preferably has an injector port orifice 124 for receiving at least a portion of an injector nozzle 46 from a reagent container 107 of the reagent pack 106 during use thereof.

The staining apparatus 100 may comprise a separate device (other than a dispensing element) for pressing reagents from the reagent pack 106 such as shown in the embodiments of FIGS. 29A-33H.

Figure 12:
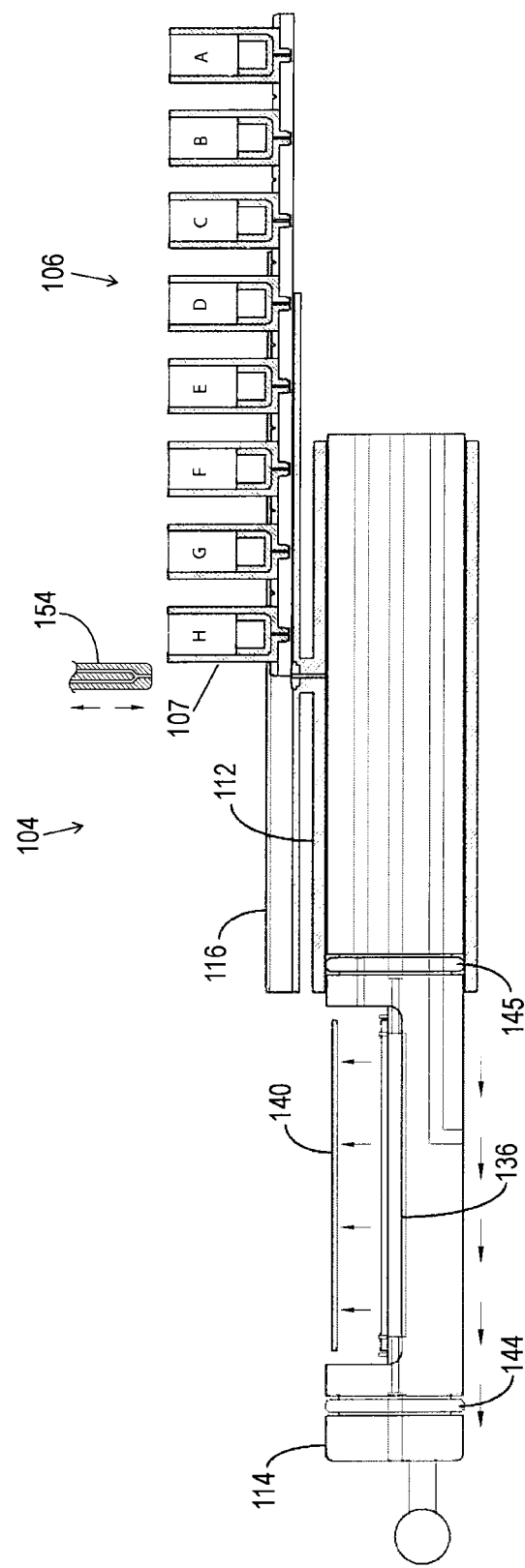
FIG. 12 is a cross-sectional view of the reaction components of FIGS. 7-11B after the reagent pack is completely used and the microscope slide is removed from the slide support element.
Figure 13:
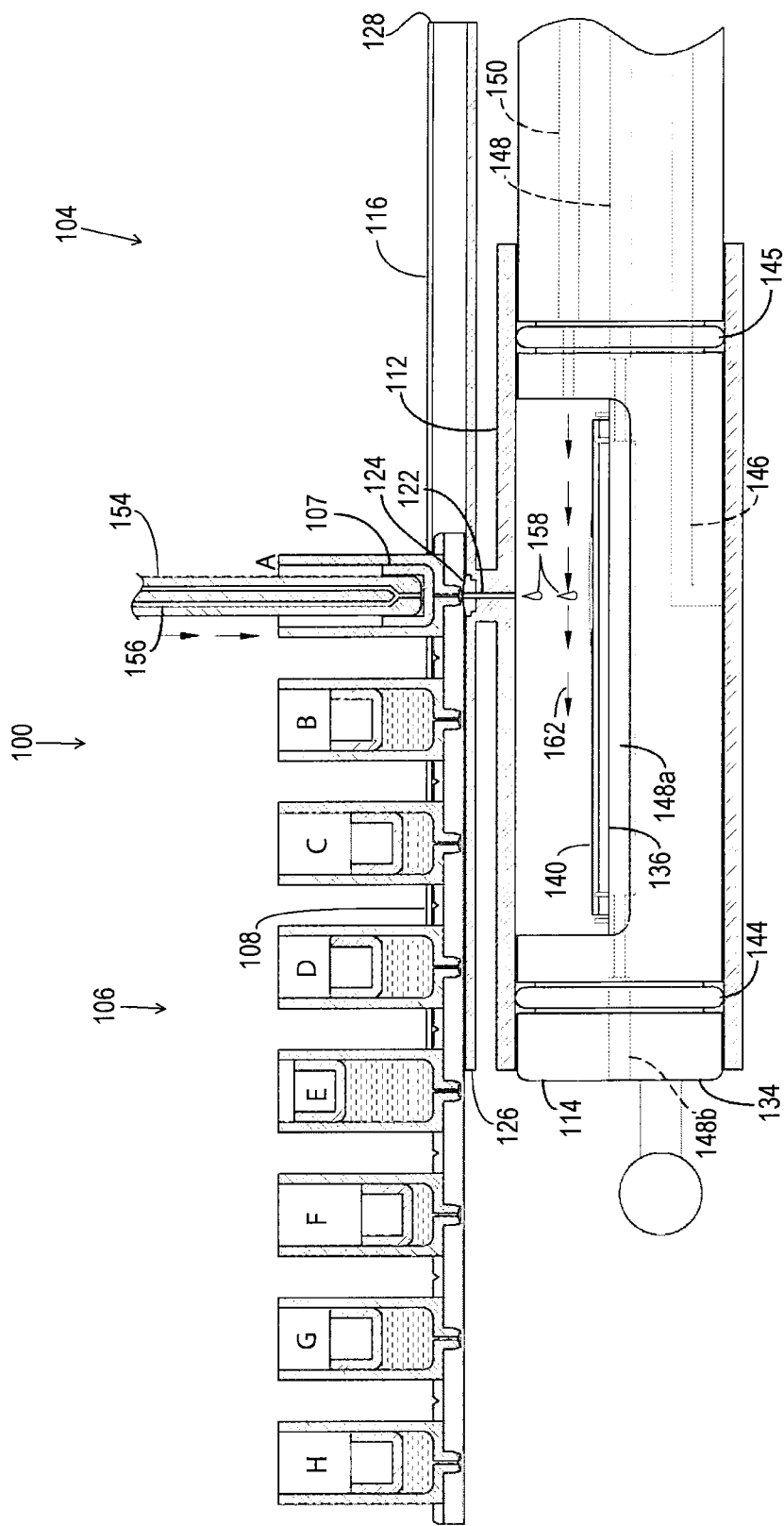
FIG. 13 is an enlarged version of FIG. 8A.
Figure 14:
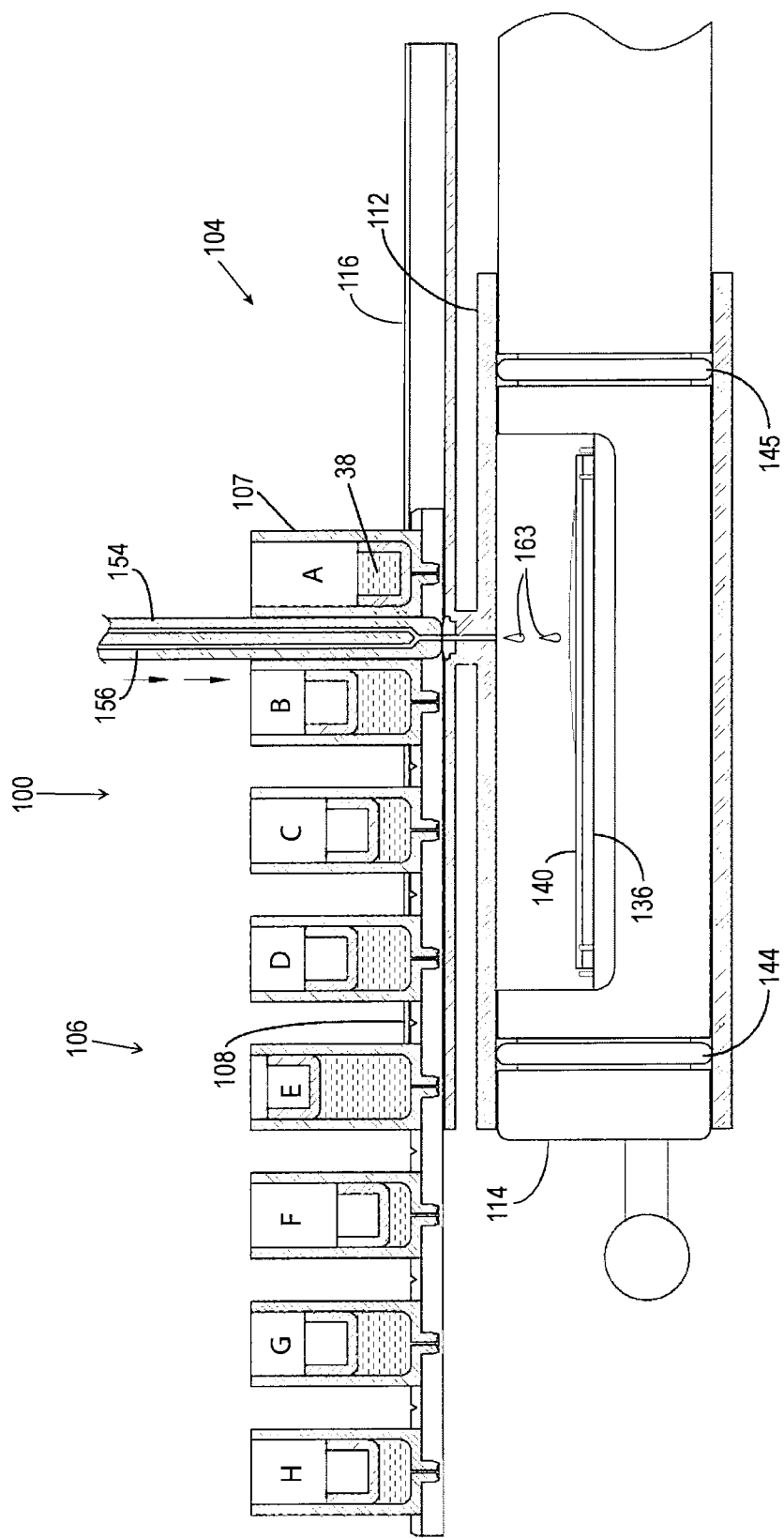
FIG. 14 is an enlarged version of FIG. 10A.

During operation, as shown in FIGS. 8A-8B and 13, a reagent pack 106 (or any other reagent pack described or enabled elsewhere herein) is inserted through a door not shown in front wall 102 into the reagent pack support device 116 as previously described and a reagent container 107 is positioned over the injector port orifice 124. The dispensing plunger 154 is extended downwardly into the reagent container 107 of the reagent pack 106 wherein it engages a piston, forcing the piston downwardly and causing ejection of the reagent 38 from the container 107 through the reagent conduit 122 and providing reagent 38 deposited onto the microscope slide 140. When the dispensing plunger 154 forces the piston 44 downwardly, a seal is maintained within the reagent container 107 and in a preferred embodiment enables maintenance of pressure within the reaction compartment 112. The reagent 38 can be mixed on the microscope slide 140, for example, by delivering bursts of air 162 through the first air/pressure duct 150 and the second air/pressure duct 152 as discussed in further detail below. In a subsequent step the dispensing plunger 154 may be withdrawn (FIG. 9A-9B) and the base 134 of the slide support element 114 tilted within the reaction compartment 112 to allow the reagent 38 to drain from the microscope slide 140, forming a reagent drainage 160 which is collected in the drainage port 146, removed from the reaction compartment 112, and collected in a waste storage container (not shown). In a later step (FIGS. 10A-10B) the slide 140 is returned to an upright, horizontal position and the reagent pack 106 is advanced until the rinse port aperture 108 in the reagent pack 106 is positioned above the injector port orifice 124 wherein rinse solution 163 is delivered from a rinse solution reservoir (not shown). Furthermore, air or liquid may be delivered through the dispensing canal 156 in the dispensing plunger 154 to cause mixing of reagent 38 or to remove the reagent 38 from the microscope slide 140, or to enhance the rinsing of the reagent 38 or rinse solution 163 from the microscope slide 140 (e.g., see FIGS. 11A-11B). Finally as shown in FIG. 12, after all reagents from the reagent pack 106 have been dispensed, the portion of the slide support element 114 which carries the microscope slide 140 is withdrawn from the reaction compartment 112 wherein the microscope slide 140 is then removed from the slide support element 114. Note that FIGS. 13-14 are enlarged versions of FIGS. 8A and 10A, respectively and are provided herein for the purpose of more easily showing the steps therein.

FIGS. 15A-16B provide a more detailed description of how the bursts of air 162 delivered form the first air/pressure duct 150 and second air/pressure duct 152 can be used to cause mixing of the reagent 38 on the microscope slide 140. Preferably, the first air/pressure duct 150 and second air/pressure duct 152 are operated alternately to provide bursts of air 162 in alternating clockwise/counterclockwise directions to agitate the reagent 38. The first air/pressure duct 150 and second air/pressure duct 152 can also be used to pressurize the reaction compartment 112. At any desired time the heating element 164 can be used to heat the slide 140 and reagent 158 thereon as discussed in greater detail elsewhere herein. As shown in FIGS. 17-19B, after the microscope slide 140 is heated, it can be rapidly cooled by directing air or liquid via the cooling ducts 148 into sub heating element cooling spaces 148a which are located below the heating element 164 which in one embodiment is located below and is used to heat a hot plate 166 upon which the slide 140 is positioned. Air or liquid used for cooling can then pass through cooling duct exits 148b. In another embodiment, shown in FIGS. 20-22B a sub heating element cooling space 148c is similar to sub heating element cooling space 148a except the cooling air or liquid which passes through the sub heating element cooling space 148c is delivered via one of the cooling ducts 148 and exits the slide support element 114 via the outer cooling duct 148.

As shown in FIGS. 7-22B, each reaction compartment 112 of the staining apparatus 100 preferably comprises a hollow cylinder, preferably constructed of a thermoplastic resin or polymer (including but not limited to polycarbonate or any other polymeric material able to withstand elevated temperatures and pressures), glass, Pyrex®, quartz, other crystalline materials, and metals and metal alloys. The tubular nature of the reaction compartment 112 is preferred because the elevated pressures created within the reaction compartment 112 during its use are more evenly distributed therein.

The seal between the outer surface of the slide support element 114 and the inner surface of the reaction compartment 112 can be formed using O-rings, as shown in the FIGS. 23-38B or can be formed using an inflatable O-ring, a seal, or an inflatable seal depending on the shape of the mating surfaces. The sealing means can be constructed of plastic, polymer, thermoplastic, resin, ceramic, rubber, metal glass, or composite, for example.

Or in a preferred embodiment, sealing surfaces comprising an outer surface portion of the slide support element 114 and an inner surface portion of the reaction compartment 112 are made of a low tolerance ground or polished sealing surface. These sealing surfaces when engaged from a seal which replaces and eliminates the need for a ring seal or inflatable or seal raised above the mating surfaces. In this embodiment, the ground or polished mating surfaces alone, when joined together, produce a microscopic seal with a large surface area to seal the microscope slide within the reaction compartment 112 and which is able to maintain an elevated pressure therein (above atmospheric) even under high temperature conditions above 100° C. The material of the slide support element 114 and the tubular reaction compartment 112 can feature a very high tolerance ground or polished seal on the mating surfaces. In the preferred embodiment, the slide support element 114 and the reaction compartment 112 are made of a high tempered glass material like Pyrex®, or any material that can produce a ground or polished mating surface to form a seal which maintains a pressure above atmosphere pressure. The ground glass surface, or polished surface of the slide support element 114 against the ground or polished surface of the reaction compartment 112 yields an air-tight and pressure-tight seal when the two ground or polished surfaces are joined together, such that, there is no void space which must be filled by a raised surface such as an O-ring. This embodiment of the present invention thus eliminates the need for raised seals (e.g., O-rings) thus reducing maintenance cost for the replacement of separate seal components such as O-rings and increases simplicity and efficiency and seals the reaction compartment even under pressures above atmospheric levels (e.g., above 14.7 psig (101.325 kPa), i.e., above 0 psig (101.325 kPa)) and high temperature conditions above 100° C.

As noted herein, the staining apparatus (e.g., staining apparatus 10 or 100) of the staining apparatus of the present invention preferably comprise a plurality of sets of reaction compartments 112, such as shown in FIG. 7. Each set of reaction components 110 comprises a tubular reaction compartment 112 (although the reaction compartments may not be tubular, but may be rectangular, a slide support element 114 and in a particularly preferred embodiment a reagent pack support device 116. The reaction compartment 112 has an inner surface and an inner space into which the slide support element 114 can be moved for treating a biological sample on a microscope slide 140 thereon. The slide support element 114 is able to slide into and out of the reaction compartment 112 in a manner similar to a piston within a cylinder. When the slide support element 114 is withdrawn from the reaction compartment 112 and/or from the staining apparatus 100, a microscope slide 140 can be placed thereon or removed therefrom. The slide support element 114 can be inserted into the reaction compartment 112 for treatment of the biological sample on the microscope slide 140 as described elsewhere herein. As shown below, the slide support element, in a preferred embodiment) can be turned (tipped or rotated) within the reaction compartment 112 for facilitating the removal of reagents or fluids from the microscope slide 140 after the microscope slide 140 has been treated, as shown in the figures (e.g., see FIG. 9B). Reagents or fluids on the microscope slide 140 can be mixed by air circulation as shown in FIGS. 15A-16B for example or by rotational movement of the slide support element 114. After heating, the microscope slide 140 can be cooled by circulation of air or fluid thereunder, for example as shown in FIGS. 18A-22B. In another embodiment, the microscope slide 140 could be cooled by using a circulating liquid such as a reagent that becomes pre-heated by passing under the heated slide thus transferring heat to the circulating reagent which could then be dispensed onto the microscope slide 140.

The reaction compartment 112 of the present invention (or other reaction compartments) can be constructed of any material known in the art of high temperature and pressure compatible devices. These materials also include, but are not limited to, plastics, polymers, composites, ceramics, glass, quartz, metals and coated metals. The components of the reaction components 112 can be coated for resistance to porosity, to increase hydrophobic and hydrophilic properties, for ease of cleaning, chemical resistance, and stain resistance. These coatings could be, for example, Teflon®, fluoropolymers, any other known coating that would impart these desirable properties to all surfaces of reaction compartment 112 and slide support elements 114 and surrounding structures with a different coating being present on different portions of the apparatus. In one embodiment, for example, the inner surface of the reaction compartment 112 and outer surface of the slide support element 114 may be coated with a hydrophobic, chemical, and stain resistant coating to aid in the draining of the condensed reagents on the inner surface of the reaction compartment 112 or outer surface of the slide support elements 114 and ease of removal of reagents therefrom.

The slide support element 114 preferably has incorporated therein a heating element 136, and a hot plate (which may be one and the same) and which may include guide clips or pegs or elements to position and secure the microscope slide thereon. The tops of the clips may be positioned to be below an upper surface of the microscope slide, so as to prevent reagent on the slide 140 from being wicked off by the clips by capillary action.

In a particularly preferred embodiment, underneath the heating element 136 is one or more recessions (sub-heating element cooling spaces 148a) which are connected via cooling ducts 148 to a gas or liquid supply source to quickly cool the heating element 136 thereby quickly cooling the microscope slide and the reagent thereon.

The slide support element 114 and reaction compartment 112 can be constructed of any material suitable for use under pressurized conditions and resistant to corrosion by laboratory reagents, including but not limited to stainless steel, metals, plastics (clear or opaque), polymers (e.g., polycarbonate), tempered glass, and Pyrex® or other materials mentioned herein.

Containment of waste and used reagents from the staining apparatus will be now briefly discussed, (see further discussion above).

In a preferred embodiment the staining apparatus of the present invention (e.g., as represented in FIG. 1) has a waste collection system 6 which is operatively connected to the reaction components of the staining apparatus 10 by one or more fittings that can join multiple tubes or conduits. In a preferred embodiment of the present invention, this main fitting (not shown) can be joined to the waste container of the waste collection system (waste module) 6 (which may be disposable or non-reusable) by a breakable joint present on the waste container. This fitting on the waste container snaps together with the main fitting of the instrument. This attachment is secure and will not leak under pressure. When detached, this fitting on the waste container partially "breaks away" and leaves behind on the waste container an airtight, leakproof, tamper proof, non-removable seal. The residual piece that was detached from the waste container is removed by the technician and then is ready to be reattached to a new waste container. The waste container is now ready to be disposed of in its entirety by a technician or medical waste personnel. The tamper proof seal of the separated fitting protects the medical waste personnel from coming in contact with any of the waste in the sealed waste container.

In an alternate embodiment the detachable fitting on the waste container may not have any residual piece on the main instrument fitting but rather "breaks" or "snaps" away form the detachable piece on the disposable waste container cleanly.

In an alternate embodiment, the waste module 6 could comprise two or more waste containers wherein it is possible to remove one full waste container while retaining one or more other waste containers attached to receive waste from the working reaction modules. The microprocessor could alert the technician that a waste container is in need of replacing by a sensor located in the waste container. If the technician chooses to ignore the alert from the instrument, it could divert the waste to another waste container until the time is convenient to replace the full waste container. Since the staining apparatus operates each set of reaction components independently, the waste containers are set-up to receive waste from any one or more of the reaction components during operation thereby eliminating the need to stop operation of the instrument just to change any full waste container. The waste containers can be hooked up in a series or in parallel, as explained above) to keep at least one waste container active while any other waste container is being changed. The microprocessor is preferably in direct communication with all the waste containers and will shut down any waste route that leads to a fitting that has been detached and is in the process of replacement, repair, or cleaning.

In an alternate embodiment, the staining apparatus could have one main waste container which when full would alert the technician to start the waste recovery procedure. The main waste container could be drained to a secondary waste container to be disposed. The waste container can be charged with activated charcoal or other neutralizing chemicals to aid in decontamination. The waste container can have a vent that has a neutralizing filter to release the build up of pressured vapors.

Turning again to the figures, it will be shown in greater detail how the sets of reaction components 104 (and others described herein) operate.

As explained above, an exemplary operation sequence of the reagent pack 106 with the sets of reaction components 104 is generally shown in FIGS. 7-22B.

The microscope slide 140 is loaded onto the heating element 136 of the slide support element 114 and positioned by location clips 138 or guide pegs or other orientation elements to verify proper location of the microscope slide 140 on the slide support element 114. The slide support element 114 and microscope slide 140 is then moved into the reaction compartment 112 wherein it is sealed via the O-rings 144 and 145 (or other sealing means contemplated herein). The reagent pack 106 is placed onto the reagent pack support device 116. The protocol is entered either automatically or manually (described elsewhere herein) and the apparatus or staining apparatus 100 with the plurality of reaction components 104 is instructed to start. Depending on the protocol the heating element 136 can start to heat the microscope slide 140 or the protocol instructs the dispensing of a reagent from the reagent pack 106 or from another source (e.g., a remote bulk source or X-Y-Z positioning device as discussed elsewhere herein) via the dispensing plunger 154.

If an individual reagent container 107 located on the reagent pack 106 is selected, that particular reagent container 107 will be positioned over the injector port orifice 124 (over the microscope slide 140 outside of the reaction compartment 112), and the dispensing plunger 154 and depresses the piston within the reagent container 107 to expel the reagent 38 therefrom onto the microscope slide 140. The reagent pack 106 would then be moved to position the rinse port aperture 108 in the reagent pack 106 (e.g., generally located between adjacent reagent containers 107) over the injector port orifice 124 wherein the dispensing plunger 154 would be lowered to seal the injector port orifice 124 or, additional air or reagent could be injected into the reaction compartment 112. Once the reagent 158 which has been applied to the microscope slide 140 is removed from the microscope slide 140 by tilting the microscope slide 140 or by rinsing, the microscope slide 140 can be further rinsed with a reagent or treated with pressurized air from the dispensing plunger 154.

As discussed elsewhere herein, the reaction compartments of the present invention can be pressurized (positively or negatively) during heating of the reaction compartment or can be pressurized without heating, or pre-pressurized (positively or negatively) before the microscope slide or other reaction component is heated. The reaction compartment can be pre-pressurized, then heated, then repressurized to maintain a preferred pressure level within the reaction compartment. The reaction compartment can be pressurized either by vapor, gas, or steam produced by a reagent, solution, or liquid within the reaction compartment or by air, steam, inert gases, $N_2$ or any other gas typically used for pressurizing vessels, which is provided from an external source and is supplied via air/pressure ducts or conduits or vacuum lines into the reaction compartment, or by any other method described herein, such as by in situ pressurization.

Embodiments of FIGS. 23-28

Figure 23:
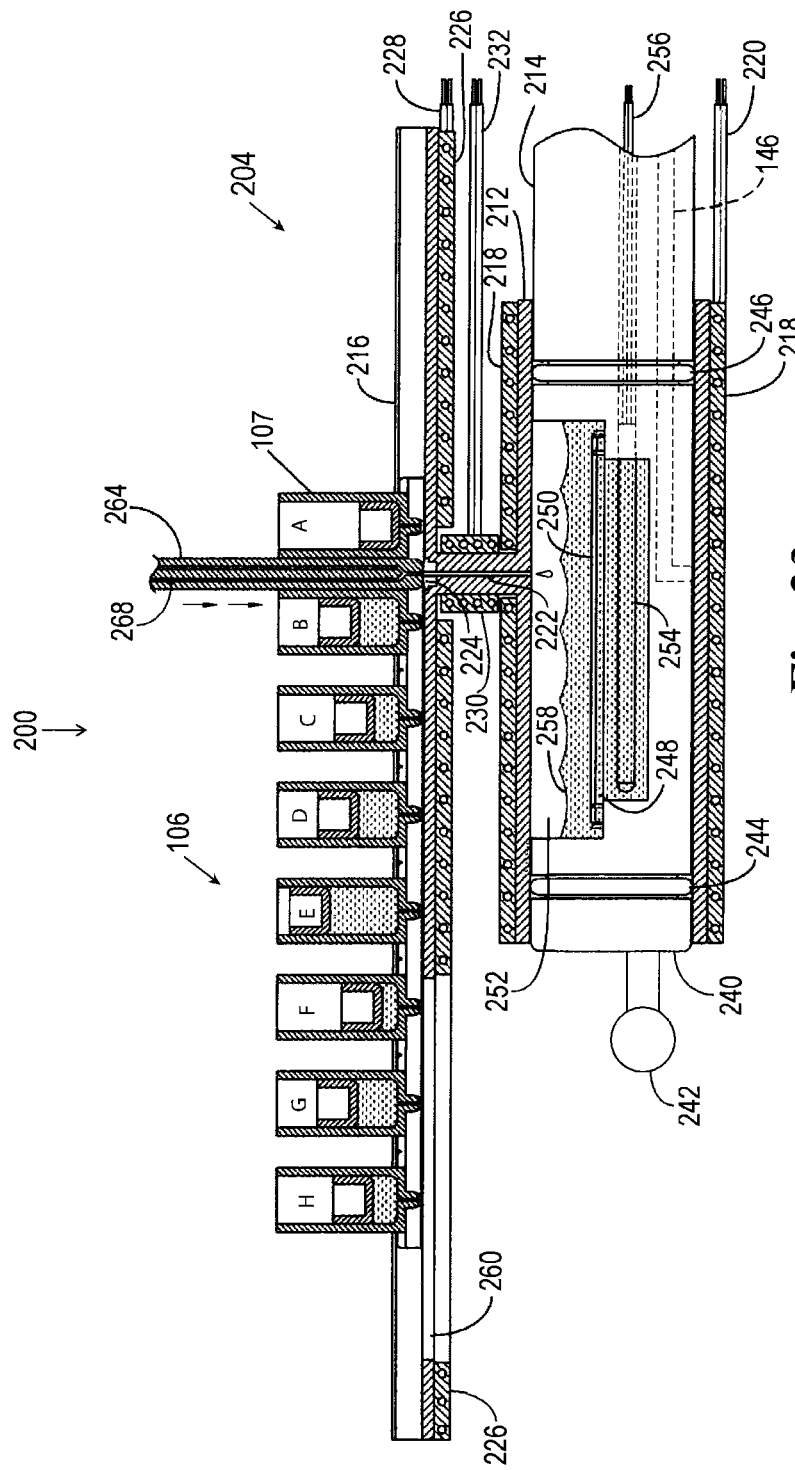
FIG. 23 is a cross-sectional side view of an alternate embodiment of the reaction components, particularly the slide support element, of the present invention.
Figure 24:
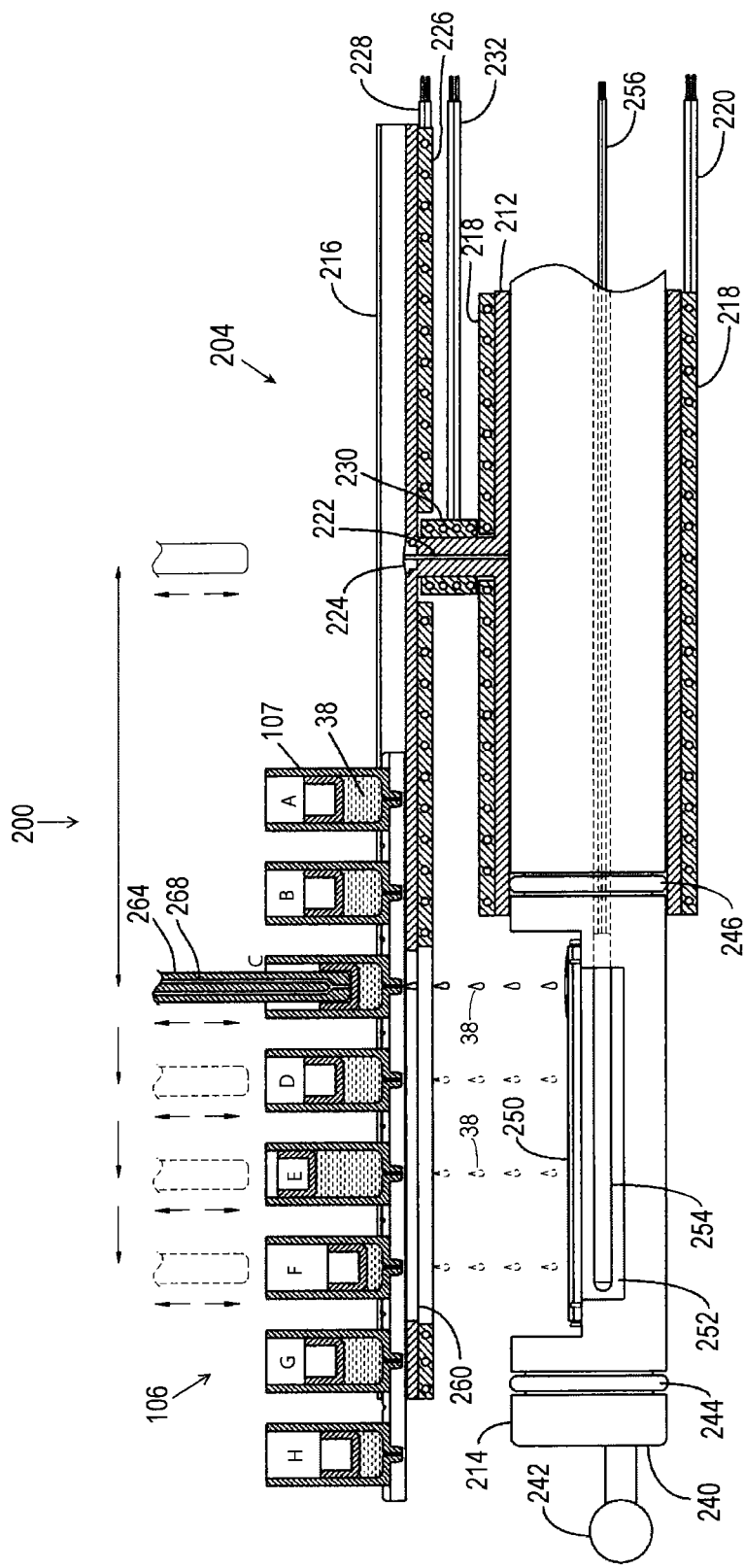
FIG. 24 is a cross-sectional side view of the reaction components of FIG. 23 in an alternate processing configuration wherein a reagent of the reagent pack is applied to the microscope slide outside of the reaction compartment.
Figure 25:
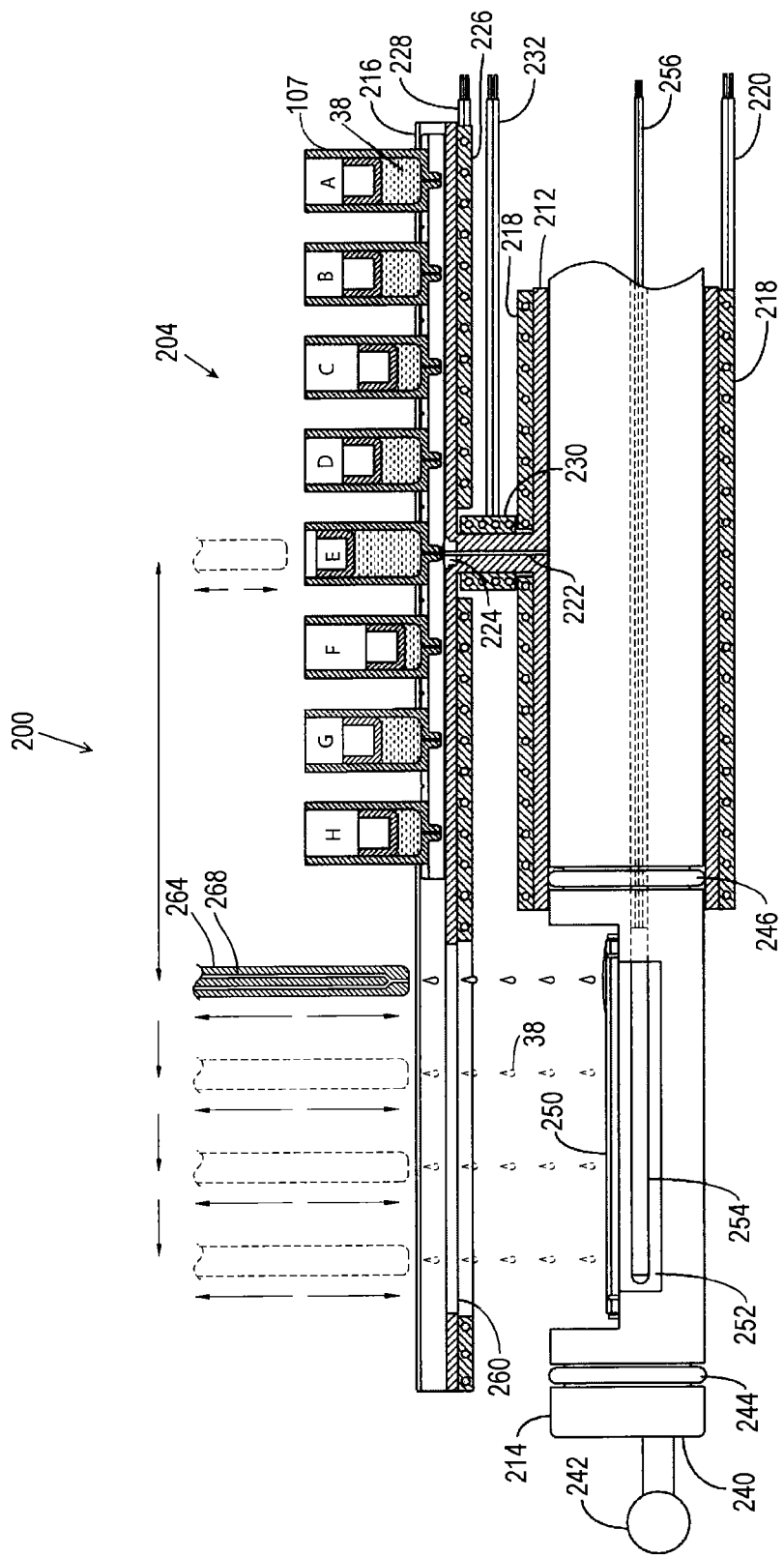
FIG. 25 is a cross-sectional side view of the reaction components of FIG. 23 in another alternate processing configuration wherein a reagent from a remote source is applied to the microscope slide outside of the reaction compartment.
Figure 26:
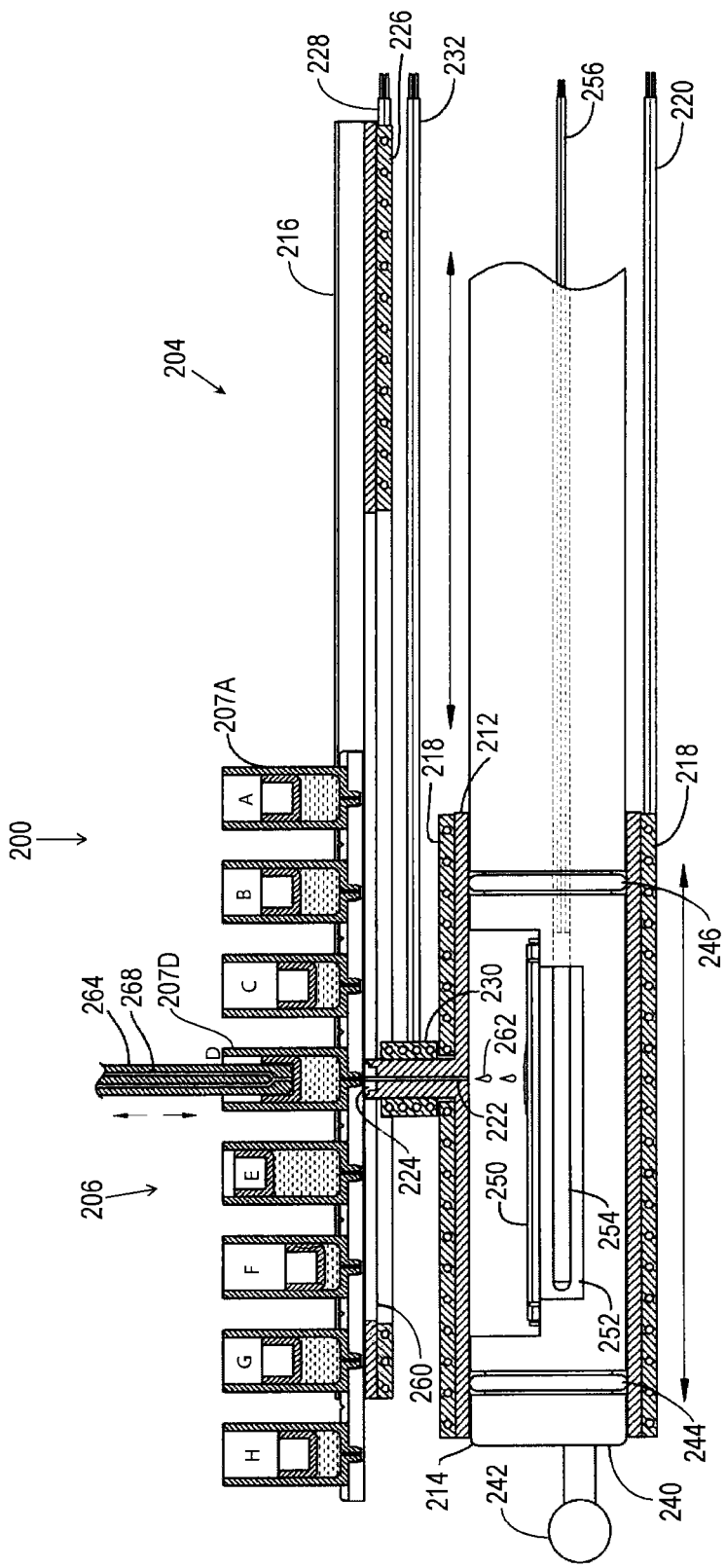
FIG. 26 is a cross-sectional side view of the reaction components of FIG. 23 in an alternate processing configuration.
Figure 27:
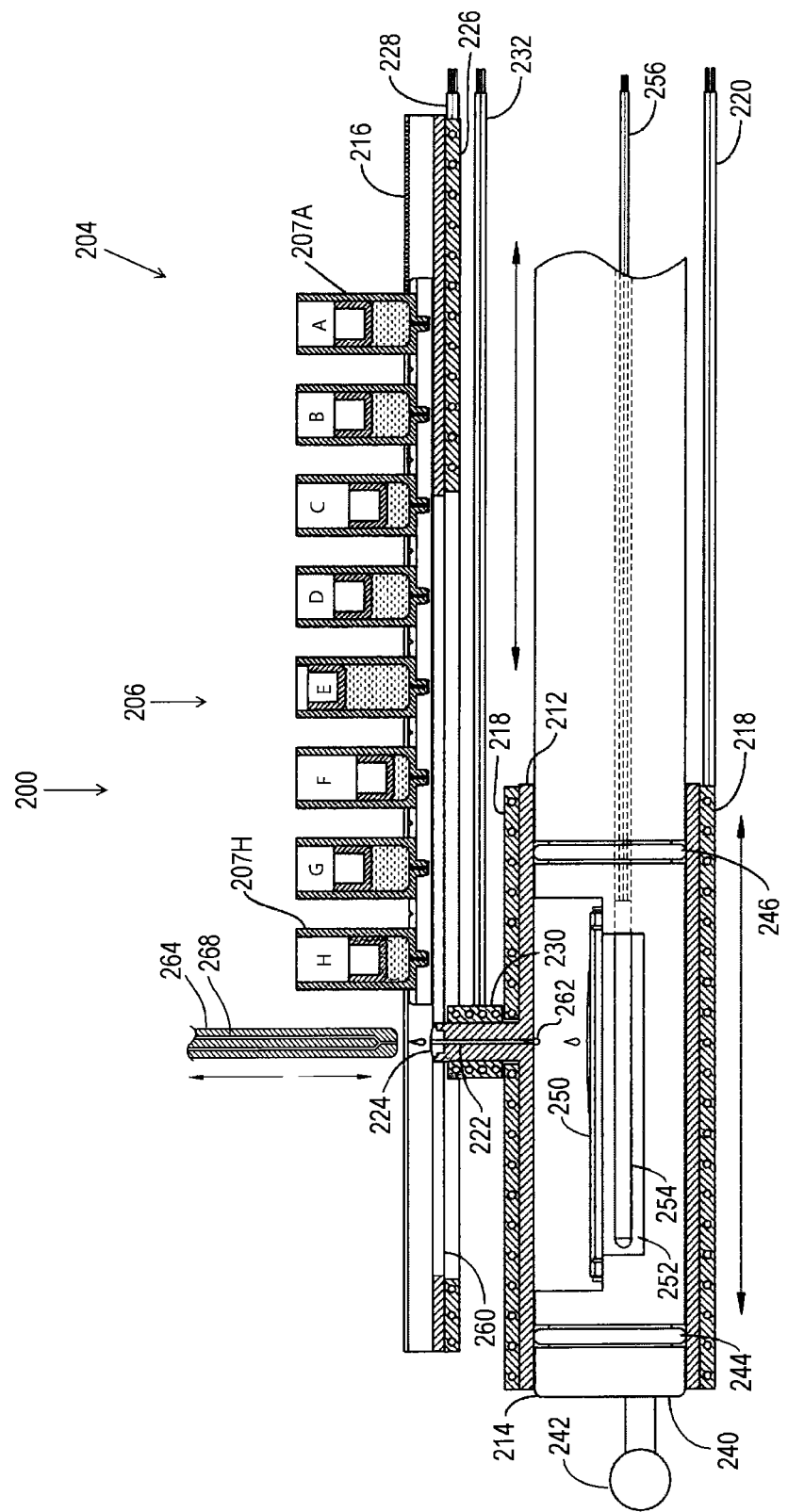
FIG. 27 is a cross-sectional side view of the reaction components of FIG. 23 in an alternate processing configuration.
Figure 28:
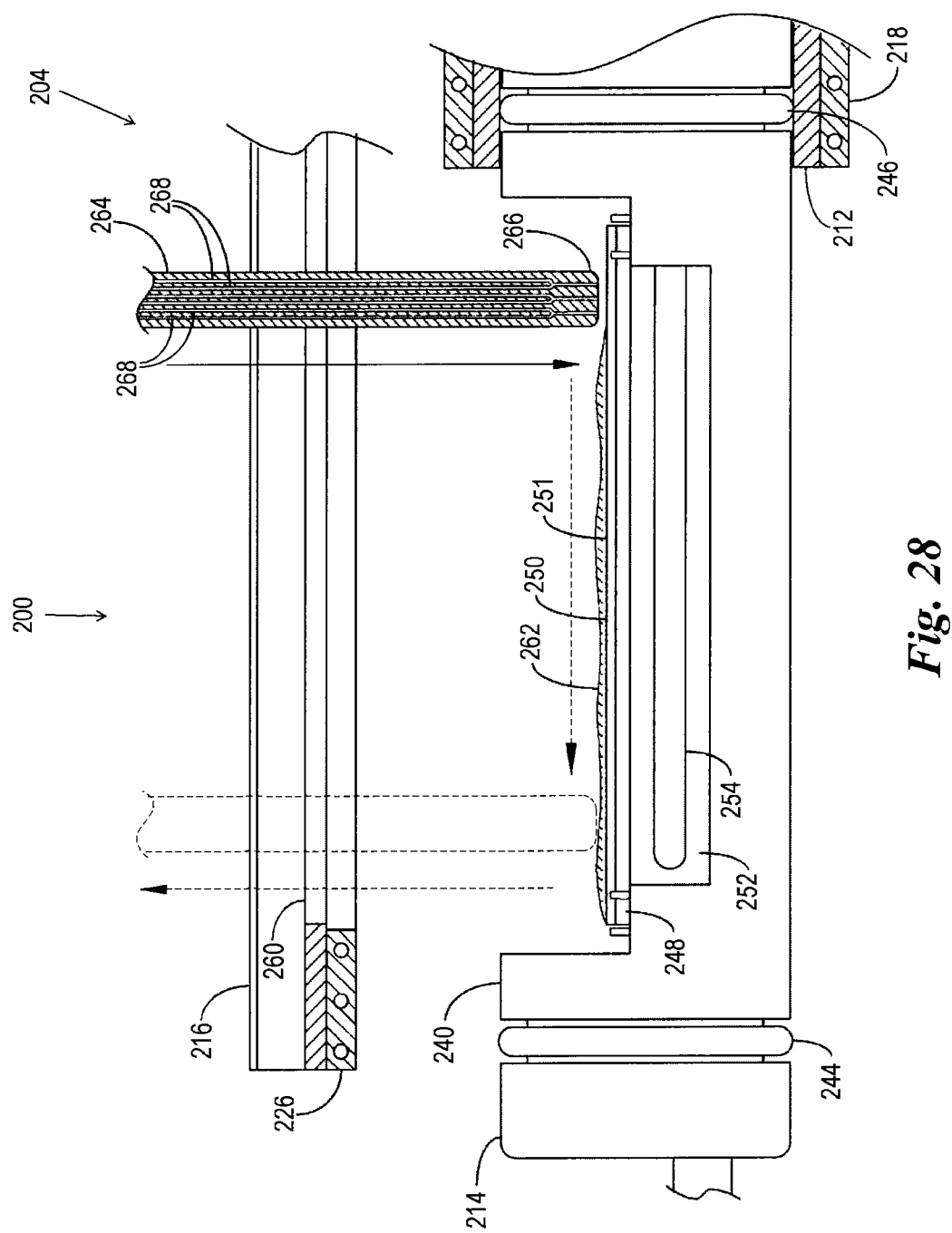
FIG. 28 is an enlarged fragmented cross-sectional side view of the reaction components of FIG. 23 in an alternate processing configuration.

As shown in FIGS. 23-28 in an alternate version of the present invention, a staining apparatus 200 contains reaction components 204 are similar to reaction components 104 in comprising a reaction compartment 212 similar to reaction compartment 112, a slide support element 214 similar to slide support element 114, and a reagent pack support device 216 similar to reagent pack support device 116. Reaction compartment 212 comprises a reaction compartment heater 218 for heating the reaction compartment 212 and optionally the slide support element 214 when disposed therein or other gases or liquids therein. The reaction compartment heater 218 has leads 220 thereto for connecting to an electric power source (not shown). The reaction compartment 212 further comprises a reagent conduit 222 and an injector port orifice 224 for delivering a reagent or other solution into the reaction compartment 212. The reaction components 204 further comprise a reagent strip heater 226 incorporated into the reagent pack support device 216 for heating a reagent pack 206 (such as any of the reagent packs disclosed herein) disposed thereon. Leads 228 connect the reagent strip heater 226 to an electric power source (not shown). The reaction compartment 212 further comprises a reagent conduit heater 230 for heating the reagent conduit 222 thereby functioning to heat a reagent as it passes through the reagent conduit 222 into the reaction compartment 212 or merely onto a microscope slide 250 if the reagent is applied when the microscope slide 250 is outside of the reaction compartment 212. Leads 232 connect the reagent conduit heater 230 to an electric power source (not shown). The slide support element 214 comprises a base 240 and, a handle 242, and a front O-ring 244 and a rear O-ring 246 for sealing the base 240 and microscope slide 250 within the reaction compartment 212. The slide support element 214 further comprises a microscope slide platform/heater 248 and in operation has the microscope slide 250 disposed thereon, the microscope slide 250 having an upper surface 251. The base 240 further comprises a base cavity 252 positioned below the slide platform/heater 248 and has a base cavity heater 254 positioned therein and connected via lead 256 to an electric power source (not shown). The base cavity heater 254 functions to heat a reagent 258 disposed within the base cavity 252 to a temperature sufficient to heat the microscope slide 250 and biological specimen and reagent 258 disposed thereon as described elsewhere herein for other embodiments of the invention. The reagent 258 in one preferred embodiment completely immerses the microscope slide 250 as shown in FIG. 23. The reagent pack support device 216 in this embodiment comprises a slot 260 (which may also be included in the reagent pack support device 116) therein for enabling a dispenser plunger (i.e., dispenser element) 264 to deliver a reagent 262 directly upon the microscope slide 250 either when it is positioned within the reaction compartment 212 (FIGS. 23, 26, 27) or outside of the reaction compartment (FIGS. 24, 25). As shown in FIGS. 24, 25, and 28 reagents may be applied to or removed from the microscope slide 250 when the microscope 250 slide is positioned outside of the reaction compartment 212 on the slide support element 214 and potentially outside of the staining apparatus 200. Reagent may be removed from the microscope slide 250 by the dispenser plunger 264 by moving the tip 266 of the dispenser plunger 264 over the microscope slide 250 and aspirating the reagent therefrom. Reagent may be delivered to or removed from the microscope slide 250 through one or more conduits 268 in the dispenser plunger 264 (FIG. 28). The conduits 268 may function to provide reagents or solutions, to remove reagents (via aspiration for example), or may provide air, gases, or liquids under pressure.

In other embodiments, reaction components 204 of the present invention may have any one or any combination of slide heating elements 136 or 248, reaction compartment heater 218, reagent strip heater 226, reagent conduit heater 230, and base cavity heater 254, and when present any of the heating systems described herein may function individually and independently of one another. The slide support element 214 may further optionally comprise one or more drainage and/or supply conduits which lead to the base cavity 252 for supplying the base cavity 252 with a liquid or other solution and for draining used liquid from the base cavity 252 after its use (e.g., by aspiration). Other supply ports, conduits, and ducts may supply the reaction compartments of the present invention such as are described in U.S. Pat. Nos. 6,534,008 and 6,855,292.

In a preferred embodiment, the reaction compartment and/or slide support element of the present invention may be exposed to sterilization conditions which may include high heat (e.g., above 100° C., or more preferably above 130° C., and may use steam and/or chemicals to remove, or denature pathogens or residual chemicals or materials such as nucleic acids, antibodies, toxins or other proteins which remain in the reaction compartment and slide support element after the reaction components are used. In a preferred embodiment, the reaction compartment and/or slide support element after heating is quickly cooled to near room temperature or to below 50° C. within 3 sec, 5 sec, 10 sec or 20 sec for example to further denature or inactivate residual proteins or substances.

Further, although the various reaction components are shown herein as components in discrete embodiments, it is contemplated that various components described herein can be assembled in any combination which functions in accordance with the present invention.

Embodiments of FIGS. 29A-29F

Shown in FIGS. 29A-29F is a staining apparatus 300 which is at least one of one or more of such chambers of a microscope slide staining apparatus of the present invention. The staining apparatus 300 has an inner space 302, a front wall 304, a slide support element 310 having a heating element 312, and an optional handle 314, a reaction compartment 316, such as other reaction compartments described herein, a reagent pack support device 318, a reagent plunger 319, and a reagent dispenser 320 each of which is movable upwardly and downwardly in direction 321 and which may be movable laterally as well. When the slide support element 310 is inserted into the inner space 302, an end portion of the slide support element 310 is preferably aligned flush with an outer surface of the front wall 304 as shown in FIGS. 29B-29E.

Figure 29E:
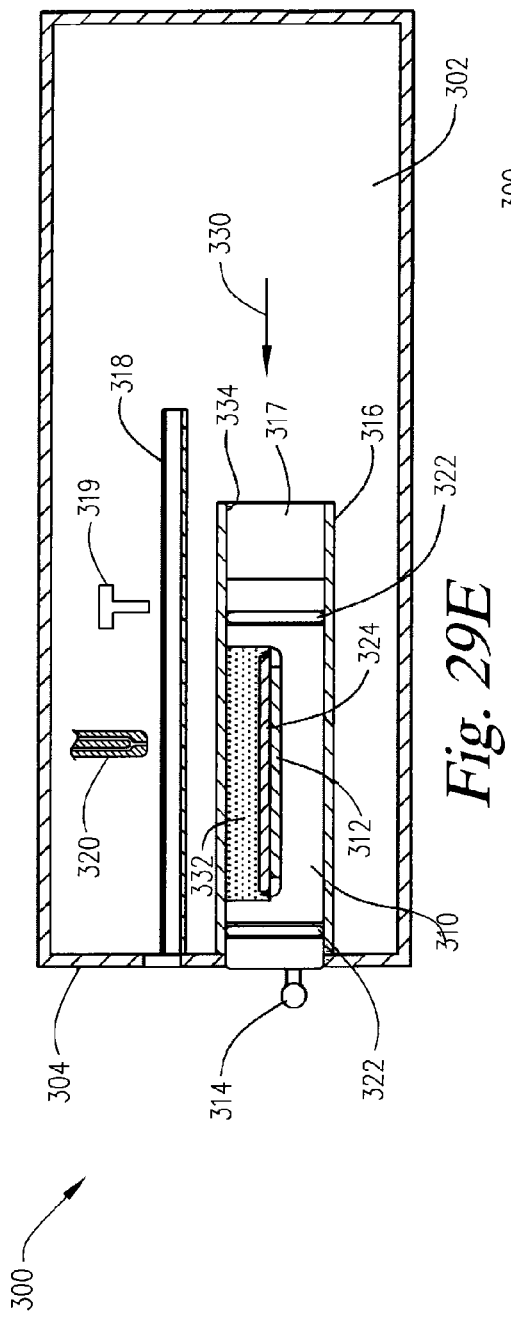
Figure 29F:
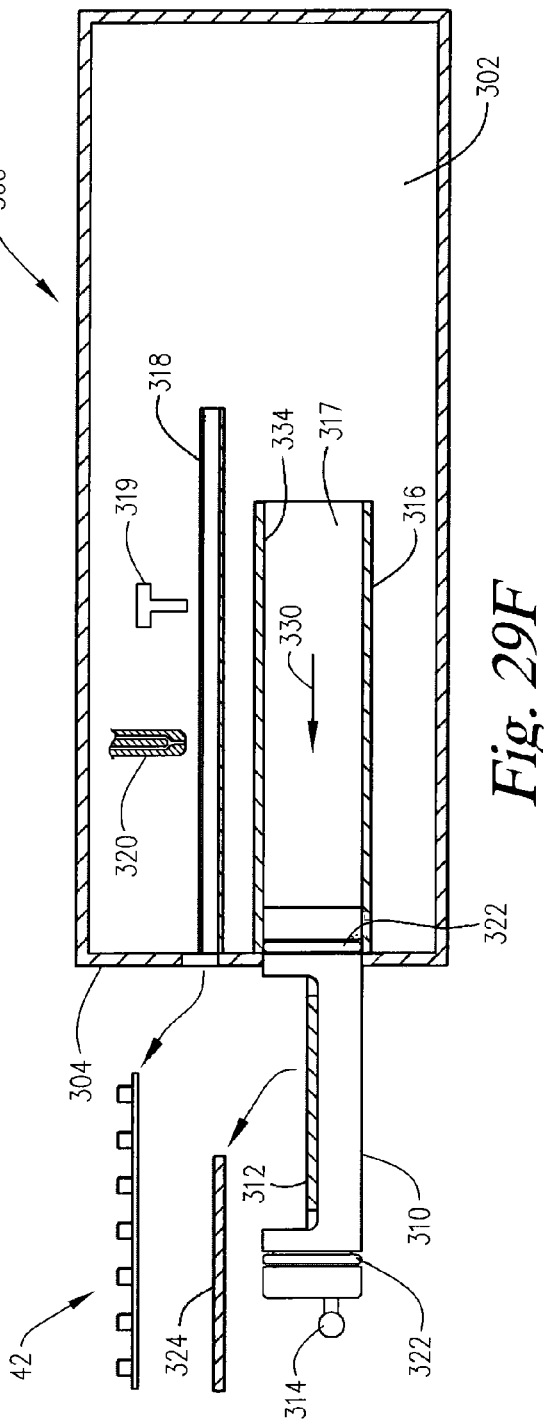
Figure 32:
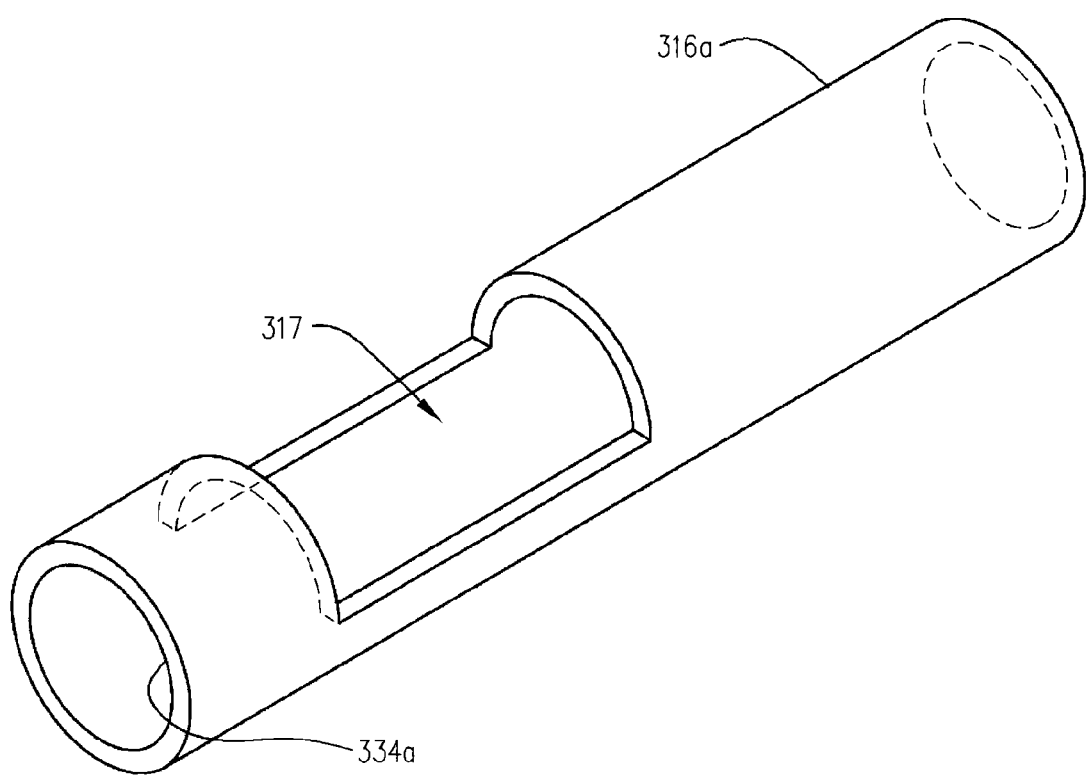
FIG. 32 is a perspective view of a reaction compartment having a window, such as is used in the embodiment of FIGS. 31A-31F.

The slide support element 310 is similar to other slide support elements described herein and has sealing means 322 such as described elsewhere herein for enabling a microscope slide 324 to be sealingly enclosed on the slide support element 310 within the reaction compartment 316. A reagent pack 42 (such as any reagent pack contemplated herein) can be inserted through an opening in the front wall 304 into the inner space 302 of the staining apparatus 300 where it is secured on the reagent pack support device 318 for dispensing a reagent 328 onto the microscope slide 324 via the reagent plunger 319 or by reagent dispenser 320 in a manner similar to that described for other such dispensers and plungers discussed elsewhere herein (in an alternate embodiment, the reagent pack support device 318 (or any support devices contemplated herein) may be ejected through an opening in the front wall 304 such that the reagent pack 42 can be loaded outside thereon of the staining apparatus 300. Shown in FIG. 29A the microscope slide 324 is initially in a placement position outside of the reaction compartment 316 and inner space 302 of the staining apparatus 300. A microscope slide 324 is positioned on the heating element 312 of the slide support element 310 which is retracted in direction 326 into the reaction compartment 316 (FIG. 29B). A reagent 328 is delivered to the microscope slide 324 via the reagent plunger 319 (from the reagent pack 42) on the reagent pack support device 318 or from a remote reagent source via reagent dispenser 320 after the reaction compartment 316 has been retracted from the slide support element 310 in direction 326 (FIG. 29C). After the reagent 328 has been applied to the microscope slide 324, the reaction compartment 316 is moved in direction 330 back over the slide support element 310 wherein the sealing means 322 causes the slide support element 310 to be sealed against the inner surface 334 of the reaction compartment 316 so the microscope slide 324 is sealed therein (FIG. 29D) within a pressurizable treatment space 332 within the reaction compartment 316. The pressurizable treatment space 332 is then pressurized via pressurizing means as described elsewhere herein (FIG. 29E). The microscope slide 324 is heated by the heating element 312 to a predetermined temperature which causes the reagent 328 on the microscope slide 324 to be heated to an elevated temperature above that which could be obtained absent the elevated pressure of the pressurizable treatment space 332. The heated reagent 328 causes the desired biochemical/physical reaction within the biological sample on the microscope slide 324 within the pressurizable treatment space 332. After the reaction is completed, the pressure level within the pressurizable treatment space 332 of the reaction compartment 316 is returned to a normal (pre-pressurization) level and the reagent 328 is removed therefrom by means such as those discussed elsewhere herein. The slide support element 310 is then ejected from the reaction compartment 316 and/or inner space 302 of the staining apparatus 300 via direction 330 wherein the microscope slide 324 can be removed therefrom (FIG. 29F). This can occur immediately after the heating step, or after one or more additional steps or procedures has been performed on the microscope slide 324. For example the steps of FIGS. 29B-29D (and optionally FIG. 29E) can occur several times before the microscope slide 324 is removed in the step of FIG. 29F.

Embodiments of FIGS. 30A-30F

Shown in FIGS. 30A-30F is a staining apparatus 340 which is at least one of one or more of such chambers of a microscope slide staining apparatus of the present invention. The staining apparatus 340 has an inner space 342, a front wall 344, a slide support element door 346 (shown open), a reagent pack door 348, a slide support element 350 having a heating element 352, an optional handle 354, a reaction compartment 356, such as other reaction compartments described herein except having a closed end 364, a reagent pack support device 366, and a reagent dispenser plunger 368.

Reaction compartment 356 further comprises an inner space 362, a pressure equalization conduit 358 between a forward portion of the inner space 362 and a rear portion of the inner space 362 and a rear portion of the inner space 362. A conduit valve 360 is present in the pressure equalization conduit 358 for opening and closing the conduit 358 when desired or for preventing backflow.

The slide support element 350 is similar to other slide support elements described herein such as shown in FIGS. 29A-29F, and has sealing means 370 such as described elsewhere herein for enabling a microscope slide 324 to be sealingly enclosed within the reaction compartment 356. A reagent pack 42 can be inserted through the opened reagent pack door 348 into the inner space 342 of the staining apparatus 340 where it is secured on the reagent pack support device 366 for dispensing a reagent 328 onto the microscope slide 324 via the reagent plunger 367 or via a reagent dispenser 368 in a manner similar to that described for other such dispensers or plungers discussed elsewhere herein. In this embodiment, the microscope slide 324 is initially in a placement position outside of the reaction compartment 356 and the inner space 342 of staining apparatus 340. A microscope slide 324 is positioned on the heating element 352 of the slide support element 350 which is retracted in direction 372 into the reaction compartment 356 (FIG. 30B). A reagent 328 is delivered to the microscope slide 324 from the reagent plunger 367 (from the reagent pack 42) on the reagent pack support device 366 or from a remote reagent source via reagent dispenser 368 after the reaction compartment 356 has been retracted from the slide support element 350 in direction 372 (FIG. 30C). After the reagent 328 has been applied to the microscope slide 324, the reaction compartment 356 is moved in direction 376 back over the slide support element 350 wherein the sealing means 370 causes the slide support element 350 to be sealed against the inner surface 357 of the reaction compartment 356 so the microscope slide 324 is sealed therein within a pressurizable treatment space 378 within the reaction compartment 356. The pressurizable treatment space 378 (also referred to herein a pressurization treatment space 378) is then pressurized (FIG. 30D) via "in situ pressurization" as explained below.

The microscope slide 324 is heated by the heating element 352 to a predetermined temperature which causes the reagent 328 on the microscope slide 324 to be heated to an elevated temperature above that which could be obtained absent the elevated pressure in the pressurizable treatment space 378. The heated reagent 328 causes the desired biochemical/physical reaction within the biological sample on the microscope slide 324 within the pressurizable treatment space 378. After the reaction is completed, the pressure level within the pressurizable treatment space 378 and head space 380 of the reaction compartment 356 is returned to normal and the reagent 328 is removed therefrom by means such as those discussed elsewhere herein. The slide support element 350 is then ejected from the reaction compartment 356 and/or inner space 342 of the staining apparatus 340 via direction 384 wherein the microscope slide 324 can be removed therefrom (FIG. 30F). This can occur immediately after the heating step, or after one or more additional steps or procedures has been performed on the microscope slide 324. For example the steps of FIGS. 30B-30E can occur several times before the microscope slide 324 is removed in the step of FIG. 30F.

In a preferred embodiment of the reaction compartment 356 (and of other reaction compartments contemplated herein), the sealing means 370 comprises a ground or polished glass seal in a surface portion of the reaction compartment 356 which can hold pressure from a separate bulk source of pressure to pressurize the pressurization space 378 of the reaction compartment 356 or, in an alternative embodiment this polished seal (or other seals described herein) can also produce and hold pressure inside the pressurization space 378 of the reaction compartment 356 without the need for a separate bulk pressure source being sent to each reaction compartment 356.

This method of pressure generation, operationally represented in FIG. 30E, is referred to herein as "in-situ pressurization". The very effective sealing means 370 of the present invention can form a pressurization treatment space which is sufficiently sealed to produce and/or increase and/or decrease the pressure of atmospheric pressure conditions inside the pressurization treatment space 378 of the reaction compartment 356. After the slide support element 350 and slide thereon is sealed within the reaction compartment 356 the slide support element 350 is moved further into the inner space 362 of the reaction compartment 356 to produce pressure therein by forcing the trapped residual atmospheric air in the pressurization space 378 surrounding the microscope slide 324 in the reaction compartment 356 and inside a head space 380 of the reaction compartment 356. For example, in one embodiment the reaction compartment 356 (e.g., having a length of 8 inches can have the slide support element 350 inside the first 5 inches of its length. The head space 380 comprises the remaining 3 inches of space within the reaction compartment 356. The reagent 328 has been added to the microscope slide 324 present on the slide support element 350. The slide support element 350 is then moved farther into the head space 380 of the reaction compartment 356, for example 0.01 to nearly 3 inches. This movement, further into the reaction compartment 356 causes the gas (e.g., air) in the head space 380 between the closed end 364 of the reaction compartment 356 and a distal end 351 of the slide support element 350 to compress. This compression of the air in the head space 380 produces pressure above the original pressure in the reaction compartment 356. This pressure is diverted to the pressurization treatment space 378 by conduit 358 through valve 360. The head space 380 is only in contact with the pressurization treatment space 378 about the microscope slide 324, and vice versa, by the conduit 358 or other means to connect the head space 380 with the pressurization treatment space 378.

This connection with the head space 380 to the pressurization treatment space 378 may include as noted a one-way or two-way conduit valve 360 or other means of transferring the pressure in the compressed head space 380 to the pressurization treatment space 378 without allowing the contents of the pressurization treatment space 378 to be communicated or moved toward or into the head space 380 for possible contamination of the head space 380 or vice versa.

The pressurization conduit 350 is shown in FIGS. 30A-30F as a conduit between proximal and distal portions of the reaction compartment 356, however the conduit may instead be wholly within a distal portion of the slide support element 350 (e.g., see FIGS. 33A-33H).

Although the pressured gas or air produced from the compressed head space 380 can move into the pressurization treatment space 378 there is a need to stop any contamination of the gas or air in the compressed head space 380 with the contents of the pressurization treatment space 378 and vice versa. Valves or other systems known in the art can be used to inhibit or stop this potential backflow and/or cross-contamination. These conduit valves 360 can be, but are not limited to, in line water or gas dedicators, one-way valves, two-way valves, a one way pressure opening valves, metered ports, or any other device able to be used to prevent the contents from one compartment or area being contaminated with the contents of another compartment or area.

The amount of pressure in the pressurization treatment space 378 is proportional to the degree of movement of the slide support element 350 into the head space 380 of the reaction compartment 356. The pressure produced is directly related to the length and outer diameter of the slice support element 350 and the length and inner diameter of the reaction compartment 356 along with the total travel length of the slide support element 350 or the reaction compartment 356 with the movement to compress the head space 380 with a normal atmospheric pressure trap between the front of the reaction compartment 356 and the closed end 364 of the reaction compartment 356 to produce the increased pressure by compressing the air or gas trapped in the head space 380. The pressure in the head space 380 for example could be 20 psig caused by compressing the residual air trapped in the head space 380 and the now pressurized air could be delivered via the conduit 358 to the pressurized treatment space 378 containing the microscope slide thereby equilibrating the pressure of the pressurized head space with the pressure in the pressurized treatment space 378. Evaporation of reagents associated with the biological specimen, under heat could also contribute to the pressure in the pressurized treatment space 378. As noted above, a conduit valve 360 can be present for preventing contents of the pressurization treatment space 378 from moving into the head space 380 through the conduit 358. The pressure in the head space 380 can be increased or decreased before, during, or after the heating element 352 heats the reagent 328 in contact with the microscope slide 324. Since the reaction compartment 356 may have a heating device in its walls, in one embodiment of the invention, a liquid could also be added to the head space 380 to produce steam or gas to be sent through the conduit 358 to pressurize the pressurization treatment space 378 of the slide support element 350.

In summary, the head space 380 can be used to cause pressurization of the pressurization treatment space 378 (above or below atmospheric pressure) before, during, or after the heating elements 352 are turned on without having an external source of pressure used to pressurize the pressurization treatment space 378. Further, the presently described in situ pressurization of the pressurization treatment space 378 can occur without use of heat from heating elements. Alternatively, as noted, liquid could be added to the head space 380 to induce pressurization by steam or vapors or add further pressure to the pressurization treatment space 378 in the reaction compartment 356 whether the head space 380 is compressed or not. This apparatus could also be able to draw a vacuum into the pressurization treatment space 378, for example by reversing the movement of the slide support element 350 and pulling the reaction compartment 356, the slide support element 350, or both, in opposite directions to produce a vacuum in the conduit 358 and thereby placing the vacuum in both the head space 380 and pressurization treatment space 378. This method can also be used to regulate the pressure inside the pressurization treatment space 378 regardless of the source of the pressure by moving the reaction compartment 358 and slide support element 350 together or separately to cause a pressure or vacuum environment to regulate the pressure or vacuum conditions within the reaction compartment 356. In one example, if the pressure is desired to be maintained at 30 psig in the pressurization treatment space 378, the regulation can come from the pressurized or depressurized head space 380. This regulation is available no matter how the pressure was or is originally being maintained. For example, if the microprocessor senses the pressure in the pressurization treatment space 378 exceeds the desired temperature or is too low, the position of the slide support element 350 or reaction compartment 356 could be adjusted slightly to change the pressure level. Or the microprocessor could use this head space pressure regulation process to quickly reduce or add pressure to the pressurization treatment space 378 for a condition that might become dangerous to the limits of the strength and integrity of the reaction compartment 356 as a failsafe option. The change in pressure in the head space 380 can be a fine adjustment or coarse adjustment to the pressure in the pressurization treatment space 378. The adjustment increments can be of any measurable amount. The adjustment can be as little as 0.001 psig above or below atmospheric pressure. Preferably the adjustment is in 0.5 psig increments either above or below atmospheric pressure.

In this embodiment of the present invention, as noted "in-situ" pressurization and vacuum (above atmospheric or below atmospheric pressure) is caused by compressing the head space 380 in the portion of the reaction compartment 356 between the closed end 364 thereof and the distal end 351 of the slide support element 350. An individual reaction compartment 356 can move in relation to the slide support element 350 or the slide support element 350 can move in relation to the corresponding individual reaction compartment 356. The individual reaction compartment 356 and the slide support element 350 can move independently of each other and/or simultaneously with each other to compress the head space 380 present between the individual reaction compartment 356 and the distal end 351 of the slide support element 350. In the preferred embodiment of the "in-situ" production of pressure described herein, in which a single individual reaction compartment 356 is sealed about a single slide support element 350, both are independently movable in relation to each other under pressure and wherein pressure is produced by the relative movement of each other and the sealed head space 380 in relation to the sealed individual reaction compartment 356 and the single slide support element 350. As noted previously, the reaction compartment 356 can be modified to hold more than one microscope slide per slide support element (e.g., 2 or more) if desired and still be able to produce "in-situ pressurization". A reaction compartment 356 could be sized to hold multiple slide support elements 350 moving on a single platform that can be joined with a reaction compartment 356 which is complementary with the larger slide support platform. In situ pressurization via compression of the head space 380 of the reaction compartment 356, can be performed without addition of additional pressurization from a remote pressurization means thus reducing the complications inherent in using such a remote source for example the requirement of tubes, valves, and conduits able to tolerate above-atmospheric or below-atmospheric pressures.

Embodiments of FIGS. 31A-31F and 32

Shown in FIGS. 31A-31F and 32 is a staining apparatus 300a which is at least one of one or more of such chambers of a microscope slide staining apparatus of the present invention. The staining apparatus 300a has an inner space 302a, a front wall 304a, a slide support element door 306a (shown open), a reagent pack door 308a, a slide support element 310a having a heating element 312a, an optional handle 314a, a reaction compartment 316a, a reagent pack support device 318a, a reagent plunger device 319a and a reagent dispenser 320a.

The staining apparatus 300a is substantially the same as staining apparatus 300 of FIGS. 29A-29F except that the reaction compartment 316a differs from reaction compartment 316 of FIG. 29A in that it has an open portion or "window" 317 through which the reagent 328 can be applied to the microscope slide 324 from or by the reagent plunger 319a or via the reagent dispenser 320a. In this embodiment with "windows", the window 317 is advantageous in enabling the reagent to be dispensed upon the microscope slide 324 without having to be passed through a narrow reagent conduit. Further, a dispenser element associated with the X-Y-Z positioning device (e.g. such as reagent dispenser 320a) does not have to be adapted for use with a reagent pack to be able to be used with the reaction compartment window 317.

The reaction compartment 316a can be rotated about the slide support element 310a to close the window 317 to form a pressurizable treatment space 332a around the microscope slide 324 in the reaction compartment 316a. In this embodiment, preferably, the sealing means 322a is a ground and polished glass surface that can be easily rotated to open and close the window 317. Reaction compartment 316a with window 317 is shown in a perspective view in FIG. 32. The rotational movement in this embodiment of the reaction compartment 316a can be a few degrees or can be 180° or more in relation to the microscope slide 324. Thus, the window 317 of the reaction compartment 316a can be positioned directly above the microscope slide 324 (in a 0° position or "open" position) or can be rotatingly moved through a range of positions to be directly under the microscope slide 324 (180° position or "closed" position), rotating in either direction from the 0° home (open) position to the closed position wherein the window is covered by a lower surface of the slide support element 310a. The sealing means 322a can be of any type known in the art of sealing pressurized vessels. The preferred sealing means 322a is a ground and polished glass seal. This type of seal is known in the art of ground and polished seals for glass hypodermic syringes for example which are manufactured and sold under the trade name Micro-Mate® by Popper and Sons, Inc. New Hyde Park, N.Y., and thus such ground and polished glass seals are known in the art.

The slide support element 310a is similar to other slide support elements described herein and has sealing means 322a such as described elsewhere herein for enabling the microscope slide 324 to be sealingly enclosed within the reaction compartment 316a. A reagent pack 42 can be inserted through the opened reagent pack door 308a into the inner space 302a of the staining apparatus 300a where it is secured on the reagent pack support device 318a (or otherwise positioned thereon) for dispensing a reagent 328a onto the microscope slide 324 via the reagent plunger 319a or via reagent dispenser 320a in a manner similar to that described for other such dispensers or plungers discussed elsewhere herein except that the reagent 328 is preferably disposed through the window 317 of the reaction compartment 316a. In this embodiment, the microscope slide 324 is initially in a placement position outside of the reaction compartment 316a and inner space 302a of the staining apparatus 300a. The microscope slide 324 is positioned on the heating element 312a of the slide support element 310a which is retracted in direction 326a into the reaction compartment 316a (FIG. 31B). A reagent 328 is delivered to the microscope slide 324 from the reagent plunger 319a (from the reagent pack 42) on the reagent pack support device 318a or from a remote reagent source via reagent dispenser 320a (FIG. 31C). Then the reaction compartment 316a is rotated 180° (or other equally effective amount) about the slide support element 310a in direction 329 (FIG. 31D), thereby closing the window 317 wherein the sealing means 322a causes the slide support element 310a to be sealed against an inner surface 334a of the reaction compartment 316a so the microscope slide 324 is sealed therein within the pressurization treatment space 332a. The pressurization treatment space 332a is then pressurized (FIG. 31D) via pressurizing means as described elsewhere herein. The microscope slide 324 is then heated by the heating element 312a to a predetermined temperature which causes the reagent 328 on the microscope slide 324 to be heated to an elevated temperature above that which could be obtained absent the elevated pressure in the pressurization treatment space 332a. The heated reagent 328 causes the desired biochemical/physical reaction within the biological sample on the microscope slide 324 within the pressurization treatment space 332a. After the reaction is completed, the pressure level within the pressurization treatment space 332a of the reaction compartment 316a is returned to normal, the reaction compartment 316a is rotated to the home (open) position (FIG. 31E), and the reagent 328 is removed therefrom by means such as those discussed elsewhere herein. The slide support element 310a is then ejected from the reaction compartment 316 and/or inner space 302a of the staining apparatus 300a via movement in direction 330 wherein the microscope slide 324 can be removed therefrom (FIG. 31F). This can occur immediately after the heating step, or after one or more additional steps or procedures has been performed on the microscope slide 324. For example the steps of FIGS. 31C-31E can occur several times before the microscope slide 324 is removed in the step of FIG. 31F.

Embodiments of FIGS. 33A-33H

Shown in FIGS. 33A-33H is a staining apparatus 340a which is at least one of one or more of such chambers of a microscope slide staining apparatus. The staining apparatus 340a has an inner space 342a, a front wall 344a, a slide support element door 346a (shown open), a reagent pack door 348a, a slide support element 350a having a heating element 352a, a distal end 351a, an optional handle 354a a reaction compartment 356a, which combines the elements of other reaction compartments described herein such as reaction compartments 316a and 356, a reagent pack support device 366a, a reagent plunger 367a, and a reagent dispenser 368a.

In particular, the reaction compartment 356a has a closed end 364a, and inner surface 357a, an inner space 362a, and a window 365 through which a reagent 328 can be applied in the manner shown in FIGS. 31A-31F. The slide support element 350a comprises a pressure equalization conduit 358a which is similar to the pressure equalization conduit 358 of FIGS. 30A-F in that the conduit 358 allows pressure equalization between a forward portion of the inner space 362a (which constitutes a pressurization treatment space 378a where the microscope slide 324 is positioned) and a rear portion which constitutes a head space 380a of the reaction compartment 356a, but which is different therefrom in that conduit 358a is positioned in a distal portion 351a of slide support element 310a rather than in reaction compartment 356a.

The slide support element 350a is similar to other slide support elements described herein and has sealing means 370a such as described elsewhere herein for enabling a microscope slide 324 to be sealingly enclosed within the reaction compartment 356a. A reagent pack (not shown) can be inserted through the opened reagent pack door 346a into the inner space 342a of the staining apparatus 340a where it is secured on the reagent pack support device 366a for dispensing a reagent 328 onto the microscope slide 324 via the reagent plunger 367a or via reagent dispenser 368a in a manner similar to that described for other such dispensers and plungers discussed elsewhere herein. In this embodiment, the slide support element 350a is initially in a placement position outside of the reaction compartment 356a and staining apparatus inner space 342a (FIG. 33A). A microscope slide 324 is positioned on the heating element 352a of the slide support element 350a which is retracted in direction 372 into the reaction compartment 356a (FIG. 33B). A reagent 328 is delivered through window 365 to the microscope slide 324 from the reagent plunger 367a (from the reagent pack (not shown)) on the reagent pack support device 366a or from a remote reagent source via reagent dispenser 368a after the reaction compartment 356a has been retracted from the slide support element 350a in direction 372 (FIG. 33C). After the reagent 328 has been applied to the microscope slide 324, the reaction compartment 356a is rotated 180° (or other appropriate amount) in direction 373 wherein the sealing means 370a causes the slide support element 350a to be sealed against the inner surface 357a of the reaction compartment 356a in the same manner as in FIG. 31D wherein the microscope slide 324 is sealed therein (FIG. 33D) within a pressurization treatment space 378a. The pressurization treatment space 378a is then pressurized as shown in FIGS. 33E-33F in the same "in situ pressurization" method shown and described in regard to FIGS. 30D-30E. The microscope slide 324 in the pressurization treatment space 378a is heated by the heating element 352a to a predetermined temperature which causes the reagent 328 on the microscope slide 324 to be heated to an elevated temperature above that which could be obtained absent the elevated pressure in the pressurization treatment space 378a. The heated reagent 328 causes the desired biochemical/physical reaction within the biological sample on the microscope slide 324 within the pressurization treatment space 378a (FIG. 33F). After the reaction is completed, the pressure level within the pressurization treatment space 378a of the reaction compartment 356a is returned to normal (FIG. 33G) and the reagent 328 is removed therefrom by means such as those discussed elsewhere herein. Additional reagent can then be applied to the slide through the window 365 if desired. The slide support element 350a is then ejected from the reaction compartment 356a and/or inner space 342a of the staining apparatus 340a via direction 384 wherein the microscope slide 324 can be removed therefrom (FIG. 33H). This can occur immediately after the heating step, or after one or more additional steps or procedures has been performed on the microscope slide 324. For example the steps of FIGS. 33C-33G can occur several times before the microscope slide 324 is removed in the step of FIG. 33H.

Shown in FIG. 34 an alternate embodiment of the invention is represented as the staining apparatus 400. The staining apparatus 400 has a front wall 402, a back wall 404, a first side wall 406, a second side wall 408, and an inner space 410. Inside the staining apparatus 400 are a plurality of sets of reaction components 412 (six are shown but more or less may be included) similar to the reaction components of any of 1-6 and 29A-33H. In particular, each set of reaction components 412 comprises a movable reaction compartment 414 and a movable slide support element 416 each which is independently movable of each other reaction compartment and slide support element respectively. The slide support element 416 is moved forwardly, backwardly, and rotatingly by a motor assembly 418 comprising a motor 420 and a shaft 422. A motor assembly for moving the reaction compartment 412 forwardly, backwardly and preferably rotatingly is not shown. The staining apparatus 400 is operable in any of the configurations represented in FIGS. 1-6 and 29A-33H and as contemplated elsewhere herein and further as described herein. For example, slide support elements 416 can be moved into and out of the inner space 410 of the staining apparatus 400, and into and out of reaction compartments 412; similarly, reaction compartments 412 can be moved over and sealed about slide support elements 416 or retracted to expose the slide support elements 416. Staining apparatus 400 is further shown as having an X-Y-Z positioning device 430 having as a movable head 432 discussed elsewhere herein which is positioned in the inner space 410 such that the movable head 432 can be moved laterally and vertically over the slide support elements 416 on a rail 434. The movable head 432 in one embodiment of the X-Y-Z positioning device 430 comprises a dispensing element for dispensing a reagent or other dispensable material, such as a cover slip or a bonding material for attaching a cover slip. The movable head 432 may comprise a bar code reader or other mechanism for obtaining information from the microscope slide or from the reagent pack. The movable head 432 may comprise an inkjet printer or laser etching device or other light emitting device for imparting or printing a pattern, symbol, or label on the microscope slide or other device described herein. The movable head 432 may comprise an aspirator for removing a reagent or solution from the microscope slide or slide support element. The staining apparatus 400 may comprise multiple X-Y-Z positioning devices 430 and/or multiple movable heads 432, each separate movable head 432 able to perform one or more of the functions contemplated herein. For example, in one non-limiting example, the staining apparatus 400 may comprise one X-Y-Z positioning device 430 comprising a movable head 432 which is an inkjet printer, another X-Y-Z positioning device 430 comprising a movable head 432 which is an optical code reader and/or scanner, and another X-Y-Z positioning device 430 comprising a movable head 432 which is reagent dispenser and/or reagent aspirator. In the staining apparatus 400, the reagents are applied to the microscope slide and/or slide support element 416 within the same chamber compartment that contains the reaction compartments 414. In one embodiment of the invention, the optical scanner of the X-Y-Z positioning device may scan the microscope slide on the slide support element to identify and record the location of the biological (tissue) specimen thereon. This information can be used to optimize the placement of the reagent on the microscope slide so that it is deposited directly upon the biological specimen or in a preferred location on the microscope slide for mixing or treatment purposes.

FIG. 35 shows a staining apparatus 400a which is similar to staining apparatus 400 except that staining apparatus 400a comprises (1) a pressurizable common chamber 446 wherein microscope slides on independent slide support elements 416a are exposed to the same pressurization level therein, and (2) a common application chamber (treatment chamber) 444 wherein reagents are applied to the microscope slides. Microscope slides are first inserted into a non-pressurized common application chamber 444 where a reagent is applied thereto by a reagent pack, and/or an X-Y-Z positioning device 430a. After application of the reagent to the microscope slide 446, the slide support element 416a passes into the pressurizable common chamber where each slide support element 416a is first sealed within the corresponding reaction compartment 414a also referred to herein as a corridor or enclosable compartment until the opening through which the slide support element 416a passes into the pressurizable common chamber 446 is closed or sealed. Once the slide support element 416a has been sealed within the pressurizable common chamber 446, the reaction compartment can be retracted to expose the microscope slide to the common pressure level established therein. The advantage of the embodiment of FIG. 35 is that there are fewer components necessary in comparison to the embodiment of FIG. 34, since in FIG. 34 each reaction compartment 414 is separately pressurized, wherein in FIG. 35 each "reaction compartment" 414a is not individually pressurized. Further explanation is provided below.

In the pressurizable common chamber 446 of the present invention such as is shown in FIG. 35 the slide support elements 416a can be moved into and out of the pressurizable common chamber 446 while said chamber is under pressure that is exceeding or is below atmospheric pressure while said pressure is maintained in the pressurizable common chamber 446 even when the independently moving side support elements 416a are moving into the pressurizable common chamber 446 to be treated or are being moved out of the pressurizable common chamber 446 for removal of the treated slide or for placement of a new slide on the slide support element 416a to be moved into the pressurized pressurizable common chamber 446 for treatment under pressure. The slide support elements 416a can be moved into and out of the pressurizable common chamber 446 without changing or releasing or diminishing the pressure therein. The movement is such that each slide support element 416a is moved through a corridor or reaction compartment 414a that is sealed when the reaction compartment 414a is sealed at seals 442 to the wall 440 which separates the pressurizable common chamber 446 from the application chamber (treatment chamber) 444 that isolates the slide support element 416 from the inner space of the pressurizable common chamber 446. The individual corridor or reaction compartment 414a is able to be sealed at its proximal end to seal the proximal end against the wall 440 of the pressurizable common chamber 446 having openings through which the slide support element can pass. This seal 442 can be any sealing means contemplated herein or any other sealing means able to function in accordance with the invention. The individual independently moving slide support element 416a within the corridor or enclosable compartment 414a could now move through an opening in the wall 440 of the pressurizable common chamber 446 while inside the sealed inner space of the sealed compartment 414a. Even after the slide support element 416a has moved through the access opening of the pressurizable common chamber 446, the enclosable compartment 414a or corridor remains sealed over the opening in the wall to maintain pressure within the chamber 446.

Figure 36:
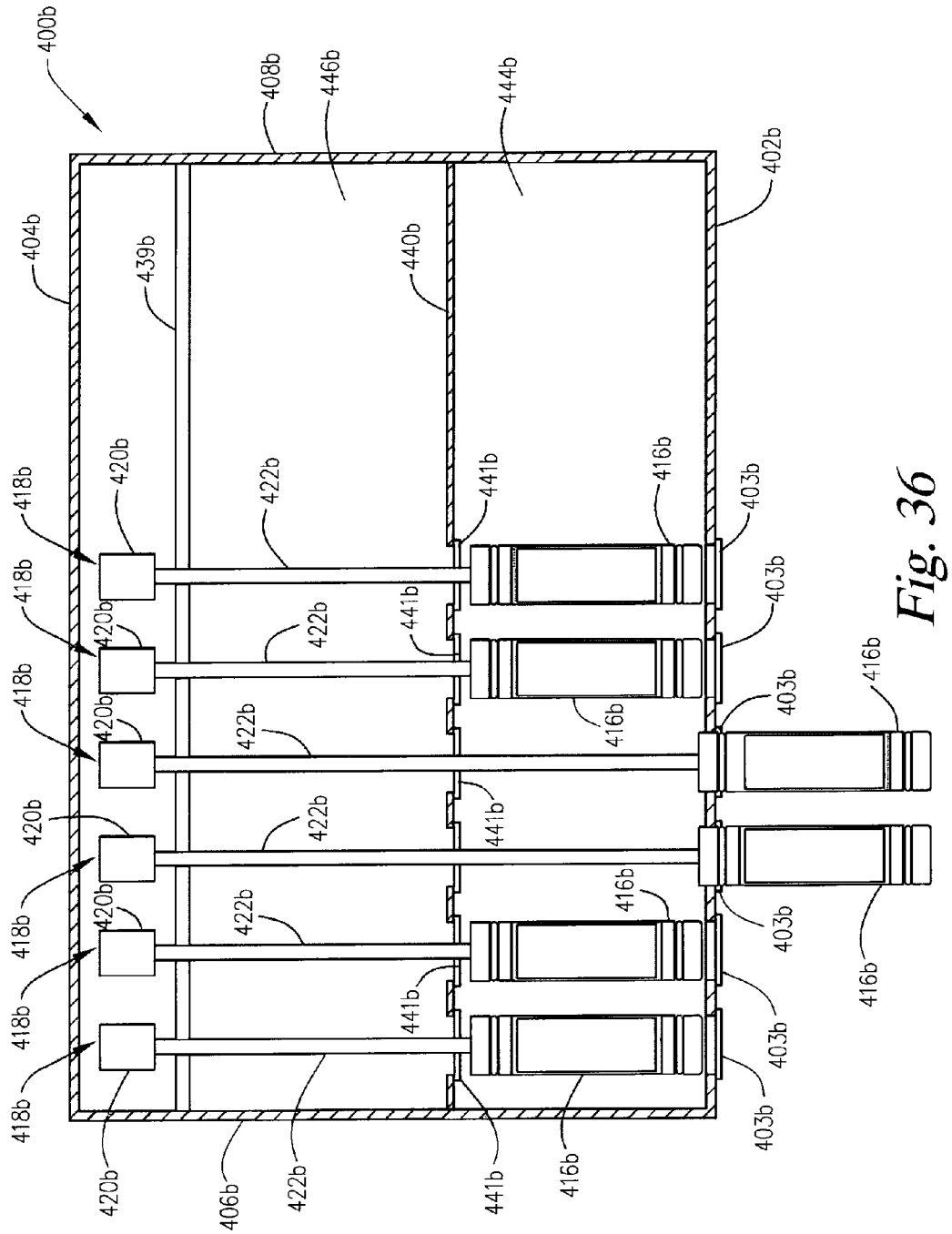
FIG. 36 is a top plan view of an apparatus similar to the staining apparatus of FIG. 4 except in place of separately pressurizable reaction compartments, the apparatus comprises a pressurizable common chamber into which the slide support elements can be withdrawn and treated under a common pressure level.

FIG. 36 shows a staining apparatus 400b which is similar to staining apparatus 400a in that staining apparatus 400a comprises (1) a pressurizable common chamber 446b wherein microscope slides on independent slide support elements 416b are exposed to the same pressurization level therein, and (2) a common application chamber (treatment chamber) 444b wherein reagents are applied to the microscope slides. Microscope slides are first inserted through a door or sealing means 403b into the non-pressurized common application chamber 444b where a reagent is applied thereto from a reagent pack, and/or optionally an X-Y-Z positioning device (not shown) supplied from a remote source. After application of the reagent to the microscope slide 446b, the slide support element 416b passes through a door 441b into the pressurizable common chamber 446b where each slide support element 416b is sealed therein upon closure of the door (or sealing means 441b. Once all slide support elements 416b have been sealed within the pressurizable common chamber 446b, the common pressure level can be established therein and the treatment protocol can proceed. In the embodiment of FIG. 36 all microscope slides are exposed to the same pressure level.

Referring now to FIGS. 37A-39B, the present invention is further directed to a novel method of applying (spreading) a reagent to a microscope slide or analytic plate or substrate having a biological specimen attached thereto. In one embodiment of the invention, the reagent is a DNA or RNA "probe" but may be any reagent described herein, including a liquid adhesive material. Such probes are well known in the art. Probes or "probe mixtures" (and other reagents) are expensive and it is an object of the present invention to provide a technique that efficiently applies the reagent mixture to the microscope slide to optimize coverage thereover yet which uses only a minimum amount of the reagent mixture. The amount of a reagent, such as a probe, that is routinely used to perform manual in-situ hybridization is 10 µl under a standard 22 mm×22 mm cover slip. The present invention contemplates utilization of the similar volume of reagent (e.g., 10 µl) but can evenly spread this quantity of probe mixture across a surface area greater than 22 mm×22 mm.

Referring in particular to FIGS. 37A-37F, an example of such a spreading device is shown. The spreading device 500 has a gap 502 that, for example, is 3-25 µm deep (but may be deeper). Typically, a tissue specimen (biological specimen) 504 used for in-situ hybridization is placed on a microscope slide 506. The microscope slide 506 has a label end 508 and a treatment surface 510. The thickness of the tissue specimen 504 is typically between 2-7 µm and more preferably between 4-5 µm. Thus the gap 502 of the spreading device 500 preferably has a depth that is 1-23 µm higher than the tissue specimen 504; or 2-15 µm, or 3-10 µm, or 5-7 µm above the tissue specimen 504. The spreading device 500 can be, for example, one inch wide and have end blocks 512 that are up to 1 inch in length and generally 0.01-5 µm in width. These end blocks 512 thus touch the microscope slide 506 0.01-5 µm from the edge of the microscope slide 506. The space between the two end blocks 512 and the microscope slide 506 encompasses the gap 502 of the spreading device 500. Preferably the depth of gap 502 extends at least 0.01 µm-50 µm above the highest point of the tissue specimen 504 on the microscope slide treatment surface 510. Preferably the depth of gap 502 is 0.1-5 µm, or more preferably 1-3 µm above the tissue specimen 504 to be covered by the reagent 514 disposed thereon.

The depth of the gap 502 of the spreading device 500 determines the thickness of a layer 516 (also referred to herein as a film or coating) of the reagent 514 that can be spread across the microscope slide 506 evenly. The thickness of the layer 516 is important so the reagent 514 forms a film or coating that is distributed evenly across the treatment surface 510 and the tissue specimen 504 thereon with the predetermined thickness of the gap 502 of the spreading device 500. The length of the spreading device 500 (measured from across the width of the slide 506) can be any size to accommodate the tissue specimen 504 on the slide 506. Tissue specimens 504 can be of any size in the art that can be placed, for example on a microscope slide 506 or other appropriate analytic plate. Even a very tiny tissue specimen 504 can have a thin coating of reagent 514 spread across its surface by the spreading device 500 of the present invention. For example, the total length of the spreading device 500 could be as little as 3-5 mm, wherein the length of the gap 502 across the length of the spreading device 500 is generally about 1-4 mm. In this version, the width of the layer 516 would be 1-4 mm, and the thickness would be the depth of the gap of the spreading device 500. In an alternate embodiment (FIG. 37B), a spreading device 500*a* is like spreading device 500 except it comprises block portions 512*a* which extend about a portion of the underside of the slide 506. The spreading device 500*a* may have a handle 518 to enable it to be moved manually. The spreading device 500 may be moved across the microscope slide 506 along a track 520 which may be operatively associated with a motor or other means of causing movement of the spreading device 500.

In one example, the tissue specimen 504 is a prostate or breast biopsy sample which is 1 mm wide and 1.2 cm long. A very small spreading device 500 as described above could be used to lay a thin layer 516 of reagent 514 over the entire tissue specimen's width and length. The spreading device 500 (or 500*a*) of the above example could be about 3 mm wide and have a gap depth of 6-7 µm in gap 502. A 2-4 µl drop of reagent 514 could then be used to lay the thin layer 516 over the tissue specimen 504 by movement of the spreading device 500 (or 500*a*) thereover without any waste of reagent 516. The spreading device 500 (or 500*a*) of the present invention can be of any size that is necessary to lay a thin layer 516 of reagent 514 over a biological (tissue) specimen 504 on a substrate such as a microscope slide 506. Other biological testing substrates are known and can be used with the present invention such as Petri dishes, plates of glass or plastic, and others as discussed elsewhere herein.

The spreading device of the present invention preferably has a gap 502 preferably is at least 0.01-20 µm above the tissue specimen 504. The thickness of the tissue specimen 504 is between 3-7 µm and more preferably between 4-5 µm. The spreading device 500 (or 500*a*) of the present invention may have a gap that is 4-10 µm and more preferably between 6-7 µm or just one, two, or three µm above the biological specimen. The gap depth of the spreading device can be, for example, 0.01 µm, to 0.1 µm, 0.1 µm to 1 µm, 1 µm to 20 µm, 20 to 50 µm above the microscope slide's 506 surface. Preferably the thickness of gap 502 is 1-3 µm above the specimen 504 to be covered by the reagent or solution film. The thickness of the gap 502 determines the thickness of the layer 516 or film of reagent 514 that can be spread across the slide 506 evenly. The thickness is important so the reagent 514 forms a layer 516 that is distributed evenly across the microscope slide 506 and specimen 504 with a thickness of the gap of the spreading device 500 (or 500*a*). The length of the spreading device 500 (or 500*a*) can be any size to accommodate a biological specimen. The reagent 514 that can be spread by the spreading device 500 (or 500*a*) can be any reagent used in a laboratory setting including, but not limited to: stains, probes, DNA and RNA molecular probes, immunoreagents, histochemical reagents, antibodies, in-situ reagents, mineral oils, ionic or non-ionic reagents additives, SDS, Tween, Brij, detergents, alcohols, polyols, glycols, de-waxing solutions, hydrating solutions, fixatives, detection reagents, thermoplastic resins, plastic polymers, cover slip mountants for coverslipping the specimen without the need for plastic or glass cover slips, fixatives, etc.

When using the spreading device 500 (or 500*a*) of the present invention on a microscope slide 506, the initial position of the spreading device 500 (or 500*a*) could be at either terminal end of the treatment surface 510 of the microscope slide 506. The distal end away from the label end 508 of the microscope slide 500 (the non-label end) is a preferred initial starting position (FIGS. 37C-37D). The reagent 514 is placed as a drop in front of the spreading device 500 (or device 500*a*) (FIGS. 37C-37D), then the spreading device 500 is moved over the drop of reagent 514, over the tissue specimen 504, and to the label end 508 of the slide 506 thereby depositing the layer 516 of reagent 514 evenly across the slide (FIG. 37E). Once the spreading device 500 (or 500*a*) has touched the drop of reagent 514, the reagent 514 spreads across the gap 502 of the spreading device 500 (or 500*a*) by capillary action and the spreading device 500 (or 500*a*) is moved slowly toward the label end 508 of the microscope slide 506. The end blocks 512 (or 512a) pass lengthwise over the peripheral side edges of the microscope slide 506. The reagent 514 is thus spread evenly under the gap 502 of the spreading device 500 (or 500a) across the microscope slide 506. The spreading device 500 (or 500a) is then retracted to the starting position on the slide (FIG. 37F). The thickness of the layer 516 of reagent 514 deposited is dependent on the viscosity of the reagent 514 and the depth of gap 502 of the spreading device 500 (or 500a). The viscosity of the reagent 514 can be of any viscosity known in reagents for laboratory testing. In one example, the viscosity may be that of mineral oil at ambient room temperature. Molecular probe dilutions have similar viscosity to mineral oil and this is a viscosity that can be used by this method of the present invention.

The spreading device 500 (or 500a) of the present invention can be disposable or reusable. The spreading device of the present invention can be molded out of plastic, thermoplastics, polymers, metal, glass, ceramic, and/or rubber, or combinations thereof, and can be labeled or color-coded to indicate the thickness the gap of the spreading device. The spreading device may be constructed of metal and coated with a polymer or plastic. In one example, a spreading device may be rated as having a gap of 6 μm, and has that numerical number stamped thereon, and has a particular color such as blue. This "blue" applicator when used would lay down a reagent layer with a thickness of up to 6 μm across the microscope slide for example. In an alternate embodiment, the spreading device can have a handle attached thereto for manual use (see FIG. 37B), or other appendages for the attachment to an automated instrument described in further detail below. The spreading device can spread a layer of a film or any reagent used in the laboratory setting such as, but not limited to: stains, probes, DNA and RNA molecular probes, immunoreagents, histochemical reagents, antibodies, detection reagents, thermoplastic resins and mountants for coverslipping the specimen without the need for plastic or glass cover slips, or fixatives.

As noted above for FIGS. 37-39, the spreading device is preferably automatically movable. The spreading device may comprise a plastic or polymer coated metal gap applicator which can be moved by a moving magnet present in the slide support element. The reagents used with the spreading device can have detergents present to help the spreading out of the reagents. These detergents are ionic or non-ionic detergents, glycols, polyols, etc.

As explained elsewhere herein, in one version of the method of using the spreading device 500, a microscope slide is placed on the slide support element, the correct spreading device is loaded onto the slide support element and rests on the slide, the microscope slide is moved into the staining apparatus to the treatment and application position, a reagent is either dispensed by the reagent pack, X-Y-Z dispenser, dispensing element, a remote source, or the reagent is dispensed from the dispenser integrated into the spreading device, the spreading device moves across the microscope slide and over the biological specimen to lay down an exact thickness of reagent equal to the thickness of the gap of the spreading device, the microscope slide is incubated and rinsed, and another reagent then can be dispensed onto the slide or the dispensed reagent can be spread again by the spreading device until the protocol is complete. If the slide is to be coverslipped by the spreading device the final reagent would be applied to the dried microscope slide and a coverslip mountant would be applied to front of the spreading device which would move across the slide to lay down an exact thickness of coverslip mountant to the slide. The slide is then heated to dry and harden the coverslip reagent and the slide is then removed and can go directly to the microscope for evaluation by a technician.

In reference to FIGS. 38A, 38B, 39A, and 39B, the slide support elements and associated reaction compartments contemplated herein (such as, but not limited to, slide support element 310, and reaction compartment 316) can be modified to incorporate the spreading device 500 (or 500a) described herein. The spreading device 500 for example, can be attached to a portion of an automated push-pull mechanism 522 which could pull and/or push the spreading device 500 over the microscope slide 506 to automate the entire spreading process (FIG. 39A, 39B). The spreading device 500 may have pins or some means to attach the spreading device 500 to the track 520 on the slide support element 310 or adjacent thereto or elsewhere around the slide support element 310 to move the spreading device 500 over the treatment surface 510 of the slide 506. The spreading device 500 or 500a may be attached to the extendable push-pull mechanism 522 via a pin 524 for example. Each reaction slide support element 310 and/or reaction compartment 316 of the staining apparatus 300 (or other staining apparatus contemplated herein) can have the ability to utilize these spreading devices to spread reagents upon the microscope slides 506 positioned thereon. Shown in FIGS. 39A-39B is an embodiment of an automated push-pull mechanism 522 for moving the spreading device 50. When the microscope slide 506 is placed on the slide support element 310 before testing is started, the technician could position the spreading device 500 to the instrument and at the appropriate time a reagent 514 could be deposited on the microscope slide 506 and the spreading device 500 could then be moved over the microscope slide 506 to evenly apply the reagent 514 over the tissue specimen 504. Once the entire staining process (the entire treatment protocol) is complete the technician could remove the microscope slide 506 and spreading device 500 and discard or clean the spreading device 500. In a preferred embodiment the spreading device 500 is color coded and is disposable.

In an alternate embodiment, the spreading device 500 (or 500a) described herein can have the reagent already contained within a reservoir in the spreading device 500 (or 500a) and dispensed therefrom onto the microscope slide 506. When loading the staining apparatus 300, the technician could remove a protective cover or closure device on the spreading device to expose the reagent to be applied to the microscope slide 506. In accordance with the invention, the technician can place the microscope slide and spreading device onto the slide support element 310. Once the slide support element 310 and microscope slide 506 thereon is inside the reaction compartment 316, the reaction compartment 316 can be depressurized or held in a vacuum. This vacuum environment can pull the reagent out of the spreading device reservoir and onto the microscope slide and the spreading device can then move and spread the reagent over the microscope slide as described above. In an alternate embodiment, the reaction compartment 316 can be under pressure to expel the reagent from the spreading device reservoir. In an alternate embodiment, the spreading device is attached to an armature on the X-Y-Z positioning device and is movable thereon, rather than on the slide support element or on a reagent pack.

Shown in FIGS. 40-42 is an alternate embodiment of a reagent pack of the present invention designated therein by the general reference numeral 550. Reagent pack 550 has round configuration such as a disk shape. The reagent pack 550 comprises a plurality of "pie-shaped" container portions 552 each having a reagent container 554 thereon, and a central aperture 556 through which a pin or other holding device on a reagent pack support device of the invention can engage the reagent pack 550. The reagent pack 550 operates by being rotated to an application position wherein a reagent in the reagent container 554 can be expelled onto a microscope slide on a life support element of the invention. Reagent pack 550 is shown as comprising eight container portions 552 but it will be understood by a person of ordinary skill in the art that the reagent pack 550 could comprise 1, 2, 3, 4, 5, 6, 7, 8, 9, 10, 11, 12 or more container portions 552 rather than the eight shown herein. FIG. 41A shows reagent pack 550 taken through line 41A. In this embodiment the container portion 552 comprises a "blister" or "bubble" container 554a which is designated to be "crushed" open. FIG. 41B shows an alternative version of container portion 552 taken through like 41B of FIG. 40 showing a "piston" type container 554b wherein the reagent in the container 554b is expelled by compression of a "piston" in the container 554b which causes expulsion of the reagent therein through an aperture 560 therebelow. Represented by the reference number 558 in an embodiment of a spreading device 558 such as described elsewhere herein which can be used to spread the reagent over the microscope slide. Shown in FIG. 42 is a single container portion 552 of reagent pack 550 and tab slots 568 into which the connecting tabs 566 can be inserted wherein the plurality of container portions 552 can be connected into the reagent pack 550, or could be disconnected and rearranged and reconnected together. The tabs 566 are not the only connecting means to connect the container portions 552 together and indeed any connecting device known in the art for use as a connecting means could be used as long as the resulting reagent pack 550 functions in accordance with the invention. Further, the circular reagent pack may be of integral, unitary construction, that is, the reagent pack may not be constructed of separable "pie" portions but may be constructed of a solid base.

Shown in FIGS. 43A-43B in cross-section is a staining apparatus 580 which is the same and other staining apparatuses contemplated herein except as described below. Staining apparatus 580 has a front wall 582 and, inner space 584, and a slide support element 586 having a sealing end 590 and sealing means 596. The slide support element 586 is sized to fit into a reaction compartment 588 in a manner similar to other slide support elements and reaction compartments described herein except that when slide support element 586 is inserted into reaction compartment 588 (for sealing a microscope slide therein), the sealing end 590 of the slide support element 586 sealingly engages with a mating surface on the front wall 582 to form a seal between the end portion 590 of the slide support element 586 and the front wall 582 as indicated in FIG. 43B. An advantage resulting from this embodiment of the invention is that a separate door is not necessary to close the aperture in the front wall 582 through which the slide support element 586 is passed. A reaction pack support device of the invention could have a similar sealing means in an end portion thereof. Preferably the sealing end 590 is a ground or polished glass surface as is the mating surface on the front wall 582, or it could be any similarly ground or polished surface in the material from which the sealing end 590 of the slide support element 586 is constructed. The opposite end of the slide support element 586 could have a similarly configured sealing end portion and in an alternate embodiment, the sealing end 590 of slide support element 586 could be designed to form a seal in a mating portion of an inner wall of an embodiment of the present invention wherein the staining apparatus comprises a pressurizable common chamber such as inner wall 440 of staining apparatus 400a or inner wall 440b of staining apparatus 400b. For example in staining apparatus 400b, the slide support element 416b could have a sealing end such as sealing end 590 which sealingly engages wall 440b for forming a seal therebetween, and which replaces the door 441b therein.

In a preferred embodiment of the present invention, a microscope slide is placed on the corresponding slide support element when it is in a position outside of the staining apparatus. The reagent pack specific for that particular microscope slide similarly would be placed on the corresponding reagent pack support device (wherein the loading position for the reagent pack support device is inside or outside of the staining apparatus). The reagent pack preferably would feature a bar code, OCR symbol, machine readable symbol or code that can be read by an optical scanner or scanners associated with the staining apparatus to determine what type of treatment protocol is to be performed on the corresponding microscope slide. Once the microscope slide has been placed on the corresponding slide support element the technician can place the appropriate reagent pack on its reagent pack support device and press a button nearby the slide support element or reaction compartment or front wall of the staining apparatus or on the screen of the microprocessor to start the treatment process. Since the lab technician knows what particular protocol that is required for each microscope slide positioned, in an alternative embodiment the tech would place the microscope slide on the slide support element corresponding thereto and place the reagent pack on its reagent pack support device and push the reagent pack or reagent pack support device gently into the staining apparatus. Once the reagent pack support device is moved about 0.1 to 1.5 cm manually towards the staining apparatus, the reagent pack support device will recognize this movement and will automatically continue movement of the reagent pack into the staining apparatus without further assistance from the technician. The independently movable slide support element can, at this time, automatically move into the staining apparatus when the reagent pack support device begins to automatically move into the staining apparatus or shortly thereafter. Once the slide support element and the reagent pack support device (and reagent pack) are inside the staining apparatus, the microprocessor will recognize that a new reagent pack has been moved into the staining apparatus and the staining apparatus will position a movable optical recognition character reader or scanner over the reagent pack's optical character recognition (OCR) code and that particular code with be identified as a new protocol for the microscope slide associated with that reagent pack. Preferably, there is no further assistance needed from the technician once the reagent pack support device is automatically moved into the staining apparatus. The microprocessor will take over and all the information from the OCR code on the reagent pack will be deciphered to start a new treatment protocol to the corresponding new microscope slide. Since the microprocessor recognizes the OCR code present on the reagent pack, the staining process will then be carried out by all the automated processing devices under its control. Preferably, there is no need to have an OCR code on the microscope slide to link the slide with its reagent pack. This one step identification, of the present invention, is preferred versus the prior art identification of slides and reagent container where both the slide and the reagent container need to have OCR code present thereon to locate and dispense the right reagent to the right slide. This saves money and time by not placing an OCR code on the prior art microscope slide to be processed by automation. An alternate version of identifying the reagent pack is the reagent pack can have any wireless device know in the art of recognizing wireless devices by a microprocessor. The reagent pack can have, for example, a wireless device embedded or on the reagent pack. The reagent pack can have embedded information in the form of microchip or other device to store the protocol information that can be recognized and deciphered by the microprocessor. When the protocol and slide processing is completed, the microprocessor will alert the technician that the microscope slide is ready to be removed from the staining apparatus. This alert can be is form of a sound and/or visual effect either near the particular slide support element or front wall of the staining apparatus or on the microprocessor's screen. The notification that the treatment protocol is completed and the slide can be removed from the staining apparatus can be provided by any known device or devices both audible and/or visually known in the art of notification of microprocessor controlled devices. A preferred notification is both an audible alert, which can be of different sounds or pitches relating to the entire process from start to removal of the microscope slide, along with a visual alert on the staining apparatus or on the screen of the microprocessor.

Each slide support element of the present invention preferably has a slide support eject button, associated therewith and each reagent pack support device preferably has a reagent support eject button associated therewith. Each set of reaction components preferably comprises a protocol status indicator light or lights, "quick code" buttons, and a LCD or LED screen for visual information regarding the protocol, reagent(s), and or microscope slide.

The regent pack, strip or individually contained reagent or reagents preferably features a bar code, OCR symbol, machine readable symbol or code or other similar symbol that can be read by the apparatus's optical scanner or scanners to determine what type of protocol is to be performed on the corresponding microscope slide. The reagent pack, strip, or individually contained reagent or reagents or the microscope slide can also have a "quick code" that corresponds to a "quick key" or "hot key" on the apparatus that can be entered into the apparatus manually to identify the treatment protocol for a particular slide. Once the microscope slide is placed on its slide support the technician would place the desired reagent pack on its reagent pack support device and press a button nearby the slide support element or reaction compartment on the front wall of the staining apparatus front panel or microprocessor screen to start the treatment process. Since the lab technician knows what particular protocol that is required for each microscope slide positioned on its independently moving slide support element, in an alternative embodiment the technician would place the microscope slide on its slide support element and place the reagent pack on its reagent pack support device and push the start button on the apparatus to initiate the automatic independent movement of the slide support element and reagent pack support device into the inner space of the staining apparatus of the apparatus. The apparatus would then read the OCR code or symbol on the reagent pack to program the microprocessor for that particular treatment protocol for the microscope slide on the slide support element. The microprocessor with take over and all the information from the OCR code on the reagent pack will be deciphered to start a new treatment protocol to the corresponding new microscope slide. The apparatus can also read the slide's OCR code or symbol, if present, to confirm that the reagent pack selected by the technician correlates to that particular microscope slide. In an alternative embodiment, the reagent pack's OCR code can be manually scanned by a wired or wireless hand held scanner for the manual programming of the treatment protocol. The user would place the microscope slide onto a slide support element and either scan the OCR code of the reagent pack prior to putting the reagent pack on the reagent support or after the reagent pack is placed onto the reagent pack support device. The apparatus would then start the protocol by automatically moving the slide and reagent pack into the apparatus. In an alternate embodiment, the user programs the apparatus for a particular treatment protocol by entering into the apparatus or staining module a "quick code" that is present on the reagent pack. This "quick code" can be a number, symbol, letter, or identified by a particular color code. For example, a number "2" can be present on the reagent pack, or the letter "C" or particular color code like "blue". The user would place the microscope slide on the corresponding slide support element then place the required reagent pack on the reagent pack support device and press the "quick key" on the apparatus that has the same number, letter, or color code that is present on the reagent pack. These quick codes can also be on the microscope slide and/or the reagent pack. The "quick codes" are useful when common or repetitive protocols are used. This speeds the time of programming the apparatus for a particular repetitive protocol. For example, if the user has five "estrogen receptor" protocols to be analyzed at one time, the user would place the five slides onto their corresponding slide support elements and place the 5 reagent packs for the "estrogen receptor" protocol onto their reagent pack support devices. The user would then press or activate the individual "quick code" button or icon for that staining module that corresponds to the estrogen receptor protocol's "quick code" for each microscope slide. For example, the "estrogen receptor" protocol is part of a staining protocol class known in the art as a "prognostic" test. Since all prognostic tests could have the same incubation times, the "prognostic class" of antibodies could all have the same "quick code". The user can now program all the "prognostic" protocols for each "prognostic" slide by pressing or activating the single "quick code" button to program the apparatus for a "prognostic" protocol. Seven slides for a "prognostic" panel could have, for example, seven prognostic antibodies like estrogen receptor, progesterone receptor, Ki-67, Her-2, bcl-2, p-glycoprotein, and p53. The user would place each microscope slide on its corresponding slide support element and then place the reagent pack for that "prognostic" antibody test and then press or activate, for each of the sets of reaction components, the "quick code" button. The programmed incubation times would be the same for each module even if the antibody test was different for each slide. Because this class of antibodies being used, in this example the "prognostic" antibodies, all have the same "quick code" on their reagent pack or slide, different prognostic reagent packs can have different prognostic antibodies present but all have the same protocol when it relates to the incubation times for the whole class. Another class known in the art are the "core" antibodies. These antibody protocols also have different primary antibodies in each reagent pack, but the incubation times can be the same. The "core" antibodies can all have the same "quick code" presented on their reagent pack. They can all be a different antibody test or protocol only they all have the same incubation times for each step. An example of this type of class of antibodies tests can have the letter "A" on their reagent pack. The user would then press or activate the "A"

button associated with the staining module and the test would start. The "quick code" buttons can be pre-set at the factory or can be user manipulated depending on the user preference. Each "quick code" button can be programmed with a different protocol incubation time or any other variant relating to protocol method and stored for future use with that "quick code" button. It would be known that any variant to this method can be used. Whether the slide is placed first and the reagent pack is placed second or vice versa is anticipated. Also whether or not the slide support element or reagent pack support device are moved into or are outside of the apparatus before operation is contemplated. Any step of moving of the slide support element or reagent pack support device, either semi-automatically or completely automatically is contemplated. The steps of placing the microscope slide on the slide support element, the placement of the reagent pack on the reagent pack support device, automatic scanning of the OCR code, manual scanning of the OCR code, and pressing or activation of the "quick code" buttons can all be used in any combination, method and or sequence. Each individual slide support element can automatically move outside the staining apparatus to place a microscope slide thereon or for removal of the microscope slide when a test is complete by pushing the slide support eject button on the apparatus. The slide support element and reagent pack support device can also be semi-automatically moved outside or inside the staining apparatus by manually moving the slide support element or reagent pack support device about 0.1 to 1.5 cm thereby activating their automatic movement mode. Once the slide support and/or the reagent support is manually moved about 0.1 to 1.5 cm inwards towards the staining apparatus or moved towards the front wall thereof, the slide support element and/or the reagent pack support device would recognize this manual movement and the apparatus will take over by automatically moving the slide support element and/or reagent pack support device into or out of the staining apparatus. This movement is operationally similar to the mode of operation of a computer CD-ROM drive door or drawer of DVD machine drawer. In an alternate embodiment the slide support element and the reagent pack support device can move totally automatically and independently by pushing a button on the staining apparatus to initiate said movement. A button for insertion or ejection of the slide support element and reagent pack support device can be present for each set of reaction components on the front panel (front wall) of each staining module. The insertion/ejection button can be a single button for moving both or may comprise separate buttons for each movement.

As explained elsewhere herein, the slide support element and the reaction compartment can be made out of glass with a polished seal matingly sealing the inner surface of the reaction compartment and the outer surface of the slide support element. For example, a glass syringe commercially available from Popper and Sons can be modified for this embodiment. A Perfecktum™ glass hypodermic syringe (cat no: 5159, 50 cc syringe) or equivalent could be modified to produce a glass slide support element (constructed from the inner barrel or plunger of the syringe) and a glass reaction compartment (constructed from the outer barrel of the syringe). The sealing means is the polished glass between the inner barrel (the slide support element) and the outer barrel of the syringe (the reaction compartment). This polished glass mating seal between the slide support element and the reaction compartment enables the slide support element to be easily moved into and out of, and rotated within, the reaction compartment. For example, the slide support element can be tilted, spun, or otherwise rotated within the reaction compartment as well as be moved laterally forward and backwards while in the reaction compartment. The advantage of this design is that the slide support element, inside the reaction compartment is able to move forward, backwards, and in a circular motion (rotated) while forming and maintaining a pressure tight seal inside the reaction compartment formed by the polished glass seal between the slide support element and reaction compartment. The circular, rotational, motion is ideal to "spin" the slide support element to cause removal of a reagent or wash solution from the slide by centrifugal force. The reagent is "spun" away from the microscope slide and drained from the reaction compartment and is then ready for the next reagent or can be "spin dried" prior to remove of the microscope slide from the slide support element. The slide support element, because of the polished glass seal, is very easily moved within the reaction compartment. For example, in one version, a simple twist of the slide support element can cause the slide support element to make several revolutions within the reaction compartment even if the reaction compartment is under positive (or negative) pressures that exceed (or are below) atmospheric pressure. The microscope slide can be in any position to be washed by a wash reagent dispenser and then, if necessary blown off by a gas pressure dispenser, with the slide at any angle on the slide support element. The home position for the microscope slide is when the upper surface of the slide faces upward (the "12:00 o'clock" position or 0°). The slide could be washed at the 12:00 o'clock position, the 3:00 o'clock position (90° from home position), the 6:00 position (180° from home position), 9:00 position o'clock (270° position) or any degree position between the home position (0°) and 360° from home position. The preferred positions for washing the slide would be between the 0° position (home position) and 180° (6:00 position). Slide processing devices can be positioned anywhere around the slide support elements to dispenses reagents, gas, or other processing device proposes at any angle the microscope slide is positioned on the movable slide support element. For example, the staining reagents (antibodies, molecular probes, biological stains, detection reagents, pre-treatment reagents, antigen retrieval solutions, or other reagent or solution described herein) could be dispensed to the microscope slide from above the slide support element in the home position ("12 o'clock" or "0 degree" position) and then the microscope slide could be rinsed at the "6:00 o'clock" position (180° position) by a rinse wash reagent dispenser and then spun dried to remove the wash reagent and then drained from the reaction compartment.

The electrical connections to each individual heating element or other electrical device on or in the slide support element or reaction compartment can be controlled by wireless connections, Bluetooth® connections, impedance connections, or any other type of wireless connection to enable the free movement of the slide support element and reaction compartment in any direction or speed or speed of movement thereof. For example, the individual heating element that is part of the slide support element can be connected to the microprocessor wirelessly by those connections known in the art of connecting electrical devices wirelessly. This wireless connection of the individual heating element can thus be maintained when the slide support element or reaction compartment are in motion, for example, this enables maintenance of the heating current to the individual heating element when the slide support element is spinning while removing reagents by centrifugal force.

The reaction compartments and/or the slide support elements of the invention optionally are disposable. The disposable slide support element can be constructed of plastic or polymers that can support a microscope slide and be able to withstand the temperature and pressure requirements of the present invention. Pressures of 25-30 psig and temperatures of 100-160° C., for example, are possible with modern plastics, thermoplastics, and polymers. In one embodiment, the disposable slide support element is constructed without a heating element, rather the heating element used to heat the reagent to the above mentioned temperatures is placed within the walls of the reaction compartment rather than in the slide support element. A disposable reaction compartment is also contemplated. The disposable reaction compartment can be constructed using the same materials as said disposable slide support element. Heating elements for heating the microscope slide could be, for example, heaters that can be present outside of the disposable reaction compartment or disposable slide support element. In one embodiment, the heating element can be tubular and can contain, in its center, a disposable reaction compartment in a tubular shape. The walls of such a tubular heater could heat the tubular reaction compartment and thus heat the reagent associated with the slide support element. After a microscope slide has been treated the disposable slide support element, and/or the disposable reaction compartment can be removed from the apparatus and discarded. A new disposable reaction compartment can then be placed into the tubular heater and/or a new disposable slide support element can be placed in the staining apparatus for use. All the motions and controls of the present invention can be utilized with this embodiment of disposable reaction compartments and disposable slide support elements.

In an alternate embodiment of the invention, a plurality of slides are processed (either separately in individual reaction compartments or within a common vessel) by applying a reagent or solution to the slide and pressurizing the vessel above atmospheric pressure to levels as discussed elsewhere herein, wherein the biological specimens, biochemicals, or other biological entity on the slide is not subjected to additional heating.

As described elsewhere herein, preferably the slide support element, reaction compartment, reagent pack, reagent pack support device, dispensing element, ports, conduits, mixing jets, pressurizing means, cooling means, aspiration devices, drainage ports, heating devices, and reagent conduits are independently operable and independently movable.

The in situ antigen recovery and staining apparatus of the present invention preferably has as one component a device for reading or detecting an optical character or code which identifies a reagent pack or reagent pack component such as a tile or container.

As noted above, "stirring" of the reagent on the microscope slide can be performed by applying a gas stream onto the microscope slide to impart a circular motion of the reagent on the microscope slide. Alternatively, the mixing of the regents can be from sonic, ultrasonic, and or vibratory waves passing through the reagent causing agitation of the reagent on the microscope slide. These waves cause a physical movement of the static fluid state of the reagent. The movement of the reagent causes the liquid phase to move or mix the reagent on the microscope slide and increase exposure of the reagent to the biological specimen thereby increasing the reaction of the reagent with the biological specimen on the microscope slide. Further, these mixing processes can be useful in agitating a rinse reagent to effectively remove the unbound reagent from the biological specimen thus producing a stained biological specimen with low or no background staining. These mixing processes can be on the surface of the liquid and/or the center of the liquid and/or the bottom of the liquid to agitate or mix the reagent.

These mixing processes act to decrease the time necessary to process a biological specimen present on the microscope slide. The liquid reagent must come in intimate contact with the biological specimen for the biological reaction to take place. The staining of biological specimen with biological stains, monoclonal antibodies, polyclonal antibodies, molecular RNA and DNA probes, immunoreagents, detection reagents, chromogens and counterstains and other such reagents, also referred to herein as "reagent elements" utilize heat and time to passively produce the required reaction of these reagents with the biological specimen herein know as "biological elements". One embodiment of the present invention utilizes a magnetic field to "direct" these "reagent elements" to their respective targets associated with the biological specimen. A magnetic field can be generated from below, above, or adjacent the microscope slide with an electromagnet which is capable of reversing its polarity. This electromagnet of the present invention can impart a powerful magnetic field to align a "regent element" and draw it towards the biological element present in the biological specimen. The electromagnet and method of use herein is contemplated. Reagents like monoclonal and polyclonal antibodies are known and used routinely in the detection of biological antigens. These testing antibodies are uniquely attracted by their corresponding antigens present in the biological specimen. This embodiment of the present invention utilizes electromagnets below the biological specimen to "align" and "pull" these antibodies toward the biological specimen therefore decreasing the processing time of these antibodies versus simply passively placing the antibodies on the biological specimen in the prior art methods. In this embodiment of the present invention an electromagnet or permanent magnet is placed in or adjacent the slide support element that supports the microscope slide and its biological specimen thereon. The reagent is placed on the upper side of the microscope slide and the electromagnet is energized with an appropriate polarity required to produce a magnetic field between the top side of the liquid reagent and the topside of the microscope slide with the biological specimen between the top side of the liquid reagent and the top side of the microscope slide. This magnetic field in this embodiment of the present invention pulls the regents elements (e.g., antibody, probe, stain) toward the top side of the microscope slide. As the magnetic field pulls and directs the reagent elements toward the top side of the microscope slide, the reagent elements pass through or closely thereto the biological specimen and effectively and efficiently physically attach to or associate with their respective biological elements. If the desired reagent element has a net positive charge on its active binding site, the electromagnet or magnet would impart a net negative charge to attract and pull the reagent element toward the biological element, for example. If the reagent element has a net negative charge on its active binding site, then the electromagnet or magnet would impart a positive magnetic field to attract the reagent element toward its biological element, for example. The entire processing protocol, relating to positive and negative field generation, by the electromagnet or magnet, is controlled by the microprocessor and is directed according to the protocol selected. The liquid reagent can be of any type and composition known in the art of staining microscope sides. The composition of the diluents present in the prior art compositions for diluting the active reagent are known and can be use with the present invention. The preferred embodiment of the present invention utilizes the magnetic field alone to have a direct effect on the reagent element or elements present in the liquid testing reagents of the prior art. No alteration or additional chemicals, other than the known standard liquid reagents diluents or standard buffers, are necessary for the method of the present inventions wherein an electromagnet or magnets is used to cause a direct pull and moving effect on the reaction element in relation to the biological elements. The present invention may use only the magnetic field generated by the electromagnet or magnet to act specifically on the reagent elements present in known diluting buffers, regardless of the type of diluting buffer used to make a working solution of liquid reagent. The present invention method is not dependant on the solvent or buffer being used to dilute the reagent elements for testing. The present invention preferably relies only on the net charge of the reagent element present in the known and widely accepted diluents buffers along with a very strong magnet either an electromagnet, permanent, superconducting, and or resistive magnet. The Tesla rating of the magnet can be 0.000001 Tesla to 60 Tesla. One Tesla equals 10,000 Gauss. Preferably the Gauss rating can be 1 to 20,000 Gauss. Common diluents buffers are phosphate buffer saline and Tris® based diluents, with or without detergents present, and a preservative. The reagent elements need only to have a net positive or negative charge to be used with the embodiments of the present invention. The electromagnetic force imparted on the reagent element in combination with the high positive pressure or negative pressure in the reaction compartment, produces an environment that substantially decreases the amount of time needed to react a biological specimen with a reagent element. In a further embodiment of the present invention, a magnetic field is used to cause movement of reagent element about a biological element. For example, the buffer used or diluents to used dilute reagent elements can have iron or iron-like element present therein to be acted on by the magnets. The iron micro or nano particles are present to act as a motile device for mixing or agitation of the reagent elements about the biological elements. Micro or nano iron particles that are coated with an inert plastic or polymer can be used to mix, agitate, or move the reagent elements in their respective diluents. The micro or nano iron particles are moved by the magnet current supplied by the magnets present around the biological elements. Other magnetically moving particles are also contemplated. The reagent elements themselves can have attached to themselves iron or iron-like micro particles to move, mix, or attract reagents to the biological elements. Examples of these particles that can be acted on by magnets are particle like colloidal gold or biochemicals to which the colloidal gold is attached. Colloid gold is routinely conjugated to antibodies and nuclei acid probes. The colloidal gold can be seen in electron microscopy and light microscopy when developed by a silver enhancing protocol. The particle size of the gold particle is 1-10 nm but can be smaller or larger. The smaller the size of the gold particle is important because the extra weight of the gold particle attached to the reagent element is proportional to the movement and attachment sites of the reagent element to the biological elements. Examples of the present invention using magnets to mix, agitate, or move reagent elements are described. The colloidal gold particle is attached to a reagent element and the magnetic attraction of the gold particle is used to pull the reagent element towards its biological element. This movement reduces the time necessary for incubation times of the reagent element to "find" its biological elements. The magnetic conjugated reagent element being pulled toward the biological elements by the magnet, along with the pressure of the present invention leads to substantially reduced time of incubation. The micro particles can be any ferro containing particle (Fe) or other metal particles that can be moved by a magnet are know and contemplated. The particle can be of the size less than $1 \times 10^{-10}$, $1 \times 10^{-9}$, $1 \times 10^{-8}$, $1 \times 10^{-7}$, $1 \times 10^{-8}$, and up to $1 \times 10^{-5}$ meters.

The nano or micro-particles can be coated with a plastic, polymer, coating to help in the stability of the particles in solutions. The coating can be Teflon®, fluoropolymer, plastic, or ceramic. The particle can be by itself in the reagent diluents or attached to the reagent element. The particle can be soluble, at least partial soluble, or colloidal in the diluents solution. If the particle is not attached to a reagent element is would be used to mix or agitate the surrounding solution. If the particle is attached to the reagent element it can be for mixing, agitating, or moving the reagent element. In an alternative embodiment the diluents can have present a electrolyte present to produce a net charge of the reagent elements present and to further the effects of the magnet on the reagent elements.

Magnets that can be used in the present invention are contemplated as being permanent magnets, superconducting magnets, resistive magnets. The preferred embodiment is the use of a permanent magnet that has high temperature stability for the use in the present inventions chambered high pressure and high temperature conditions. High temperature stable permanent magnets such as described in U.S. Pat. No. 6,451,132 which is hereby incorporated by reference in its entirety, can be used. These magnets are represented by the general formula $RE(Co_w, Fe_v, Cu_x, T_y)_z$, where RE is a rare earth metal selected from the group consisting of Sm, Gd, Pr, Nd, Dy, Ce, Ho, Er, La, Y, Th, and mixtures thereof and T represents a transition metal(s) selected from the group consisting of Zr, Hf, Ti, Mn, Cr, Nb, Mo, W, V, Ni, Ta, and mixtures thereof. These high temp permanent magnets can be subjected to temperatures exceeding 700° C. These high temperature permanent magnets can be incorporated into the heating element of the slide support or adjacent thereof. These magnets can be a single high temperature permanent magnet that is constructed along with a conductive heating element producing the slide support base or pad where the slide touches the slide support. The magnet can have the heating source sandwiched between two magnets or the heating source can be above the magnet or below the magnet. The magnet itself can be the slide support element or a portion thereof which is able to be heated by a conductive type heating source or plate. The heating element can be on top, between, or below the magnetic slide support element. The magnet and heater can be separated from the slide by a glass slide support base, for example. The entire slide support element can be constructed out of high temperature glass like Pyrex® wherein the slide base, where the microscope slide is positioned and rests on, or in the slide support element during the staining protocol. Underneath such glass slide support base is the magnet and heater which is outside the slide support element in relation to the slide on the glass base. The heater alone or the heater and magnet can be sealed within the glass of the slide support element. This embodiment wherein the heater and or heater and magnet is sealed within the glass slide support insulates or protects the heater or heater and magnet from corrosive chemicals during staining. This insulation away from the inner space of the slide support element and or slide base by the heater is a preferred embodiment whether there is a magnet associated with the heater or not. With the embodiment of the slide support element and reaction compartment being constructed of glass or other material, which is describe elsewhere, preferably produces an environment of all glass surfaces touching the microscope slide and areas adjacent to the microscope slide as a preferred embodiment of the present invention. Since in this embodiment there is no non-glass exposed part of the slide support element when the slide support element is inside the glass reaction compartment any chemical that is corrosive or incompatible with metals or plastic can now be used. Any of the processing components can be insulated by the glass slide support or glass reaction compartment. The glass slide support element can have, molded within the glass, tabs or notches or other means present to align and hold the microscope slide to the glass microscope slide base holding the microscope slide on the glass slide support element. The magnetic field and the conductive heater can act on the microscope slide and specimen through the glass base of the slide support element with the advantage of the heater and magnet not being exposed to the chemicals of the inner compartment of the slide support element. Glass is a good conductor of heat and the magnetic field. Other magnets like Neodymium magnets are a type of permanent magnet that can have the ability to retain their magnetic properties even under very high temperature conditions. Most permanent magnets lose their magnetic properties when they are exposed to high heat conditions. The type of permanent magnet contemplated for the present invention has the grade of N42SH the "SH" grade of Neodymium permanent magnets can be used in temperatures over 150° C. Standard "N" grade permanents magnets have a maximum operating temperature of 80° C. A "SH" grade Neodymium permanent magnet with the dimensions of 2 inches long by 1 inch wide by one eighth inch has a Gauss rating of 3095 for its surface field strength. It also has a Brmax of 13,200 Gauss and a BHmax of 42 MGOe. This magnet could be just underneath the slide support element heating plate (heating element) for example or it may be incorporated into the heating plate or be part of the heating plate. The magnet can be automatically independently movable to change the polarity of the current in relation to the biological elements or reagent elements.

These permanent magnets can be of any shape or size to be used in the present invention. The mentioned magnets can be in the slide support element, the heating element or rod in the reaction compartment, or in reaction compartment walls. The magnet can be outside the slide support element and outside the reaction compartment and be adjacent to one slide support element and one reaction compartment or the magnet or magnets can be in the walls of the reaction compartment or positioned inside or outside the walls of the instruments case. Further, the automated instrument described above can be inside a bore of a magnet. The instrument describe above can be made of glass and of non-ferrous material to have all the advantages of being used under the strength of very powerful magnets.

As explained previously, the staining apparatus contemplated herein can use a reconfigurable, rearrangeable or configurable individualized reagent dispensing device such as a pack, strip, or single "dose" which comprises a carrier or holder for holding one or more individualized regent dispensers wherein the regent dispensers is movable for dispensing a desired sequence of reagents (or just a single reagent) to a biological specimen on the slide. Each such pack is individualized to be in association with only a single biological specimen on a slide. The pack and/or the reagent container thereon can be disposable or reusable. As noted above, examples of such packs shown in U.S. Published Application 2006/0275861 which is entirely incorporated herein by reference.

Various embodiments of the processes of the present invention include, but are not limited to, (1) application of a reagent to a slide using the present apparatus, and heating the slide, with or without a step of pressurizing the reaction compartment, (2) filling the base cavity with a reagent or solution such that it immerses the slide, pre-pressurizing the reaction compartment, then heating the slide and reagent solution in the base cavity, (3) filling the base cavity with a reagent or solution, then heating the slide and reagent or solution, without pre-pressurization before the heating step, or (4) placing a liquid in the bottom of the base cavity without the liquid directly touching the slide, then heating the liquid in the base cavity to cause vapor formation which pressurizes the reaction compartment and secondarily heats the slide and reagent therein (the slide also may optionally be heated by the slide heater).

Other aspects of the present invention are shown and described in U.S. Provisional Application Nos. 60/142,789; 60/684,047; 60/689,386 and 60/730,744, U.S. Patent Application Publication No. 2006/0275861, and WO 2006/127852, the entirety of each of which is hereby expressly incorporated herein by reference.

The heating element or plate of the slide support elements can be slightly smaller than the width of a microscope slide to facilitate remove of the slide from the heating plate. The width of the heating plate can be 1-6 millimeters, for example, less than a microscope slide width. A standard microscope slide is about 25 mm in width. The heating plate can be 23 mm, for example, in width to facilitate removal of the microscope slide off the heating plate.

The slide support element can have an ejection means such as a movable pin or lever underneath the microscope slide to push up a portion of the slide to facilitate removal of the microscope slide from the heating plate. These ejection means can be underneath one or more corners of the microscope slide for example. This movement can facilitate the cleaning underneath the microscope slide, removal of the microscope slide, or cooling of the microscope slide by moving the slide away from the heating plate.

The heating plate can have holes present for vacuum or pressure to be applied to the bottom of the microscope slide. Pressure exerted from these holes can push up the microscope slide to help remove the slide from the heating plate. The holes can also be used to help clean residual reagent that may be trapped underneath the slide. The process of using a rinsing liquid and the use of the vacuum or pressure holes in the heating plate provides a method of cleaning and drying the underside of the microscope slide.

The staining apparatus can have automatically leveling devices, reaction components such as slide supports and reaction compartments, pins, pegs, feet, or level sensors that are under the control of the microprocessor. When the apparatus is turned on the microprocessor will determine if the entire apparatus and or each reaction component is level. If it is not level or needs to be adjusted the leveling devices (stepper motors, pneumatic, electromechanical devices) in each leveling device, slide support, reaction compartment, pins, pegs, feet are moved in or out to level the entire apparatus or each reaction component. This is especially important when using the field models since they are moved more frequently. The main microprocessor can determine if the entire apparatus or each staining module is level each time the apparatus is turned on or a "level" icon can be available on the master microprocessor to level or check the levels at any time during a protocol.

The staining apparatus can produce a blast of air inside the reaction compartment of agitate a reagent or liquid therein to produce an emulsion.

Mixing a reagent on the microscope slide can be by at least one gas source blowing across the slide to stir the reagent. Mixing can occur by blowing at least one gas jet over the reagent and subsequently moving the slide support in at least one direction to agitate or mix a reagent or rinse a slide. Mixing is very efficient because the present invention utilizes agitated rinse or kinetic rinsing to dislodge unbound reagents from the biological specimen or the microscope slide. The kinetic movement can be by gas, physical movement of the slide, vibrations, agitation, ultrasound, etc. Kinetic movement can be for mixing or rinsing.

There can be a separate individual camera present on the outside front wall of each staining apparatus of the apparatus to see the label end of the microscope side or reagent pack information more clearly or increase the visual size of the microscope labeled end or reagent pack information. The camera can, for example, inversely project its image to improve viewing of the label end of the microscope slide for better identification of the name of the stain desired.

The reagent pack can have a RFID (radio frequency identification) tag or device for the apparatus to automatically identify the reagent pack and protocol program.

The apparatus can use non-refrigerated reagent packs for field and lab use to reduce necessary refrigeration space.

The reagent container, capsule, or vial can line up to the reagent conduit on the reaction compartment or window, or over the microscope slide and a vacuum can pull the reagent out of the capsule or vial without using the dispensing element to push the reagent out. The vacuum pulls the reagent out and the reagent drips onto the microscope slide.

There can be a plurality of movable reagent conduit lines each having a magnetic end to connect the reagent conduit line to the metal reagent conduit positioned on the reaction compartment. One of the heads on the at least one X-Y-Z positioning device can have a plurality of these movable reagents lines with magnetic couple ends to service one or a plurality of reaction compartment simultaneously with a remote reagent from a reagent container or bulk reagent bottle.

The X-Y-Z positioning device can be constructed so as to be able to pick up different types of spreading devices from a supply station and use them on the microscope slide to spread reagents. When the reagent is spread across the slide, the dispensing head, carrying the spreading device, can move to an ejection area to eject the used spreading device and can return to the supply station to pick up a new spreading device.

The X-Y-Z positioning device can be of any type known in the art of dispensing reagents. There can be one or a plurality of X-Y-Z positioning devices that can move independently to reagent supply stations or spreading device supply stations to pick up and dispense reagents from a remote source inside the staining apparatus or outside the staining apparatus.

A wet, recently floated, tissue section on a microscope side can be placed onto a slide support element and is moved into an individual reaction compartment or common pressurization chamber to apply pressure to the tissue section to further flatten out the section to the microscope slide before, during, or after the heat plate is turned on to melt the paraffin and securely attach the tissue or biological specimen to the microscope slide.

The microscope slide once stained can be coverslipped by a dry film adhesive glass coverslip by applying a solvent to the slide then tilting the slide support element at an angle to the coverslip dispenser and then the coverslip is touched at one edge to the microscope side and the slide support is moved back to horizontal placing the coverslip on the slide. The heating plate is turned on to dry the coverslip prior to removal of the slide for examination under a microscope.

The present invention contemplates that the microscope slides and reagents used herein can be heated by magnetic induction. This embodiment would be in the place of wired heating elements in the individual reaction compartment and individual slide support element. The reaction compartment and or slide support element would have metal associated therewith for magnetic induction heating.

Magnetic Induction heating is the process of heating an electrically conducting object, like a metal, by electromagnetic induction. Electromagnetic induction heating is the production of voltage across a conductor situated in a changing magnetic field or a conductor moving through a stationary magnetic field (Faraday's Law). This changing magnetic field generates eddy currents within the metal and the resistance leads to Joule heating of the metal. This type of heater is known, for example, in the art of cooking ranges and cook top surfaces (Waring Pro SB-30, Pro ICT100, Waring Products 314 Ella T. Grasso Avenue, Torrington, Conn. 06790). An induction heater (for heating a reagent on or around the biological specimen or just the biological specimen) consists of an electromagnet, through which a high-frequency alternating current (AC) is passed. Commercial power line frequency is acceptable to induce the primary inductor or electromagnet. Heat may also be generated by magnetic hysteresis losses in materials that have significant relative permeability. The frequency of AC used depends on the object size, material type, coupling (between the work coil and the object to be heated) and the penetration depth. Magnetic induction works best with cast iron, steel, stainless steel, ferrite based metal(s) and any coated metal of these types. The cast iron, steel, stainless steel, ferrite based metal(s) can be coated or intergraded with glass, ceramic or enamels, for example to have excellent anti-corrosive properties. Any coating known in the art of metal coating that can be heated can be use and are contemplated. Copper to some degree can be used. Magnetic induction heating doesn't heat non-metal objects. The primary inductor (electromagnet) would be positioned around the metal slide support element heating plate, or any other metal associated with a slide support, reaction compartment, common camber, reagent support, reagent containers, reagent conduits, etc. The metal slide support element or metal heat plate, or magnetic induction inducible heating material, for example, is heated by a commercial power line frequency (current) induced in it by a primary inductor (electromagnet). This type of heating of any metal present in the staining apparatus that is required to be heated to transfer (conduction heating) the heat to a reagent or just the biological specimen is advantageous in the present invention. Just the metal in the reaction compartment and slide support element would get hot to heat the reagent. The individual reaction compartment can be constructed of metal, metal and glass, metal and ceramic, or metal and a plastic polymer for use with a magnetic induction heating device. The individual slide support element can be constructed of metal, metal and glass, metal and ceramic, or metal and a plastic polymer for use with a magnetic induction heating device. Since the present invention has independently moving processing components (i.e.—independently moving slide supports, independently moving reaction compartments, independently moving reagent supports, etc.) this method of heating doesn't require hard electrical wiring to each heater or heaters. This use of magnetic induction to heat reagents or the biological specimen or both, reduces the clutter and cost of hard wiring each heater(s) of the present invention. Each reaction module or staining module can have at least one separate independently working magnetic inductor to heat an electromagnetic inducible metal that can then conductively transfer its heat to a reagent or biological specimen for a particular heat requiring protocol. There may also be more than one magnetic inductor for heating more than one metal source of the reaction module or staining module. The heated plate(s) or heated metal that is heated by Joule heating is extremely fast, controllable, and efficient. The heated metal plates or heated metal structures can be regulated in the range of less than 1° C. to exceeding 1000° C. More preferable the temperature regulation can be in the range of 20° C. to 180° C., depending on the heating requiring protocol. Any processing device can be constructed of an electromagnetic inducible metal and can have any shape. Shapes made of an electromagnetic inducible metal like tubes, plates, pins, ducts, dispensers, supports, of all types of shapes and construction are known and are contemplated. The processing devices of the present invention would be constructed mostly of non-metal materials and only the heating areas being constructed of an inducible material like metal. The microprocessor can regulate the temperature of any electromagnetically-inducible metal by adjusting the voltage or current to the at least one primary inductor (electromagnet) therefore regulating the electromagnetic inducible metal(s) (i.e., slide support element, heat plate, reaction compartment heated wall(s), reagent strip support heater, reagent containers heater, etc.) temperature associated with each component of the staining apparatus. It is known that any and all type of heating method along with magnetic induction heating is contemplated and any combination of these types of heaters (i.e.—infra red, conductive, convection, radiant, foil, kapton, conductive inks, magnetic induction, microwaves, etc.) can be used in each slide support element or reaction compartment. The electromagnetically inducible metal(s) can be quickly cooled once the primary inductor is turn off, because it is not necessary to wait for the heating means to cool down as well. When the electromagnetic induction is turned off the heat stops generating at the inducible metal site and the cooling process starts immediately without having to wait for the heating source (i.e., electromagnetism) to cool down along with the heated inducible metal. Just the inducible metal is cooled alone. This is in stark contrast for the cooling method of a conventional conduction heat source which requires the cooling of the conduction heat source in lockstep with its heated plate. The reaction compartment can be made entirely of glass or ceramics as to not be heated by the magnetic induction heating device. The inside of the reaction compartment can be engineered to be the magnetic induction heating device that heats the slide support element metal heat plate or the entire slide support element if it was constructed of metal. The advantage to this is the outside of the reaction compartment can remain cool to the touch and only the slide support element or slide support would be heated by the magnetic induction device to heat the reagent present on or associated with the microscope side. A user can place a bench unit, field unit, or small scale version of the staining apparatus (e.g., comprising 5-15 reaction compartments) near their microtome or processing table during preparation of a microscope slide once the tissues is floated onto the microscope slide the user can press the individual slide support element's eject/insert button and the individual slide support element inside the staining apparatus would then automatically move out of the staining apparatus and the user could then place the wet microscope slide onto the individual slide support element. The user could then press the appropriate button on the staining apparatus to cause the electromagnet to induce the individual slide support element metal plate directly under only the microscope slide to start heating the microscope slide with biological specimen attached. The slide support element metal plate would be heated causing heating of the microscope slide thereon without heating the remainder of the slide support element because it is constructed from a non-metal material like glass, for example. If the user would accidently touch the slide support element he or she would not feel the heat because only the heating plate of the slide support element and microscope slide thereon are being heated and the majority of the slide support elements mass (i.e., glass slide support) is not heated. The user can then let the slide support element stay outside the staining apparatus or move the slide support element into the staining apparatus by slightly pushing in on the slide support element to activate the automated movement of the slide support element into the staining apparatus. The user can alternatively press the eject/insert button again to automatically move the slide support element into the staining apparatus without pushing in on the slide support element. This movement is similar to a CD-ROM drawer or door on a personal computer and is described in detail elsewhere in this application. Once all of the microscope slides are placed on their individual slide support elements the user would move all the slide support elements into the staining apparatus either by pushing each individual eject/insert button for each slide support element or press the appropriate icon to move all the open slide support elements into the staining apparatus at the same time. There are icons and buttons present on the staining apparatus to move just one slide support element out of the staining apparatus and into the staining apparatus or move all the slide support elements together out of the staining apparatus or into the staining apparatus. An alternate embodiment of the present invention using magnetic induction heating is the use of a disposable individual slide support element and or a disposable individual reaction compartment or both that has at least one area being metal or an inducible metal or material that can be heated by magnet induction is contemplated. A further example is the use of a metal pan or inducible material in the cavity of the slide support element or the metal pan or inducible material in the head space of the reaction compartment. The magnetic induction heating device would then only heat the metal pan or inducible material in the slide support element, therefore heating D.I. water, for example, in the metal pan to produce steam that would pressurize the reaction compartment and heat the reagent on or associated with the biological specimen on the microscope slide. The method of magnetic induction heating contemplated herein is preferred because it can be controlled precisely depending on the amount of heat required and the amount of steam being generated to produce the desired level of pressurization without the necessity of releasing of the pressure being produced by steam generation to control pressure level. The magnetic field can be adjusted to regulate the heat temperature of the metal pan therefore increasing or decreasing the pressure contained in the reaction compartment for pressure regulation. Any combination of metal and non-metal in the construction of the individual reaction compartment or individual slide support element is contemplated. A magnetic induction heating device can be in or around the individual reaction compartment and/or in or around the individual slide support element. Magnetic induction can be used as long as there is metal or an inducible material either in the reaction compartment and/or metal present in the slide support element that can be heated by a magnetic induction heating device. The pressurizable common chamber can also employ magnetic induction to heat the walls of the pressurizable common chamber and or the metal slide support elements or areas requiring heating by magnetic induction of a metal or inducible material inside the pressurizable common chamber.

The staining apparatus can be relatively small, having just 5-20 sets of reaction components for example. This compact "point of use" staining apparatus can be positioned at the microtome or cryostat. A user can place wet microscope slides with their newly floated tissue section attached or frozen tissue attached onto the staining apparatus at the point of microtomy. Once the slides have been placed onto the staining apparatus, the apparatus can be moved to an area for staining the slides or just left near the microtome or cryostat to start the staining process. The automated leveling feature (described elsewhere in this application), of the present invention, can "level" the staining apparatus prior to staining or treatment initiation. The user needs only the reagent pack for each particular slide protocol to be placed into or onto the reagent pack support device and start the protocol. The entire reagent protocol, including rinses and application of a coverslipping mountant, can be provided by the reagent pack with no need for bulk fluid sources if desired. The entire protocol from start to finish is preferably supplied from the reagent pack. If the apparatus requires bulk fluid sources, the apparatus can have attached bulk fluids in containers that can be small and quickly refillable without stopping the staining apparatus because the bulk fluid containers can be linked together in a series or parallel for quick removal, filling, or disposal of bulk reagents and bulk waste.

The staining apparatus in one embodiment is adapted for pressurized pre-treatment only. It is constructed so as to perform only High Pressure Epitope Retrieval (HiPer™) pretreatments without further staining the slide. This HiPer™ apparatus can perform "Heat Induced Epitope Retrieval" [HIER] and or High Pressure Epitope Retrieval (HiPer™) pretreatment protocols. This embodiment is useful in particular when labs have an existing manual or automated staining platform or system that needs the added benefit of quick and efficient high temperature pre-treatment protocols prior to placing slides onto their existing automated or manual staining systems. The HiPer™ apparatus can use reagent packs for different types of heat induced epitope retrieval solutions or bulk fluid containers for use with the ports in each reaction module. The HiPer™ apparatus can move individual slides into and out of a pressurizable common chamber without leakage of the pressure contained in the pressurizable common chamber. The HiPer™ apparatus features Independent Access™, the mechanics of which are described elsewhere in this application.

The HiPer™ apparatus can also be adapted to move a plurality of slides on a single slide support device into and out of a pressurizable common chamber for a pre-treatment under pressurization, prior to further staining. A plurality of slides movable on a common support can be moved into and out of the pressurizable common chamber. The plurality of slides is moved into the inner space of the common chamber; a reagent can be dispensed onto each individual microscope slide either independently or simultaneously. This apparatus can use reagent packs or dispense reagents from a bulk reagent solution container by ports such as dispenser elements described elsewhere in this application. The pressurizable common chamber is closed and is subjected to pressure and heat to treat the biological specimen on the microscope slide. The heating means and pressurization means are explained elsewhere in this application. The reagent on or associated with the biological specimen is preferable on only the microscope slide.

The staining apparatus of the invention, in any embodiment described herein, can have a hand held or stationary scanner like IRISPen™ Express 6 (I.R.I.S. Group s.a. 10 rue du Bosquet, B-1348, Louvain la Neuve, Belgium) or any scanner or digitizer that can "scan" the entire microscope slide before, during and or after the biological specimen has been processed. Any scanner or digitizer known in the art can be used. This scanner or scanners provides information to the exact location or the position of the biological specimen (i.e., tissues section(s)) on the microscope slide in relation to the frosted, Colormark™, Colorfrost™, or otherwise labeled end of the microscope slide. The scanner can also use or store the information provided on the labeled end. The scanner can scan before, during, or after the slide is stained to store information to give the user the digital account of the entire staining protocol that can be stored in memory of the microprocessor and be retrieved at a later date for evaluation. The stored information can be for any OCR code or codes on the slide's labeled end along with the digital image of the biological specimen before, during, and after the completed processing or staining. The scanner may also be inside the staining apparatus and is movable inside the staining apparatus such as described previously in regard to the X-Y-Z processing device. Further each set of reaction components can have an independently moving scanner specific to only one set of reaction components. The scanner(s) can be stationary and the slide support element is movable to provide the scanning motion. The scanner can be inside the staining apparatus or outside the staining apparatus or both. There is at least one scanner present for the staining apparatus to capture digital images of the biological specimen on the microscope slide and the labeled end of the microscope slide, an example being, the tissue section can be scanned and the staining apparatus detects where the biological specimen is positioned relative to the labeled end of the microscope slide. The staining apparatus can now more effectively and efficiently dispense or treat only the area of the microscope slide the biological specimen occupies. The location, area used by the biological specimen, and biological specimen(s) information (i.e., size, area, pieces of tissue(s) present, cells, agglutination patterns, color, texture, inking colors for margin identification, etc.) along with the information collected from any OCR code, machine readable code(s), letters, numbers, symbols, written information, etc. present on the labeled end of the microscope slide can be compiled, calculated, arranged, digitally stored, and retrieved for later analysis.

The reagent(s) used with the spreading device described in regard to FIGS. 37-39B can have an additive to help spread or give substance or body to the reagent being spread by the spreading device. Thickening agents like Xanthan gum, glycols, thickeners, polyols, with or without detergents like Brij, Tween, Igepal, ionic and non-ionic detergents can be present in any reagent to be spread by the spreading device.

TREATMENT PROTOCOL EXAMPLES

Example 1

(1) Place microscope slide on slide support element and enclose within reaction compartment;
(2) Add antigen recovery buffer;
(3) Set slide heater at 130° C.;
(4) Pressure regulator set at 23 psig (259.9 kPa);
(5) Antigen recovery buffer reaches 125° C.;
(6) Incubate at 125° C. for 10 minutes;
(7) Turn off heater and turn on air or liquid cooling system;
(8) Cool 5 minutes; and
(9) Rinse with buffer and proceed with staining protocol.

Example 2

(1) Place microscope slide on support element;
(2) Enclose microscope slide within individual reaction compartment;
(3) Dispense 1-2 ml of antigen retrieval reagent onto microscope slide;
(4) Close all external ports;
(5) Open pressure port to pre-pressurize reaction compartment to about 25 psig (273.7 kPa);
(6) Turn on heat plate to reach about 120° C. on slide;
(7) Set pressure regulator to maintain 120° C. temperature by regulating the reaction compartment's pressure;
(8) Reagent reaches a temp of 120° C.;
(9) Heating is maintained for 30 minutes at about 120° C.;
(10) Turn off heater and turn on air or liquid cooling system;
(11) Cool 5-10 minutes;
(12) Release pressure to atmospheric pressure;
(13) Cool antigen retrieval reagent;
(14) Rinse slide with PBS wash buffer; and
(15) Proceed with staining protocol.

Example 3

Three mls of antigen recovery buffer present in reaction compartment can be heated to a particular reaction temperature at a particular pressure, including for example: 100° C.@8 psig (156.6 kPa), 106° C.@10 psig (170.3 kPa), 110° C.@12 psig (184.0 kPa), 115° C.@15 psig (204.7 kPa), 120° C.@16 psig (211.6 kPa), 125° C.@23 psig (259.9 kPa), or 130° C.@30 psig (308.1 kPa), 140° C.@40: retrieval buffer after a 60 minutes treatment time.

Example 4

Ambient Temperature with Pressure Staining Protocol
1) Place slide on slide support;
2) Close chamber to seal slide support to chamber;
3) Dispense reagent by reagent pack or other dispensing element;
4) Pressurize the chamber with a separate gas to desired pressure (50-100 psig: 446-790.6 kPa);
5) Incubate the reagent for a desired time (10-120 minutes);
6) Depressurize the chamber by opening the waste port;
7) Rinse slide of reagent by rinsing and/or tilting and rinsing the slide;
8) Repeat steps 3-7 until all reagents are dispensed for a particular protocol and for a desired time.

Example 5

High Temperature Antigen Retrieval Protocol with Pre-Pressurization
1) Place slide on slide support;
2) Close chamber to seal slide support to chamber;
3) Dispense reagent by reagent pack or other dispending element onto the microscope slide;
4) Pressurize the chamber with a separate gas to desired pressure (15-30 psig: 204.7-308.1 kPa);
5) Turn on at least one heating element (i.e., slide heater, chamber heater, cavity heater) and heat to 125° C.;
6) Pressure is maintained at 15-20 psig (204.7-239.2 kPa) by the pressure release valve or heating modulation (i.e., hearing elements turning off and on);
7) Incubate reagent at 125° C. for 10-30 minutes;
8) Turn heaters off and turn on cooling ducts (liquid or air) until reagent drops below 50° C.;
9) Depressurize the chamber sending condensation and pressure out the waste port;
10) Rinse slide of reagent by rinsing and/or tilting and rinsing the slide;
11) Dispense regent and incubate with or without pressure and/or with or without heat for a desired time;
12) Repeat steps 9-10 until all reagents are dispensed.

Example 6

High Temperature Antigen Retrieval Protocol without Pre-Pressurization
1) Place slide on slide support;
2) Close chamber to seal slide support to chamber;
3) Dispense reagent by reagent pack or other dispending element and fill up the chamber with reagent by totally immersing the entire slide in reagent (i.e., antigen retrieval reagent);
4) Turn on at least one heating element (i.e., slide heater, chamber heater, cavity heater) and heat to 125° C.;
5) Pressure is produced by the reagent boiling;
6) Pressure is maintained at 25 psig (273.7 kPa) by the pressure release valve or heating modulation (i.e., heating elements turning off and on);
7) Reagent is incubated at a temperature of 125° C. for 10-30 minutes;
8) Turn heaters off and turn on cooling ducts (liquid or air) until reagent drops below 50° C.;
9) Depressurize the chamber sending condensation, reagent, and pressure out the waste port;
10) Rinse slide or reagent by rinsing and/or tilting and rinsing the slide;
11) Dispense reagent and incubate with or without pressure and/or with or without heat for a desired time;
12) Repeat steps 10-11 until all reagents are dispensed.

Example 7

High Temperature Antigen Retrieval Protocol—Cavity Produces Steam to Maintain High Heat Conditions with Pressurization
1) Place slide on slide support;
2) Close chamber to seal slide support to chamber;

3) Dispense reagent by reagent pack or other dispending element onto the microscope slide;
4) Add deionized (D.I.) water, or other liquid reagent to the cavity below the slide (deionized water not contacting the microscope slide);
5) Turn on slide heating element and cavity heaters and heat to 125° C.;
6) Pressure is produced by the deionized water boiling in the cavity and producing steam to heat the reagent on the microscope slide;
7) Pressure is maintained at 25 psig (273.7 kPa) by the pressure release valve or heating modulation (i.e., heating elements turning off and on);
8) Reagent is incubated at a temperature of 125° C. for 10-60 minutes;
9) Turn heaters off and turn on cooling ducts (liquid or air) until reagent drops below 50° C.;
10) Depressurize the chamber sending condensation, deionized water and pressure out the water port;
11) Rinse slide of reagent by rinsing and/or tilting and rinsing the slide;
12) Dispense reagent and incubate with or without pressure and/or with or without heat for a desired time;
13) Repeat steps 10-11 until all reagents are dispensed.

Example 8

Using the Individual Sets of Reaction Components with Hand Held or Stationary Reagent OCR Code Reader
1) Push or press eject/load button on individual reaction module (i.e., set of reagent components) front panel (near the reaction compartment opening or individual eject/load icon on computer screen for the chosen reaction module).
2) The individual slide support element ejects outside or moves out of the staining apparatus.
3) Place the microscope slide onto the individual slide support element (e.g., onto the hotplate).
4) The individual digital camera projects the labeled end of the slide on the microprocessor screen for better viewing of written information on the labeled end of the microscope slide.
5) Chose the correct reagent pack and hand scan the reagent pack OCR or code.
6) The microprocessor loads the correct protocol and information for that particular reagent pack.
7) The microprocessor opens the reagent pack door and the reagent pack support device ejects or moves outside the staining apparatus.
8) Place the reagent pack on the reagent pack support device and press the start button at the individual reaction module front panel or press the start icon on the microprocessor screen related to that particular reaction module.
9) Both the independently moving slide support element and independently moving reagent pack support device automatically move into the staining apparatus independently.
10) Protocol initiates.
11) After the protocol is completed, the individual reaction module will have both a sound and visual alert to the finish protocol.
12) Press the finished button on the individual reaction module front panel or icon on the microprocessor screen.
13) The finished slide is ejected out of the staining apparatus for removal from the independently moving slide support element.
14) The used reagent pack is then eject or removed from the staining apparatus and is discarded.
15) The slide support element and reagent pack support device is then moved back into the staining apparatus.

Example 9

Using the Individual Reaction Modules with Automated Reagent OCR Reader
1) Push or press eject/load button on individual reaction module front panel (near the reaction compartment opening or individual eject/load icon on computer screen for the chosen reaction module).
2) The individual slide support element ejects outside or moves out of the staining apparatus.
3) Place the microscope slide onto the individual slide support element (e.g., onto the hotplate).
4) The individual digital camera projects the labeled end of the slide on the microprocessor screen for better viewing of written information on the labeled end of the microscope slide.
5) Push or press eject/load button of the reagent pack support device.
6) The microprocessor opens the reagent pack door and the reagent pack support device ejects or moves outside the staining apparatus.
7) Place the reagent pack on the reagent pack support device and press the start button at the individual reaction module front panel or press the start icon on the microprocessor screen related to that particular reaction module.
8) Both the independently moving slide support element and independently moving reagent pack support device automatically move into the staining apparatus independently.
9) The scanner inside the staining apparatus reads the OCR code or code on the reagent pack.
10) The program is now loaded along with the information of the reagent pack.
11) Protocol automatically initiates.
12) After the protocol is completed, the individual reaction module will have both a sound and visual alert to the finish protocol.
13) Press the finished button on the individual reaction module front panel or icon on the microprocessor screen.
14) The finished slide is ejected out of the staining apparatus for removal from the independently moving slide support element.
15) The used reagent pack is then eject or removed from the staining apparatus and is discarded.
16) The slide support element and reagent pack support device is then moved back into the staining apparatus.

Example 10

Using the Individual Reaction Modules with a "Quick Code"
1) Push or press eject/load button on individual reaction module front panel (near the reaction compartment opening or individual eject/load icon on computer screen for the chosen reaction module).
2) The individual slide support element ejects outside or moves out of the staining apparatus.

3) Place the microscope slide onto the individual slide support element (e.g., onto the hotplate).
4) The individual digital camera projects the labeled end of the slide on the microprocessor screen for better viewing of written information on the labeled end of the microscope slide.
5) Push or press the reagent pack "quick code" on the individual reaction module front panel or icon on the microprocessor screen.
6) The program is now loaded along with the information of the reagent pack.
7) The microprocessor opens the reagent pack door and the reagent pack support device ejects or moves outside the staining apparatus.
8) Place the reagent pack on the reagent pack support device and press the start button at the individual reaction module front panel or press the start icon on the microprocessor screen related to that particular reaction module.
9) Both the independently moving slide support element and independently moving reagent pack support device automatically move into the staining apparatus independently.
10) Protocol automatically initiates.
11) After the protocol is completed, the individual reaction module will have both a sound and visual alert to the finish protocol.
12) Press the finished button on the individual reaction module front panel or icon on the microprocessor screen.
13) The finished slide is ejected out of the staining apparatus for removal from the independently moving slide support element.
14) The used reagent pack is then eject or removed from the staining apparatus and is discarded.
15) The slide support element and reagent pack support device is then moved back into the staining apparatus.

In summary, the invention in one embodiment contemplates an in situ antigen recovery and staining apparatus, comprising a plurality of independently operable reaction compartments having an inner space, a slide support element able to support a microscope slide in the reaction compartment, the slide support element positionable within or adjacent the inner space of the reaction compartment for sealing the microscope slide therein wherein the reaction compartment is pressurizable (or optionally depressurizable) to maintain an internal pressure which exceeds (or is below) atmospheric pressure, and a dispensing element (e.g., reagent pack, port, or plunger) for dispensing a reagent onto the microscope slide while the reaction compartment is pressurized (or alternatively, not pressurized), and may further comprise a heating element for heating the microscope slide upon the slide support element.

The staining apparatus may further comprise a reagent pack support device for supporting a reagent pack having one or more reagent containers which contain or is able to contain a reagent therein, wherein the reagent pack support device supports the reagent pack in a position external to the reaction compartment and/or the slide support element, and the dispensing element may be adapted to engage the reagent container of the reagent pack thereby causing the reagent to be delivered from the reagent container into the inner space of the reaction compartment and onto the microscope slide or directly only the microscope slide disposed directly on the slide support element inside or outside of the reaction compartment.

Preferably, each of the reaction compartments of the staining apparatus is individually and independently pressurizable (or, optionally, depressurizable) and each of the heating elements is individually and independently operable and heatable.

In the staining apparatus, the reaction compartment may be pressurizable before, during, or after the heating element heats the microscope slide, the heating element may be a component of the slide support element and may be positionable directly beneath the microscope slide, the reaction compartment may have a cylindrical, tubular shape wherein the slide support element has a cylindrical shape, or the reaction compartment may have a rectangular shape, such that the slide support element has a rectangular shape.

In the in situ antigen recovery and staining apparatus, each slide support element is preferably independently movable in relation to each other slide support element, each reagent pack is independently movable in relation to each other reagent pack, each reaction compartment is independently movable in relation to each other reaction compartment, and each dispensing element (plunger, etc.) is independently movable in relation to each other dispensing element. The reaction compartment is preferably pressurizable to maintain a pressure above atmospheric pressure, such as 0 to 350 psig (101.3-2514 kPa), to a pressure of 1 to 100 psig (108.2-790.6 kPa), to a pressure of 5 to 50 psig (135.8-446.0 kPa), or to a pressure of 10 to 40 psig (170.3-377.0 kPa), or is depressurizable to maintain a pressure below atmospheric pressure to a level as low as 100 kPa to 10 kPa to 1 kPa to 100 Pa to 10 Pa to 1 Pa to 0.1 Pa.

In the staining apparatus, the reagent disposed onto or about the microscope slide may be heated, for example, to a temperature of 25° C. to 37° C., 37° C. to 56° C., 56° C. to 85° C., 85° C. to 100° C., 100° C. to 125° C., 125° C. to 135° C., 135° C. to 150° C., 150° C. to 175° C., 175° C. to 200° C., 200° C. to 225° C., 225° C. to 250° C., 250° C. to 275° C., 275° C. to 300° C., 300° C. to 325° C., or 325° C. to 350° C. The reaction compartment, when present, may be stationary or movable, and each reagent pack support device associated therewith may be stationary or movable. When the slide support element is stationary, the reaction compartment may be movable, and the reagent pack support device may be stationary or movable. When the slide support element of the reaction module is movable or stationary, and the reaction compartment is movable, and the reagent pack support device is movable, the reaction compartment may be movable independently of the reagent pack support device. Further, the reagent pack support device may be movable in either a forward or reverse direction to carry the reagent pack when loaded thereon in either a forward or reverse direction, and when the reagent pack support device is stationary, the reagent pack may be movable in either a forward or reverse direction when loaded thereon. The reagent pack support device and the reaction compartment may be connected to each other, or not connected. Each reaction compartment may comprise at least one of (1) an air duct for pressurizing the reaction compartment or causing mixing of the reagent on the slide, (2) a cooling duct for enhancing the rate of cooling of the heating element after heating, (3) a supply port for delivering a liquid to the slide support element, and (4) a drainage duct for removing reagents supplied to the microscope slide. The staining apparatus may comprise a separate reagent conduit for enabling delivery of reagent from each reagent pack into the corresponding reaction compartment, a heating device disposed about the reagent conduit for heating the reagent delivered therethrough, a heating device for heating the reaction compartment, and a heating device in the reagent pack support device for heating the reagent pack or portions thereof.

The slide support element of the apparatus may have a cavity in a position below the microscope slide for containing a quantity of solution and the cavity may have a cavity heater for heating the solution within the cavity. The dispensing element may be operable independently of the reagent pack support device (e.g., as a component of the X-Y-Z positioning device, and the dispensing element preferably functions to cause expulsion of reagent from a reagent container of the reagent strip and/or to dispense a reagent or solution from a reagent or solution source remote from the reagent pack such as from the remote reagent source. The slide support element may receive reagent from the reagent pack or reagent or solution from a remote source when the slide support element is disposed inside or outside of the reaction compartment. The dispensing element is preferably able to apply suction, or is able to apply liquid, air, or gas under pressure. The slide support element may be enclosable within the reaction compartment by moving the slide support element into the reaction compartment or by moving the reaction compartment about the slide support element. The slide support element may be tiltable to allow drainage of reagent or solution from the microscope slide. The plurality of sets of reaction components can be assembled into at least one chamber to form a staining apparatus. Each slide support element, reagent pack support device, dispensing element, and reaction compartment of the staining apparatus is preferably separately replaceable or exchangeable, and preferably has means for controlling or releasing pressure from or regulating pressure within the reaction compartment.

The present invention also contemplates a reconfigurable reagent dispensing pack, comprising a plurality of reagent module, each reagent module comprising a tile and a reagent container secured thereto, each reagent module preferably adapted to be attachable to and detachable from an adjacent reagent module such that once the plurality of reagent modules are attached together in a first sequence, one or more of the reagent modules can be detached and reattached to reconfigure the plurality of reagent modules in a second sequence different from the first sequence. The reconfigurable reagent dispensing pack may have a connecting link for connecting adjacent reagent modules, and an injector for enabling a reagent within the reagent container to be dispensed from the reagent container, and the reagent container may be removable from the tile in one embodiment. Further, at least one of the reagent containers contains a reagent selected from the group consisting of antigen retrieval reagents, RNA and DNA probes, citrate buffer, EDTA, TRIS, PBS, with or without surfactants or detergents like SDS, Tween, Brij, ionic and non ionic detergents, and silicone additives, rinse buffers, immunohistochemical reagents, histochemical reagents, in-situ hybridization reagents, PCR reagents, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives.

Alternatively, the reconfigurable reagent dispensing pack may comprise a base, having a plurality of container platforms, and a plurality of reagent containers, with each container platform having a reagent container secured thereto, wherein each reagent container is adapted to be attachable to and detachable from the container platform such that once the plurality of reagent containers are attached together in a first sequence, one or more of the reagent containers can be detached and reattached to a different container platform to reconfigure the plurality of reagent containers in a second sequence different from the first sequence, thereby forming a reconfigured reagent dispensing pack. The reagent container may be positioned upon a tile which is detachable from the base. The reagent container or container platform may further comprise an injector for enabling a reagent within the reagent container to be dispensed from the reagent container.

Alternatively, the reconfigurable reagent dispensing pack may comprise a plurality of reagent modules, each reagent module comprising a tile and a reagent container secured thereto, wherein the tiles are initially constructed in a unitary, integral configuration and each tile is adapted to be attachable to and detachable from an adjacent tile such that the reagent modules are connected in a first sequence, and wherein when one or more of the tiles is detached, the one or more tiles can be reattached to reconfigure the plurality of reagent modules in a second sequence different from the first sequence, and may further comprise a connecting link for re-connecting tiles of adjacent reagent modules. The reagent module may further comprise an injector for enabling a reagent within the reagent container to be dispensed from the reagent container, and the reagent container may be removable from the tile.

In another embodiment, the present invention contemplates a method of treating a microscope slide, comprising: providing a plurality of independently operable reaction compartments each having an inner space, a plurality of slide support elements each able to support at least one microscope slide in a horizontal position, the slide support element positionable within or adjacent the inner space of the reaction compartment for sealing the microscope slide therein, and a dispensing element for dispensing a reagent into the reaction compartment, then disposing the microscope slide onto the slide support element, positioning the microscope slide within the reaction compartment, pressurizing the reaction compartment to maintain an internal pressure which exceeds atmospheric pressure, and actuating the dispensing element to cause the reagent to be delivered into the reaction compartment while the reaction compartment is pressurized and wherein the reagent is delivered at a pressure which exceeds the pressure within the reaction compartment, and optionally heating the microscope slide and reagent within the reaction compartment.

Preferably the invention comprises a method of treating a microscope slide, comprising, providing a plurality of independently operable reaction compartments each having an inner space, a plurality of slide support elements able to support a microscope slide, the slide support element positionable within or adjacent the inner space of the reaction compartment for sealing the microscope slide therein, a heating element for heating the microscope slide, a reagent pack support device for supporting a reagent pack having a plurality of reagent containers each of which contains or is able to contain a reagent therein, wherein the reagent pack support device supports the reagent pack in a position external to and adjacent the reaction compartment, and a dispensing element for engaging the reagent container thereby causing the reagent to be delivered from the reagent container onto the microscope slide, and wherein each of the reaction compartments of the plurality of reaction modules is individually and independently pressurizable (or, optionally, depressurizable) and wherein each of the heating elements of the slide support elements is individually and independently heatable. The microscope slide disposed on the slide support element, the slide support element and microscope slide thereon is then positioned within the reaction compartment, the heating element is activated to heat the slide, the reaction compartment is then pressurized to maintain an internal pressure which exceeds atmospheric pressure.

In the method, the step of pressurizing (or depressurizing) the reaction compartment may occur before, during, or after the heating of the microscope slide by the heating element. The reaction compartment may have a cylindrical, tubular shape for enhancing pressure distribution within the reaction compartment. The slide support element of each reaction module may be moved independently in relation to each other slide support element, each reagent pack may be moved independently in relation to each other reagent pack, and each dispensing element may be moved independently in relation to each other dispensing element. The reaction compartment may be pressurized to a pressure of above 0 to 350 psig (101.3-2514 kPa), to a pressure of 1 to 100 psig (108.2-790.6 kPa), to a pressure of 5 to 50 psig (135.8-446.0 kPa), or to a pressure of 10 to 40 psig (170.3-377.0 kPa). The reaction compartment may be depressurized to maintain a pressure below atmospheric pressure to a level as low as 100 kPa to 10 kPa to 1 kPa to 100 Pa to 10 Pa to 1 Pa to 0.1 Pa. The reagent disposed onto or about the microscope slide may be heated to a temperature of 25° C. to 37° C., 37° C. to 56° C., 56° C. to 85° C., 85° C. to 100° C., 100° C. to 125° C., 125° C. to 135° C., 135° C. to 150° C., 150° C. to 175° C., 175° C. to 200° C., 200° C. to 225° C., 225° C. to 250° C., 250° C. to 275° C., 275° C. to 300° C., 300° C. to 325° C., to 325° C. to 350° C. The step of positioning the slide support element may comprise moving the slide support element into the reaction compartment while the reaction compartment is stationary, or the step of positioning the slide support element may comprise moving the slide support element and moving the reaction compartment. The reagent pack may be positioned in a dispensing position by moving the reagent pack support device thereby moving the reagent pack to the dispensing position, or by moving the reagent pack while the reagent pack support device is stationary. The method may comprise moving the slide support element of the reaction module, moving the reaction compartment is movable, and moving the reagent pack support device, wherein the reaction compartment is movable independently of the reagent pack support device.

While the invention has been described herein in connection with certain embodiments so that aspects thereof may be more fully understood and appreciated, it is not intended that the invention be limited to these particular embodiments. On the contrary, it is intended that all alternatives, modifications and equivalents are included within the scope of the invention as defined by the appended claims. Thus the examples and embodiments described herein, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

Changes may be made in the construction and the operation of the various components, elements and assemblies described herein or in the steps or the sequence of steps of the methods described herein without departing from the spirit and scope of the invention as defined in the following claims.

What is claimed is:

1. A microscope slide staining system, comprising:
a chamber having an inner space;
a plurality of reaction compartments contained in the inner space, each of the reaction compartments having an inner space;
a plurality of independently movable slide support elements, each able to support a microscope slide with a biological specimen supported thereon, and wherein each slide support element is positionable relative to the reaction compartments so that the biological specimen on the microscope slide is positionable in and out of the reaction compartment corresponding thereto;
sealing means corresponding to each reaction compartment for forming a pressure-tight seal for sealing the inner space of the reaction compartment;
pressurizing means for pressurizing the inner space of each reaction compartment after the inner space has been sealed by the sealing means wherein each reaction compartment is pressurizable independently of each other reaction compartment; and
a plurality of separate independently movable spreading devices such that at least one of the spreading devices being associated with one of the slide support elements for spreading at least one reagent on the biological specimen and the microscope slide, each spreading device extending across at least a portion of the slide support element in a way that the spreading device defines a gap between the spreading device and the microscope slide when the microscope slide is positioned on the slide support element.

2. The system of claim 1, wherein the pressurizing means is a plurality of heating elements such that at least one of the heating elements is associated with one of the slide support elements to heat the reagent on the biological specimen and the microscope slide.

3. The system of claim 1, further comprising a plurality of heating elements such that at least one of the heating elements is associated with one of the slide support elements to heat the reagent on the biological specimen and the microscope slide.

4. The system of claim 3, wherein the pressurizing means can pressurize the sealed inner space of the reaction compartment to a pressure level above atmospheric pressure before, during, or after the at least one heating element heats the reagent on the biological specimen and the microscope slide.

5. The system of claim 1, wherein the pressurizing means is a gas.

6. The system of claim 1, wherein the pressurizing means can pressurize the sealed inner space of the reaction compartment to a pressure level above atmospheric pressure.

7. The system of claim 1, wherein at least a portion of each reaction compartment has a tubular shape.

8. The system of claim 7, wherein at least a portion of each slide support element has a tubular shape.

9. The system of claim 1 wherein each reaction compartment is movable independently of each other reaction compartment.

10. The system of claim 1 wherein each reaction compartment is operable independently of each other reaction compartment.

11. The system of claim 1, wherein each of the spreading devices engages side edges of the microscope slide when the microscope slide is positioned on the slide support element.

12. The system of claim 1, wherein each of the spreading devices slides longitudinally along the microscope slide when the microscope slide is positioned on the slide support element.

13. The system of claim 1, wherein the gap is such that the reagent is caused to spread across the gap by capillary action upon the spreading device contacting the reagent.

14. The system of claim 1, wherein each of the spreading devices has a reservoir in which at least one reagent is stored in a way that the reagent is dischargeable from the reservoir onto the microscope slide in front of the spreading device when the microscope slide is positioned on the slide support element.

15. The system of claim 1, further comprising a plurality of reagent packs with at least one reagent container on each of the reagent packs containing at least one reagent, the reagent packs supported above the slide support elements such that the reagent contained in the reagent containers can be expelled from the reagent containers onto a respective one of the microscope slides in front of a respective one of the spreading devices when the microscope slide is positioned on the slide support element.

16. The system of claim 15, wherein each of the reagent packs has a plurality of reagent containers with each reagent container containing at least one reagent, the reagent packs being rotatable such that the reagents contained in the reagent containers can be selectively expelled from the respective reagent containers onto the respective one of the microscope slides in front of the respective one of the spreading devices when the microscope slide is positioned on the slide support element.

17. The system of claim 1, wherein each of the spreading devices engages a track on the slide support element when the microscope slide is positioned on the slide support element.

18. A microscope slide staining system, comprising:
a chamber having an inner space;
a plurality of reaction compartments contained in the inner space, each of the reaction compartments having an inner space;
a plurality of independently movable slide support elements, each able to support a microscope slide with a biological specimen supported thereon, and wherein each slide support element is positionable relative to the reaction compartments so that the biological specimen on the microscope slide is positionable in and out of the reaction compartment corresponding thereto;
sealing means corresponding to each reaction compartment for forming a pressure-tight seal for sealing the inner space of the reaction compartment;
pressurizing means for pressurizing the inner space of each reaction compartment after the inner space has been sealed by the sealing means wherein each reaction compartment is pressurizable independently of each other reaction compartment; and
a plurality of separate independently movable spreading devices such that at least one of the spreading devices being associated with one of the slide support elements for spreading at least one reagent on the biological specimen and the microscope slide, each spreading device extending across at least a portion of the slide support element in a way that the spreading device defines a gap between the spreading device and the microscope slide when the microscope slide is positioned on the slide support element,
wherein the pressurizing means is a plurality of heating elements such that at least one of the heating elements is associated with one of the slide support elements to heat the reagent on the biological specimen and the microscope slide,
wherein the heating elements pressurize the sealed inner space of the reaction compartments to a pressure level above atmospheric pressure by heating the regent on the biological specimen and the microscope slide to a temperature exceeding 100° C.

19. The system of claim 18, wherein at least a portion of each reaction compartment has a tubular shape.

20. The system of claim 18, wherein each reaction compartment is movable independently of each other reaction compartment.

21. The system of claim 20, wherein at least a portion of each slide support element has a tubular shape.

22. The system of claim 18 wherein each reaction compartment is operable independently of each other reaction compartment.

23. The system of claim 18, wherein each of the spreading devices engages side edges of the microscope slide when the microscope slide is positioned on the slide support element.

24. The system of claim 18, wherein each of the spreading devices slides longitudinally along the microscope slide when the microscope slide is positioned on the slide support element.

25. The system of claim 18, wherein the gap is such that the reagent is caused to spread across the gap by capillary action upon the spreading device contacting the reagent.

26. The system of claim 18, wherein each of the spreading devices has a reservoir in which at least one reagent is stored in a way that the reagent is dischargeable from the reservoir onto the microscope slide in front of the spreading device when the microscope slide is positioned on the slide support element.

27. The system of claim 18, further comprising a plurality of reagent packs with at least one reagent container on each of the reagent packs containing at least one reagent, the reagent packs supported above the slide support elements such that the reagent contained in the reagent containers can be expelled from the reagent containers onto a respective one of the microscope slides in front of a respective one of the spreading devices when the microscope slide is positioned on the slide support element.

28. The system of claim 27, wherein each of the reagent packs has a plurality of reagent containers with each reagent container containing at least one reagent, the reagent packs being rotatable such that the reagents contained in the reagent containers can be selectively expelled from the respective reagent containers onto the respective one of the microscope slides in front of the respective one of the spreading devices when the microscope slide is positioned on the slide support element.

29. The system of claim 18, wherein each of the spreading devices engages a track on the slide support element when the microscope slide is positioned on the slide support element.

30. A microscope slide staining system, comprising:
a chamber having an inner space;
a plurality of reaction compartments contained in the inner space, each of the reaction compartments having an inner space;
a plurality of independently movable slide support elements, each able to support a microscope slide with a biological specimen supported thereon, and wherein each slide support element is positionable relative to the reaction compartments so that the biological specimen on the microscope slide is positionable in and out of the reaction compartment corresponding thereto;

sealing means corresponding to each reaction compartment for forming a pressure-tight seal for sealing the inner space of the reaction compartment;

pressurizing means for pressurizing the inner space of each reaction compartment after the inner space has been sealed by the sealing means wherein each reaction compartment is pressurizable independently of each other reaction compartment;

a plurality of separate independently movable spreading devices such that at least one of the spreading devices being associated with one of the slide support elements for spreading at least one reagent on the biological specimen and the microscope slide, each spreading device extending across at least a portion of the slide support element in a way that the spreading device defines a gap between the spreading device and the microscope slide when the microscope slide is positioned on the slide support element; and a plurality of heating elements such that at least one of the heating elements is associated with one of the slide support elements to heat the reagent on the biological specimen and the microscope slide, wherein the pressurizing means can pressurize the sealed inner space of the reaction compartment to a pressure level above atmospheric pressure before, during, or after the at least one heating elements heat the reagent on the biological specimen and the microscope slide to a temperature exceeding 100° C.

31. The system of claim 30, wherein the pressurizing means is a gas.

32. The system of claim 30 wherein at least a portion of each reaction compartment has a tubular shape.

33. The system of claim 32, wherein at least a portion of each slide support element has a tubular shape.

34. The system of claim 30, wherein each reaction compartment is movable independently of each other reaction compartment.

35. The system of claim 30, wherein each reaction compartment is operable independently of each other reaction compartment.

36. The system of claim 30, wherein each of the spreading devices engages side edges of the microscope slide when the microscope slide is positioned on the slide support element.

37. The system of claim 30, wherein each of the spreading devices slides longitudinally along the microscope slide when the microscope slide is positioned on the slide support element.

38. The system of claim 30, wherein the gap is such that the reagent is caused to spread across the gap by capillary action upon the spreading device contacting the reagent.

39. The system of claim 30, wherein each of the spreading devices has a reservoir in which at least one reagent is stored in a way that the reagent is dischargeable from the reservoir onto the microscope slide in front of the spreading device when the microscope slide is positioned on the slide support element.

40. The system of claim 30, further comprising a plurality of reagent packs with at least one reagent container on each of the reagent packs containing at least one reagent, the reagent packs supported above the slide support elements such that the reagent contained in the reagent containers can be expelled from the reagent containers onto a respective one of the microscope slides in front of a respective one of the spreading devices when the microscope slide is positioned on the slide support element.

41. The system of claim 40, wherein each of the reagent packs has a plurality of reagent containers with each reagent container containing at least one reagent, the reagent packs being rotatable such that the reagents contained in the reagent containers can be selectively expelled from the respective reagent containers onto the respective one of the microscope slides in front of the respective one of the spreading devices when the microscope slide is positioned on the slide support element.

42. The system of claim 30, wherein each of the spreading devices engages a track on the slide support element when the microscope slide is positioned on the slide support element.

* * * * *